United States Patent [19]
Shin et al.

[11] Patent Number: 5,962,224
[45] Date of Patent: *Oct. 5, 1999

[54] ISOLATED DNA ENCODING P62 POLYPEPTIDES AND USES THEREFOR

[75] Inventors: Jaekyoon Shin, Westwood; Insil Joung, Boston; Ratna K. Vadlamudi, Norwood; Jack L. Strominger, Lexington, all of Mass.

[73] Assignee: Dana-Farber Cancer Institute, Boston, Mass.

[ * ] Notice: Under 35 U.S.C. 154(b), the term of this patent shall be extended for 03 days.

[21] Appl. No.: 08/574,959

[22] Filed: Dec. 19, 1995

[51] Int. Cl.$^6$ .............................. C12Q 1/68; C07H 21/04; C12N 15/85; C12N 15/00

[52] U.S. Cl. .......................... 435/6; 435/69.1; 435/70.1; 435/320.1; 435/325; 435/366; 536/23.1; 536/24.31; 536/24.33

[58] Field of Search .............................. 514/44; 435/69.1, 435/320.1, 6, 70.1, 325, 366; 536/23.1, 24.33, 24.5, 24.31

[56] References Cited

U.S. PATENT DOCUMENTS

| | | | |
|---|---|---|---|
| 5,578,708 | 11/1996 | Okazaki et al. | 530/399 |
| 5,585,479 | 12/1996 | Hoke et al. | 536/24.5 |

OTHER PUBLICATIONS

Chan, A., et al., "The Role of Protein Tyrosine Kinases and Protein Tyrosine Phosphatases in T Cell Antigen Receptor Signal Transduction," Annu. Rev. Immunol., vol. 12, 555–592 (1994).

Cleghon, V. and Morrison, D., "Raf–1 Interacts with Fyn and Src in a Non–phosphotyrosine–dependent Manner," *The Journal of Biological Chemistry*, vol. 269, No. 26, 17749–17755 (1994).

Gupta, S., et al., "The T–cell Antigen Receptor Utilizes Lck, Raf–1, and MEK–1 for Activating Mitogen–activated Protein Kinase," *The Journal of Biological Chemistry*, vol. 269, No. 25, 17349–17357 (1994).

Joung, I., et al., "Modification of Ser$^{59}$ in the Unique N–terminal Region of Tyrosine Kinase p56$^{lck}$ Regulates Specificity of its Src Homology 2 Domain," *Proc. Natl. Acad. Sci. USA*, vol. 92, 5778–5782 (1995).

Malek, S. and Desiderio, S., "A Cyclin–dependent Kinase Homologue, p130 $^{PITSLRE}$, is a Phosphotyrosine–independent SH2 Ligand," *The Journal of Biological Chemistry*, vol. 269, No. 52, 33009–33020 (1994).

Muller, A., et al., "A Limited Set of SH2 Domains Binds BCR Through a High–Affinity Phosphotyrosine–Independent Interaction," *Molecular and Cellular Biology*, vol. 12, No. 11, 5087–5093 (1992).

von Bonin, A., et al., "The βD–Sheet Residues of the Lck–derived SH2 Domain Determine Specificity of the Interaction with Tyrosine–phosphorylated Ligands in Ramos B Cells," *The Journal of Biological Chemistry*, vol. 269, No. 52, 33035–33041 (1994).

Winkler, D., et al., "Phosphorylation of Ser–42 and Ser–59 in the N–terminal Region of the Tyrosine Kinase p56$^{lck}$," *Proc. Natl. Acad. Sci. USA*, vol. 90, 5176–5180 (1993).

Wong, G., et al., "Molecular Cloning and Nucleic Acid Binding Properties of the GAP–Associated Tyrosine Phosphoprotein p62," *Cell*, vol. 69, 551–558 (1992).

James, Towards gene inhibition therapy: a review of progress and prospects in the field of antiviral antisense nucleic acids and ribozymes, Antiviral Chemistry and Chemotherapy, vol. 2(4), pp. 191–214, 1991.

Uhlmann et al., Antisense oligonucleotides: a new therapeutic principle, Chemical Reviews, vol. 90(4), pp. 543–584, Jun. 1990.

Tseng et al., Antisense oligonucleotide technology in the development of cancer therapeutics, Cancer Gene Therapy, vol. 1(1), pp. 65–71, Mar. 1994.

Gewirtz et al., Facility oligonucleotide delivery: helping antisense deliver on its promise, Proc. Natl. Acad. Sci., vol. 93, pp. 3161–3163, Apr. 1996.

Ngo et al., Computational complexity, protein structure prediction, and the Levinthal paradox, The Protein Folding Problem and Tertiary Structure Prediction, pp. 433–440, 1994.

Burbelo, P. et al., "p190–B, a New Member of the Rho GAP Family, and Rho are Induced to Cluster After Integrin Cross–linking," *The Journal of Biological Chemistry*, vol. 270, No. 52, 30919–30926 (1995).

DeVergne, O. et al., "A Novel Interleukin–12 p40–Related Protein Induced by Latent Epstein–Barr Virus Infection in B Lymphocytes," *Journal of Virology*, vol. 70, No. 2, 1143–1153 (1996).

Joung, I. et al., "Molecular Cloning of a Phosphotyrosine–Independent Ligand of the p56$^{lck}$ SH2 Domain," *Proc. Natl. Acad. Sci. USA*, vol. 93, 5991–5995 (1996).

*Primary Examiner*—George C. Elliott
*Assistant Examiner*—Andrew Wang
*Attorney, Agent, or Firm*—Amy E. Mandragouras; Lahive & Cockfield, LLP

[57] ABSTRACT

Isolated nucleic acid molecules encoding novel members of the p62 family of polypeptides which include, in preferred embodiment, an SH2 binding domain and a ubiquitin binding domain are described. Also disclosed are novel members of the p160 family of polypeptides. The p62 polypeptides and the p160 polypeptides of the invention are capable of modulating leukocyte activity, e.g., by stimulating a B cell response, including B cell proliferation, B cell aggregation, B cell differentiation, B cell survival, and/or stimulating a T cell response, e.g., T cell proliferation, T cell aggregation, T cell differentiation, and T cell survival, are disclosed. The p62 polypeptides and the p160 polypeptides of the invention are also capable of modulating ubiquitin-mediated degradation of cellular proteins. In addition to isolated nucleic acids molecules, antisense nucleic acid molecules, recombinant expression vectors containing a nucleic acid molecule of the invention, host cells into which the expression vectors have been introduced are also described. The invention further provides isolated p62 polypeptides and isolated p160 polypeptides, fusion polypeptides and active fragments thereof. Diagnostic and therapeutic methods utilizing compositions of the invention are also provided.

28 Claims, 52 Drawing Sheets p62.seg2 Length: 2083                    Type: N Check: 6984

```
   1   gaattcggca cgaggcgcgg cggctgcgac cgggacggcc catttccgc
  51   cagctcgccg ctcgctatgg cgtcgctcac cgtgaaggcc taccttctgg
 101   gcaaggagga cgcggcgcgc gagattcgcc gcttcagctt ctgctgcagc
 151   cccgagcctg aggcggaagc cgaggctgcg gcgggtccgg gaccctgcga
 201   gcggctgctg agccgggtgg ccgccctgtt ccccgcgctg cggcctggcg
 251   gcttccaggc gcactaccgc gatgaggacg gggacttggt tgcctttttcc
 301   agtgacgagg aattgacaat ggccatgtcc tacgtgaagg atgacatctt
 351   ccgaatctac attaaagaga aaaagagtg ccggcgggac caccgcccac
 401   cgtgtgctca ggaggcgccc cgcaacatgg tgcaccccaa tgtgatctgc
 451   gatggctgca atgggcctgt ggtaggaacc cgctacaagt gcagcgtctg
 501   cccagactac gacttgtgta gcgtctgcga gggaaagggc ttgcaccggg
 551   ggcacaccaa gctcgcattc cccagcccct cgggcacct gtctgagggc
 601   ttctcgcaca gccgctggct ccggaaggtg aaacacggac acttcgggtg
 651   gccaggatgg gaaatgggtc caccaggaaa ctggagccca cgtcctcctc
 701   gtgcagggga ggcccgccct ggccccacgg cagaatcagc ttctggtcca
 751   tcggaggatc cgagtgtgaa tttcctgaag aacgttgggg agagtgtggc
 801   agctgccctt agccctctgg gcattgaagt tgatatcgat gtggagcacg
 851   gagggaaaag aagccgcctg accccgtct ctccagagag ttccagcaca
 901   gaggagaaga gcagctcaca gccaagcagc tgctgctctg accccagcaa
 951   gccgggtggg aatgttgagg gcgccacgca gtctctggcg agcagatga
1001   ggaagatcgc cttggagtcc gagggcgcc ctgaggaaca gatggagtcg
1051   gataactgtt caggaggaga tgatgactgg acccatctgt cttcaaaaga
1101   agtggacccg tctacaggtg aactccagtc cctacagatg ccagaatccg
```

FIG. IA

```
1151    aagggccaag ctctctggac ccctcccagg agggacccac agggctgaag
1201    gaagctgcct tgtacccaca tctaccgcca gaggctgacc cgcggctgat
1251    tgagtccctc tcccagatgc tgtccatggg cttctctgat gaaggcggct
1301    ggctcaccag gctcctgcag accaagaact atgacatcgg agcggctctg
1351    gacaccatcc agtattcaaa gcatccccg ccgttgtgac cacttttgcc
1401    cacctcttct gcgtgcccct cttctgtctc atagttgtgt taagcttgcg
1451    tagaattgca ggtctctgta cgggccagtt tctctgcctt cttccaggat
1501    caggggttag ggtgcaagaa gccatttagg gcagcaaaac aagtgacatg
1551    aagggagggt ccctgtgtgt gtgtgtgctg atgtttcctg ggtgccctgg
1601    ctccttgcag cagggctggg cctgcgagac ccaaggctca ctgcagcgcg
1651    ctcctgaccc ctccctgcag gggctacgtt agcagcccag cacatagctt
1701    gcctaatggc tttcactttc tcttttgttt taaatgactc ataggtccct
1751    gacatttagt tgattatttt ctgctacaga cctggtacac tctgatttta
1801    gataaagtaa gcctaggtgt tgtcagcagg caggctgggg aggccagtgt
1851    tgtgggcttc ctgctgggac tgagaaggct cacgaaggc atccgcaatg
1901    ttggtttcac tgagagctgc ctcctggtct cttcaccact gtagttctct
1951    catttccaaa ccatcagctg cttttaaaat aagatctctt tgtagccatc
2001    ctgttaaatt tgtaaacaat ctaattaaat ggcatcagca ctttaaccaa
2051    taaaaaaaa aaaaaaaaa aaaactcgag gga
```

FIG. IB

```
p62.pep   Length: 440                              Type: P    Check: 164

1   MASLTVKAYL  LGKEDAAREI  RRFSFCCSPE  PEAEAEAAAG  PGPCERLLSR
 51   VAALFPALRP  GGFQAHYRDE  DGDLVAFSSD  EELTMAMSYV  KDDIFRIYIK
101   EKKECRRDHR  PPCAQEAPRN  MVHPNVICDG  CNGPVVGTRY  KCSVCPDYDL
151   CSVCEGKGLH  RGHTKLAFPS  PFGHLSEGFS  HSRWLRKVKH  GHFGWPGWEM
201   GPPGNWSPRP  PRAGEARPGP  TAESASGPSE  DPSVNFLKNV  GESVAAALSP
251   LGIEVDIDVE  HGGKRSRLTP  VSPESSSTEE  KSSSQPSSCC  SDPSKPGGNV
301   EGATQSLAEQ  MRKIALESEG  RPEEQMESDN  CSGGDDDWTH  LSSKEVDPST
351   GELQSLQMPE  SEGPSSLDPS  QEGPTGLKEA  ALYPHLPPEA  DPRLIESLSQ
401   MLSMGFSDEG  GWLTRLLQTK  NYDIGAALDT  IQYSKHPPPL
```

FIG. 2 p62daudi.seg  Length: 1977
Check: 2184   ..

```
    1  cgccgcttca gcttctgctt tagcccggag cccgaggccg aagccgaggc
   51  cgcgcctggc ccccggccct gtgagcggct gctgaaccgg gtggctgcgc
  101  tctttcctgt gctccggccc ggcggctttc aggcgcacta ccgcgatgag
  151  gatggggact tggttgcctt ttccagtgac gaggagctga cgatggcgat
  201  gtcatatgtg aaggacgaca tcttccgcat ttacattaaa gagaagaagg
  251  agtgtcggag ggatcagcgc ccctcatgtg cccaggaggt gcccagaaac
  301  atggtgcacc ccaacgtgat ctgtgacggc tgtaacgggc cgtggtggg
  351  gacgcgctac aagtgcagcg tctgccctga ctacgaccta ttctccgcct
  401  gcgagggcaa gggcctgcac cgggaacacg gcaagctggc ttccccagc
  451  cccattgggc acttctctga gggcttctct cacagccgct ggctccggaa
  501  gctgaaacat gggcaatttg ggtggcctgc ctgggacatg gcacaccgg
  551  ggaactggag cccacgtcct cctcaggcag gggatgccca ccctgcccct
  601  gccacggaat cagcctctgg tccatcggaa catcccagtg tgaatttcct
  651  caagaacgta ggggagagtg tggcggctgc cctcaagcct ctagggattg
  701  aagtcgatat tgtagtggaa acgcgaggca agagaagccg cctgaccccc
  751  acctctgcag gcagttccag cacagaggag aagtgtagct ctcagccaag
```

FIG. 3A

```
 801   cagctgctgc tctgacccca gcaagccaga cagggacgtg gagggcacag
 851   cacagtctct gacggagcag atgaataaga tcgccctgga gtcagggggt
 901   cagcatgagg aacagatgga gtctgataac tgttcaggag gagatgatga
 951   ctggactcat ctgtcttcaa aagaggtgga cccgtctaca ggtgaactgc
1001   agtctctaca gatgcctgag tctgaagggc caagctctct ggatggttcc
1051   caggaaggac ccacaggact gaaggaagct gaactgtacc cacatctgcc
1101   accagaagct gaccccggc tgattgagtc cctctcccag atgctgtcca
1151   tggtctctga tgaaggtggc tggctcacca ggcttctgca gaccaagaat
1201   tacgacatcg ggctgccct gaacaccatc cagtattcaa acacccacc
1251   acctttgtga cgatgtttgc tcacccattc tgtgtcccct ttgagttagt
1301   gtagaacccc actgcctcta agtcccaatt tctcgtcatt cttctttcag
1351   aatctggggg gtgggatgc agaaagccct ttagggcagt agaacaagtg
1401   acacgggggg agttccaagg gtgtgagTGC GGATTCTGAG AAAcactgat
1451   cagcttccca tggatgctgg ctccttccag ccaggggacc cgccctggg
1501   gcagagcgag agactcctcg ctggggagga cgtggagacc atactgcatc
1551   ttatccgtac tctccctgca ggattacacc agcagtccag aagagatctt
1601   gccaaatggc tttctgcttt ttctttgtat aggacactga tatgtaactg
1651   attttatgct agaagtttga tatcctctga atttagctaa aggatcacca
1701   gcattcaccc cggggtggaa gaggctgtcc tgtagcaatt acagctcagg
1751   actgtGGCTA ACATCTGAGg aataaagaag gctgacaga ggaactgatg
1801   ctgttcagag tactgcctat tcataacca ctgtagttac cgtttccaaa
1851   cctgtcagct gcttttaaag ttaagaaaat cgctttgtaa ccattctatt
1901   tgtaaacaat tttaattaat taaaggtata agcactttaa tcaaaaaaaa
1951   aaaaaaaaaa ttccaccaca ctggcgg
```

FIG. 3B

```
p62daudi.pep  Length: 420                                      Type: P
Check: 4693     ..

1  RRFSFCFSPE  PEAEAEAAPG  PRPCERLLNR  VAALFPVLRP  GGFQAHYRDE

51  DGDLVAFSSD  EELTMAMSYV  KDDIFRIYIK  EKKECRRDQR  PSCAQEVPRN

101  MVHPNVICDG  CNGPVVGTRY  KCSVCPDYDL  FSACEGKGLH  REHGKLAFPS

151  PIGHFSEGFS  HSRWLRKLKH  GQFGWPAWDM  GTPGNWSPRP  PQAGDAHPAP

201  ATESASGPSE  HPSVNFLKNV  GESVAAALKP  LGIEVDIVVE  TRGKRSRLTP

251  TSAGSSSTEE  KCSSQPSSCC  SDPSKPDRDV  EGTAQSLTEQ  MNKIALESGG

301  QHEEQMESDN  CSGGDDDWTH  LSSKEVDPST  GELQSLQMPE  SEGPSSLDGS

351  QEGPTGLKEA  ELYPHLPPEA  DPRLIESLSQ  MLSMVSDEGG  WLTRLLQTKN

401  YDIGAALNTI  QYSKHPPPL*
```

FIG. 4

127 WFFKNLSRKD AERQLLAPGN THGSFLIRES ESTAGSFSLS VRDFDQNQGE 176
177 VVKHYKIRNL DNGGFYISPR ITFPGLHELV RHYTNASDGL CTRLSRPCQT 226
227 Q

FIG. 5 p62.seg2 x p62daudi.seg

```
101 gcaaggaggacgcggcgcgcgagattcgccgcttcagcttctgctgcagc 150
                                 ||||||||||||||||||| |||
  1 ..............................cgccgcttcagcttctgctttagc 24
151 cccgagcctgaggcggaagccgaggctgcggcgggtccgggaccctgcga 200
    || ||||| ||||| ||||||||||| ||| | || || | ||||| ||
 25 ccggagcccgaggccgaagccgaggccgcgcctggccccggccctgtga 74
201 gcggctgctgagccgggtggccgccctgttccccgcgctgcggcctggcg 250
    |||||||||| |||||||||| || || || | ||| ||||| ||||
 75 gcggctgctgaaccgggtggctgcgctctttcctgtgctccggcccggcg 124
```

FIG. 6A

```
251 gcttccaggcgcactaccgcgatgaggacggggacttggttgccttttcc 300
    |||| |||||||||||||||||||||||| ||||||||||||||||||||
125 gctttcaggcgcactaccgcgatgaggatggggacttggttgccttttcc 174

301 agtgacgaggaattgacaatggccatgtcctacgtgaaggatgacatctt 350
    |||||||||| |||| ||||| ||||| || |||||||| ||||||||||
175 agtgacgaggagctgacgatggcgatgtcatatgtgaaggacgacatctt 224

351 ccgaatctacattaaagagaaaaagagtgccggcgggaccaccgcccac 400
    ||| || |||||||||||||| || ||||| ||| |||| || |||||
225 ccgcatttacattaaagagaagaaggagtgtcggagggatcagcgccct 274

401 cgtgtgctcaggaggcgccccgcaacatggtgcacccaatgtgatctgc 450
    | ||||| |||||||| |||| |||| |||||||||||||| ||||||i
275 catgtgcccaggaggtgcccagaaacatggtgcacccaacgtgatctgt 324

451 gatggctgcaatgggcctgtggtaggaacccgctacaagtgcagcgtctg 500
    || |||||| || ||||| ||||| || || ||||||||||||||||||
325 gacggctgtaacgggcccgtggtggggacgcgctacaagtgcagcgtctg 374

501 cccagactacgacttgtgtagcgtctgcgagggaaagggcttgcaccggg 550
    ||| ||||||||| | | || |||||||||||| |||||| ||||||||
375 ccctgactacgacctattctccgcctgcgagggcaagggcctgcaccggg 424

551 ggcacaccaagctcgcattccccagccccttcgggcacctgtctgagggc 600
    |||   ||||||| || ||||||||||||| |||||| | ||||||||
425 aacacggcaagctggcttttccccagccccattgggcacttctctgagggc 474

601 ttctcgcacagccgctggctccggaaggtgaaacacggacacttcgggtg 650
    ||||| |||||||||||||||||||| ||||||| || || || |||||
475 ttctctcacagccgctggctccggaagctgaaacatgggcaatttgggtg 524

651 gccaggatgggaaatgggtccaccaggaaactggagcccacgtcctcctc 700
    ||| | ||||| ||||   |||| || |||||||||||||||||||||||
525 gcctgcctgggacatgggcacaccggggaactggagcccacgtcctcctc 574

701 gtgcaggggaggcccgccctggccccacggcagaatcagcttctggtcca 750
    |||||||| |||| |||||  |   | |||||||| |||| |||||||||
575 aggcaggggatgcccaccctgccctgccacggaatcagcctctggtcca 624

751 tcggaggatccgagtgtgaatttcctgaagaacgttggggagagtgtggc 800
    ||||    |||| |||||||||||||||||||| || ||||||||||||
625 tcggaacatcccagtgtgaatttcctcaagaacgtaggggagagtgtggc 674

801 agctgccttagccctctgggcattgaagttgatatcgatgtggagcacg 850
    ||||||||  | |||| |||||||||||||| |  ||| | |||||
675 ggctgccctcaagcctctagggattgaagtcgatattgtagtggaacgc 724

851 gagggaaaagaagccgcctgaccccgtctctccagagagttccagcaca 900
    ||||  || |||||||||||||||||  ||| ||||| ||||||||||
725 gaggcaagagaagccgcctgaccccacctctgcaggcagttccagcaca 774

901 gaggagaagagcagctcacagccaagcagctgctgctctgacccagcaa 950
    |||||||| | ||||| |||||||||||||||||||||||||||||||||
```

FIG. 6B

```
 775 gaggagaagtgtagctctcagccaagcagctgctgctctgaccccagcaa  824

951 gccgggtgggaatgttgagggcgccacgcagtctctggcggagcagatga 1000
     ||| |   || | || |||||| |  | |||||||| |||||||||||
 825 gccagacagggacgtggagggcacagcacagtctctgacggagcagatga  874

1001 ggaagatcgccttggagtccgaggggcgccctgaggaacagatggagtcg 1050
     ||||||||| |||||| |  ||| | |||  | | ||||||||||||||
 875 ataagatcgccctggagtcagggggtcagcatgaggaacagatggagtct  924

1051 gataactgttcaggaggagatgatgactggacccatctgtcttcaaaaga 1100
     |||||||||||||||||||||||||||||||  ||||||||||||||||
 925 gataactgttcaggaggagatgatgactggactcatctgtcttcaaaaga  974

1101 agtggacccgtctacaggtgaactccagtccctacagatgccagaatccg 1150
     |||||||||||||||||||||||| ||||| ||||||||||| || || |
 975 ggtggacccgtctacaggtgaactgcagtctctacagatgcctgagtctg 1024

1151 aagggccaagctctctggacccctcccaggagggacccacagggctgaag 1200
     |||||||||||||||||||   |||     |||||| ||||| |||||||
1025 aagggccaagctctctggatggttcccaggaaggacccacaggactgaag 1074

1201 gaagctgccttgtacccacatctaccgccagaggctgacccgcggctgat 1250
     ||||||   |||||||||||||| || ||| ||||||||||| ||||||
1075 gaagctgaactgtacccacatctgccaccagaagctgaccccggctgat  1124

1251 tgagtccctctcccagatgctgtccatgggcttctctgatgaaggcggct 1300
     ||||||||||||||||||||||||||||   |||||||||| || |||
1125 tgagtccctctcccagatgctgtccatgg...tctctgatgaaggtggct 1171

1301 ggctcaccaggctcctgcagaccaagaactatgacatcggagcggctctg 1350
     ||||||||||| ||||||||||||||||| |||||||||| || || |||
1172 ggctcaccaggcttctgcagaccaagaattacgacatcggggctgccctg 1221

1351 gacaccatccagtattcaaagcatcccccgccgttgtgaccacttttgcc 1400
     ||||||||||||||||| || || || ||| | ||||||| | |||||
1222 aacaccatccagtattcaaaacacccaccacctttgtgacgatgtttgct 1271

1401 cacctcttctgctgcccctcttctgtctcatagttgtgttaagcttgcg 1450
     ||||  |||| :| |||                ||  || || | |
1272 cacccattctgtgtcccc.....................tttgagttagtg 1301

1451 tagaattgcaggtctctgtacgggccagtttctctgccttcttc.....c 1495
     |||||  || |  || | |||  |||||| | ||||||
1302 tagaaccca.ctgcctctaagtcccaatttctcgtcattcttctttcag 1350

1496 aggatcagggggttagggtgcaagaagccatttagggcagcaaaacaagtg 1545
     |   | ||||| || |||| |||||||||||| | ||||||||
1351 aatctggggggtggggatgcagaaagccctttagggcagtagaacaagtg 1400

1546 acatgaagggagggtc...cctgtgtgtgtgtgctga........... 1581
     ||| | ||||| |    |||| ||| | ||||
1401 acacggggggagttccaagggtgtgagTGCGGATTCTGAGAAAcactgat 1450
```

FIG. 6C

```
1582 .tgtttcctgggtgccctggctccttgcagcagg..........ctggg 1620
     ||||| |    |||||||||| |||| ||          |||||
1451 cagcttcccatggatgctggctccttccagccaggggaccccgccctggg 1500

1621 cctgcgagacccaaggctcactgcagcg..................c 1649
     ||||| |   |||  ||| ||  ||                     |
1501 gcagagcgagagactcctcgctggggaggacgtggagaccatactgcatc 1550

1650 gctcctgaccctccctgcaggggctacgttagcagcccagcacatagct 1699
     ||  | ||||||||| |||  |||  ||||| |||| | | | ||
1551 ttatccgtactctccctgca.ggattacaccagcagtccagaagagatct 1599

1700 tgcctaatggctttcacttctcttttgttttaaatgactcataggtccc 1749
     |||| |||||||||| || | |||||             ||||| | |
1600 tgccaaatggctttctgcttttctttgt............ataggacac 1637

1750 tgacatttagttgattattttctgctacagacctggtacactctgatttt 1799
     ||| || ||  ||    |||||| ||||||  || || |||||| |||
1638 tgatatgtaactg...attttatgctagaagtttgatatcctctgaattt 1684

1800 agataaagtaagcctaggtgttgtcagcaggcaggctggggaggcc...a 1846
     || |||||  |   | ||  |  |  |  || |  ||  | ||    |
1685 agctaaaggatcaccagcattcaccccggggtggaagaggctgtcctgta 1734

1847 gtgttgtggcttcctgctgggactga.....gaaggctcacgaagggca 1891
     |  |  |||   ||| |||  ||| |||   ||| | | |||||||
1735 gcaattacagctcaggactgtGGCTAACATCTGAGgaataaagaagggct 1784

1892 tccgcaatgttggtttcactgagagctgcctcctggtctcttcaccactg 1941
     | |     ||||  |  |  ||   ||  | |||| | |  ||||||
1785 gacagaggaactgatgctgt.tcagagtactgcctatttcataaccactg 1833

1942 tagttctctcatttccaaaccatcagctgcttttaa....aataagatct 1987
     |||||  |   || | | ||||||||||||||||     ||  | |||
1834 tagtt.accgtttccaaacctgtcagctgcttttaaagttaagaaaatcg 1882

1988 ctttgtagccatcctgttaaatttgtaaacaatctaattaaatggcatca 2037
     |||||| ||||  || ||   |  ||||||||  ||  | ||  |  |
1883 ctttgtaaccattctatttgtaaacaattttaattaatt.aaa.ggtataa 1931

2038 gcactttaaccaataaaaaaaaaaaaaaaaaaaaaaactcgaggga 2083
     ||||||| |||  ||||| ||| |||||||||||||  |  ||  ||
1932 gcactttaatcaaaaa.aaaaaaaaaaaaattccaccacactggcgg 1977
```

FIG. 6D p62.pep x p62daudi.pep

```
  1 MASLTVKAYLLGKEDAAREIRRFSFCCSPEPEAEAEAAAGPGPCERLLSR  50
                    ||||||  ||||||||||||:||  ||||||.|
  1 ..................RRFSFCFSPEPEAEAEAAPGPRPCERLLNR  30

51 VAALFPALRPGGFQAHYRDEDGDLVAFSSDEELTMAMSYVKDDIFRIYIK 100
    ||||||.||||||||||||||||||||||||||||||||||||||||||
 31 VAALFPVLRPGGFQAHYRDEDGDLVAFSSDEELTMAMSYVKDDIFRIYIK  80

101 EKKECRRDHRPPCAQEAPRNMVHPNVICDGCNGPVVGTRYKCSVCPDYDL 150
    ||||||||:||.||||.||||||||||||||||||||||||||||||||
 81 EKKECRRDQRPSCAQEVPRNMVHPNVICDGCNGPVVGTRYKCSVCPDYDL 130

151 CSVCEGKGLHRGHTKLAFPSPFGHLSEGFSHSRWLRKVKHGHFGWPGWEM 200
    |.||||||||:|.|||||||:||:||||||||||||||:|||:||||:|
131 FSACEGKGLHREHGKLAFPSPIGHFSEGFSHSRWLRKLKHGQFGWPAWDM 180

201 GPPGNWSPRPPRAGEARPGPTAESASGPSEDPSVNFLKNVGESVAAALSP 250
    |.|||||||||.||:|:|..||||||||||.||||||||||||||||.|
181 GTPGNWSPRPPQAGDAHPAPATESASGPSEHPSVNFLKNVGESVAAALKP 230

251 LGIEVDIDVEHGGKRSRLTPVSPESSSTEEKSSSQPSSCCSDPSKPGGNV 300
    ||||||| ||   ||||||||.|::|||||||:||||||||||||: :|
231 LGIEVDIVVETRGKRSRLTPTSAGSSSTEEKCSSQPSSCCSDPSKPDRDV 280

301 EGATQSLAEQMRKIALESEGRPEEQMESDNCSGGDDDWTHLSSKEVDPST 350
    ||..|||.|||.||||||:|..|||||||||||||||||||||||||||
281 EGTAQSLTEQMNKIALESGGQHEEQMESDNCSGGDDDWTHLSSKEVDPST 330

351 GELQSLQMPESEGPSSLDPSQEGPTGLKEAALYPHLPPEADPRLIESLSQ 400
    ||||||||||||||||||.||||||||||||.|||||||||||||||||
331 GELQSLQMPESEGPSSLDGSQEGPTGLKEAELYPHLPPEADPRLIESLSQ 380

401 MLSMGFSDEGGWLTRLLQTKNYDIGAALDTIQYSKHPPPL. 440
    ||||.|||||||||||||||||||||||:||||||||||
381 MLSM.VSDEGGWLTRLLQTKNYDIGAALNTIQYSKHPPPL* 420
```

FIG. 7 p160 DNA sequence p160dna  Length: 3901                                Type: N  Check:
3842 ..

```
   1  ggggcagccg ttctgagtgg gccctctgcg ggctccgcgg ctggggttcc
  51  tggcgggacc gggggtctct cggcagtgag ctcgggcccg cggctccgcc
 101  tgctgctgct ggagagtgtt tctggtttgc tgcaacctcg aacgggtct
 151  gccgttgctc cggtgcatcc cccaaaccgc tcggcccac atttgcccgg
 201  gctcatgtgc ctattgcggc tgcatgggtc ggtgggcggg cccagaacc
 251  tttcagctct tggggcattg gtgagtctca gtaatgcacg tctcagttcc
 301  atcaaaactc ggtttgaggg cctgtgtctg ctgtccctgc tggtagggga
 351  gagccccaca gagctattcc agcagcactg tgtgtcttgg cttcggagca
 401  ttcagcaggt gttacagacc caggacccgc tgccacaat ggagctggcc
 451  gtggctgtcc tgagggacct cctccgatat gcagcccagc tgcctgcact
 501  gttccgggac atctccatga ccacctccc tggccttctc acctccctgc
 551  tgggcctcag gccagagtgt gagcagtcag cattggaagg aatgaaggct
 601  tgtatgacct atttccctcg ggcttgtggt tctctcaaag gcaagctggc
 651  ctcattttt ctgtctaggg tggatgcctt gagccctcag ctccaacagt
 701  tggcctgtga gtgttattcc cggctgccct ctttaggggc tggcttttcc
 751  caaggcctga agcacaccga gagctgggag caggagctac acagtctgct
 801  ggcctcactg cacaccctgc tggggcccct gtacgaggga gcagagactg
 851  ctcctgtgca gaatgaaggc cctggggtgg agatgctgct gtcctcagaa
 901  gatggtgatg cccatgtcct tctccagctt cggcagaggt tttcgggact
 951  ggcccgctgc ctagggctca tgctcagctc tgagtttgga gctcccgtgt
1001  ccgtccctgt gcaggaaatc ctggatttca tctgccggac cctcagcgtc
1051  agtagcaaga atattgtaag tgggatttgt catctcttca gagcccttgc
```

FIG. 8A

```
1101  tcaggatacc aggcaaccag gaaagtactg gggacctgag tctccccaaa
1151  cagtgtcatc ctggagtccg tcccagagag cttctacttt tgtccaaata
1201  acatcacttc ctatgtgtcg tgacacagga gcacagtgtc agagtgtagc
1251  aaatgcttcc ttgggggagg gtgaatttgg ggactcagct gagtcattgc
1301  tgagaggccc agccatcctt cttaccttcc atccagggtc tattttagag
1351  gataggggtt tgattttgtt gggagagatg agatcagggg ttgggtttct
1401  tacctatgtg tacatatgta aatggtcatt ccctgtttct gtctctctct
1451  ggctctcact ttcttcctcc actctttatc tctgcccctt ttttctccag
1501  agcttgcatg gagatggtcc ctgcggctgc tgctgctgcc ctctatccac
1551  cttgaaggcc ttggacctgc tgtctgcact catcctcgcg tgtggaagcc
1601  ggctcttgcg ctttgggatc ctgatcggcc gcctgcttcc ccaggtcctc
1651  aattcctgga gcatcggtag agattccctc tctccaggcc aggagaggcc
1701  ttacagcacg gttcggacca aggtgtatgc gatattagag ctgtgggtgc
1751  aggtttgtgg ggcctcggcg gaatgcttc agggaggagc ctctggagag
1801  gccctgctca cccacctgct cagcgacatc tccccgccag ctgatgccct
1851  taagctgcgt agcccgcggg ggagccctga tgggagtttg cagactggga
1901  agcctagcgc ccccaagaag ctaaagctgg atgtggggga agctatggcc
1951  ccgccaagcc accggaaagg ggatagcaat gccaacagcg acgtgtgtcc
2001  ggctgcactc agaggcctca gccggaccat cctcatgtgt gggcctctca
2051  tcaaggagga gactcacagg agactgcatg acctggtcct cccctggtc
2101  atgggtgtac agcagggtga ggtcctaggc agctccccgt acacgagctc
2151  ccctgccgcc gtgaactcta ctgcctgctg ctggcgctgc tgctggcccc
2201  gtctcctcgc tgcccacctc ctcttgcctg tgccctgcaa gccttctccc
2251  tcggccagcg agaagatagc cttgaggtct cctctttctt gctcagaagc
```

FIG. 8B

```
2301  actggtgacc tgtgctgctc tgacccaccc ccgggttcct cccctgcagc
2351  ccatgggccc cacctgcccc acacctgctc cagtcccccct cctgaggccc
2401  catcgccctt cagggcccca ccgttccatc ctccgggccc catgccctca
2451  gtgggctcca tgccctcagc aggccccatg cccttcagca ggccccatgc
2501  cctcagcagg ccctgtgccc tcggagccct ggacctccac cacagccaac
2551  ctcctaggcc ttctgtccag gcctagtgtc tgtcctcccc ggcttcttcc
2601  tggccctgag aaccaccggg caggctcaaa tgaggacccc atccttgccc
2651  ctagtgggac tcccccacct actataccccc cagatgaaac ttttgggggg
2701  agagtgccca gaccagcctt tgtccactat gacaaggagg aggcatctga
2751  tgtggagatc tccttggaaa gtgactctga tgacagcgtg gtgatcgtgc
2801  ccgaggggct tccccccctg ccaccccac caccctcagg tgccacacca
2851  cccctatag cccccactgg gccaccaaca gcctcccctc ctgtgccagc
2901  gaaggaggag cctgaagaac ttcctgcggc cccagggcct ctcccgccgc
2951  ccccacctcc gccgccgcct gttcctggtc ctgtgaccct ccctccaccc
3001  cagttggtcc ctgaagggac tcctggtggg ggaggacccc cagccctgga
3051  agaggatttg acagttatta atatcaacag cagtgatgaa gaggaggagg
3101  aagaaggaga agaggaagaa gaagaagaag aagaagaaga ggaagaagaa
3151  gaagaggaag aagaggaaga ggaggaagac tttgaggaag aggaagagga
3201  tgaagaggaa tattttgaag aggaagaaga ggaggaagaa gagtttgagg
3251  aagaatttga ggaagaagaa ggtgagttag aggaagaaga agaagaggag
3301  gatgaggagg aggaagaaga actggaagag gtggaagacc tggagtttgg
3351  cacagcagga ggggaggtag aagaaggtgc accaccaccc caaccctgc
3401  ctccagctct gcctccccct gagtctcccc caaaggtgca gccagaaccc
3451  gaacccgaac ccgggctgct tttggaagtg gaggagccag ggacggagga
```

FIG. 8C

```
3501  ggagcgtggg gctgacacag ctcccaccct ggcccctgaa gcgctcccct
3551  cccagggaga ggtggagagg aaggggaaa gccctgcggc agggcccct
3601  ccccaggagc ttgttgaaga agagccctct cctcccccaa ccctgttgga
3651  agaggagact gaggatggga gtgacaaggt gcagccccca ccagagacac
3701  ctgcagaaga agagatggag acagagacag aggccgaagc tctccaggaa
3751  aaggagcagg atgacacagc tgccatgctg ccgacttca tcgattgtcc
3801  ccctgatgat gagaagccac cacctcccac agagcctgac tcctagccat
3851  cttctgcacc ccacctcttt gtttccaata aagttatgtc cttaaaaaaa
3901  a
```

FIG. 8D p160.1

Met Glu Leu Ala Val Ala Val Leu Arg Asp Leu Arg Tyr Ala Ala
1                   5                   10                  15

Gln Leu Pro Ala Leu Phe Arg Asp Ile Ser Met Asn His Leu Pro Gly
            20                  25                  30

Leu Leu Thr Ser Leu Leu Gly Leu Arg Pro Glu Cys Glu Gln Ser Ala
        35                  40                  45

Leu Glu Gly Met Lys Ala Cys Met Thr Tyr Phe Pro Arg Ala Cys Gly
    50                  55                  60

Ser Leu Lys Gly Lys Leu Ala Ser Phe Phe Leu Ser Arg Val Asp Ala
65                  70                  75                  80

Leu Ser Pro Gln Leu Gln Gln Leu Ala Cys Glu Cys Tyr Ser Arg Leu
            85                  90                  95

Pro Ser Leu Gly Ala Gly Phe Ser Gln Gly Leu Lys His Thr Glu Ser
        100                 105                 110

Trp Glu Gln Glu Leu His Ser Leu Leu Ala Ser Leu His Thr Leu Leu
    115                 120                 125

Gly Ala Leu Tyr Glu Gly Ala Glu Thr Ala Pro Val Gln Asn Glu Gly
130                 135                 140

FIG. 9A

Pro Gly Val Glu Met Leu Leu Ser Ser Glu Asp Gly Asp Ala His Val
145                 150                 155                 160

Leu Leu Gln Leu Arg Gln Arg Phe Ser Gly Leu Ala Arg Cys Leu Gly
            165                 170                 175

Leu Met Leu Ser Ser Glu Phe Gly Ala Pro Val Ser Val Pro Val Gln
180                 185                 190

Glu Ile Leu Asp Phe Ile Cys Arg Thr Leu Ser Val Ser Ser Lys Asn
            195                 200                 205

Ile Val Ser Gly Ile Cys His Leu Phe Arg Ala Leu Ala Gln Asp Thr
210                 215                 220

Arg Gln Pro Gly Lys Tyr Trp Gly Pro Glu Ser Pro Gln Thr Val Ser
225                 230                 235                 240

Ser Trp Ser Pro Ser Gln Arg Ala Ser Thr Phe Val Gln Ile Thr Ser
            245                 250                 255

Leu Pro Met Cys Arg Asp Thr Gly Ala Gln Cys Gln Ser Val Ala Asn
260                 265                 270

Ala Ser Leu Gly Gly Glu Phe Gly Asp Ser Ala Glu Ser Leu Leu

FIG. 9B

```
Arg Gly Pro Ala Ile Leu Leu Thr Phe His Pro Gly Ser Ile Leu Glu
    290                 295                 300                 320
Asp Arg Gly Leu Ile Leu Gly Glu Met Arg Ser Gly Val Gly Phe
    305                 310                 315                 320
Leu Thr Tyr Val Tyr Ile Cys Lys Trp Ser Phe Pro Val Ser Ser
    325                 330                 335
Leu Trp Leu Ser Leu Ser Ser Ser Thr Leu Tyr Leu Cys Pro Phe Phe
    340                 345                 350
Leu Gln Ser Leu His Gly Asp Gly Pro Cys Gly Cys Cys Cys Pro
    355                 360                 365
Leu Ser Thr Leu Lys Ala Leu Asp Leu Leu Ser Ala Leu Ile Leu Ala
    370                 375                 380
Cys Gly Ser Arg Leu Leu Arg Phe Gly Ile Leu Ile Gly Arg Leu Leu
    385                 390                 395                 400
Pro Gln Val Leu Asn Ser Trp Ser Ile Gly Arg Asp Ser Leu Ser Pro
    405                 410                 415
Gly Gln Glu Arg Pro Tyr Ser Thr Val Arg Thr Lys Val Tyr Ala Ile
    420                 425                 430
```

FIG. 9C

Leu Glu Leu Trp Val Gln Val Cys Gly Ala Ser Ala Gly Met Leu Gln
435                 440                 445

Gly Gly Ala Ser Gly Glu Ala Leu Leu Thr His Leu Leu Ser Asp Ile
450                 455                 460

Ser Pro Pro Ala Asp Ala Leu Lys Leu Arg Ser Pro Arg Gly Ser Pro
465                 470                 475                 480

Asp Gly Ser Leu Gln Thr Gly Lys Pro Ser Ala Pro Lys Lys Leu Lys
485                 490                 495

Leu Asp Val Gly Glu Ala Met Ala Pro Pro Ser His Arg Lys Gly Asp
500                 505                 510

Ser Asn Ala Asn Ser Asp Val Cys Pro Ala Ala Leu Arg Gly Leu Ser
515                 520                 525

Arg Thr Ile Leu Met Cys Gly Pro Leu Ile Lys Glu Glu Thr His Arg
530                 535                 540

Arg Leu His Asp Leu Val Leu Pro Leu Val Met Gly Val Gln Gln Gly
545                 550                 555                 560

Glu Val Leu Gly Ser Ser Pro Tyr Thr Ser Ser Pro Ala Ala Val Asn

FIG. 9D

```
Ser Thr Ala Cys Cys Trp Arg Cys Cys Trp Pro Arg Leu Leu Ala Ala
            580             585             590
His Leu Leu Pro Val Pro Cys Lys Pro Ser Pro Ser Ala Ser Glu
    595             600             605
Lys Ile Ala Leu Arg Ser Pro Leu Ser Cys Ser Glu Ala Leu Val Thr
            610             615             620
Cys Ala Ala Leu Thr His Pro Arg Val Pro Pro Leu Gln Pro Met Gly
            625             630             635             640
Pro Thr Cys Pro Thr Pro Ala Pro Val Pro Val Pro Leu Leu Arg Pro His Arg
            645             650             655
Pro Ser Gly Pro His Arg Ser Ile Leu Arg Ala Pro Cys Pro Gln Trp
            660             665             670
Ala Pro Cys Pro Gln Gln Ala Pro Cys Pro Ser Ala Gly Pro Met Pro
            675             680             685
Ser Ala Gly Pro Val Pro Ser Glu Pro Trp Thr Ser Thr Thr Ala Asn
            690             695             700
Leu Leu Gly Leu Leu Leu Ser Arg Pro Ser Val Cys Pro Pro Arg Leu Leu
            705             710             715             720
```

FIG. 9E

Pro Gly Pro Glu Asn His Arg Ala Gly Ser Asn Glu Asp Pro Ile Leu
                    725                 730                 735

Ala Pro Ser Gly Thr Pro Pro Thr Ile Pro Asp Glu Thr Phe
            740                 745                 750

Gly Gly Arg Val Pro Arg Pro Ala Phe Val His Tyr Asp Lys Glu Glu
            755                 760                 765

Ala Ser Asp Val Glu Ile Ser Leu Glu Ser Asp Ser Asp Ser Val
            770                 775                 780

Val Ile Val Pro Glu Gly Leu Pro Pro Leu Pro Pro Pro Pro Ser
785                 790                 795                 800

Gly Ala Thr Pro Pro Ile Ala Pro Thr Gly Pro Pro Thr Ala Ser
                    805                 810                 815

Pro Pro Val Pro Ala Lys Glu Glu Pro Glu Leu Pro Ala Ala Pro
            820                 825                 830

Gly Pro Leu Pro Pro Pro Pro Pro Pro Pro Val Pro Gly Pro
            835                 840                 845

Val Thr Leu Pro Pro Gln Leu Val Pro Glu Gly Thr Pro Gly Gly

FIG. 9F

```
                                                855        860
                                850
Gly Gly Pro Ala Leu Glu Glu Asp Leu Thr Val Ile Asn Ile Asn
865                 870                 875                 880
Ser Ser Asp Glu Glu Glu Glu Glu Gly Glu Glu Glu Glu Glu Glu
            885                 890                 895
Glu Glu Glu Glu Glu Glu Glu Glu Glu Glu Glu Glu Glu Glu Glu
        900                 905                 910
Glu Asp Phe Glu Glu Glu Glu Asp Glu Glu Glu Tyr Phe Glu Glu
        915                 920                 925
Glu Glu Glu Glu Glu Glu Glu Phe Glu Glu Glu Glu Glu Glu Glu
        930                 935                 940
Gly Glu Leu Glu Glu Glu Glu Glu Glu Glu Asp Glu Glu Glu Glu
945                 950                 955                 960
Glu Leu Glu Glu Val Glu Asp Leu Glu Phe Gly Thr Ala Gly Glu
            965                 970                 975
Val Glu Gly Ala Pro Pro Pro Thr Leu Pro Pro Ala Leu Pro
            980                 985                 990
Pro Pro Glu Ser Pro Pro Lys Val Gln Pro Glu Pro Glu Pro Pro
        995                 1000                1005
```

FIG. 9G

Gly Leu Leu Leu Glu Val Glu Glu Pro Gly Thr Glu Glu Arg Gly
1010                          1015                       1020

Ala Asp Thr Ala Pro Thr Leu Ala Pro Glu Ala Leu Pro Ser Gln Gly
1025                          1030                      1035              1040

Glu Val Glu Arg Glu Gly Glu Ser Pro Ala Ala Gly Pro Pro Pro Gln
1045                          1050                       1055

Glu Leu Val Glu Glu Glu Pro Ser Pro Pro Pro Thr Leu Leu Glu Glu
1060                          1065                       1070

Glu Thr Glu Asp Gly Ser Asp Lys Val Gln Pro Pro Glu Thr Pro
1075                          1080                       1085

Ala Glu Glu Glu Met Glu Thr Glu Thr Glu Ala Glu Ala Leu Gln Glu
1090                          1095                      1100

Lys Gln Asp Asp Thr Ala Ala Met Leu Ala Asp Phe Ile Asp Cys
1105                          1110                      1115              1120

Pro Pro Asp Asp Glu Lys Pro Pro Pro Thr Glu Pro Asp Ser
1125                          1130                       1135

FIG. 9H p160dna-3  Length: 3211                          Type: N  Check:
2308 ..

```
   1  ggggcagccg ttctgagtgg gccctctgcg ggctccgcgg ctggggttcc
  51  tggcgggacc ggggtctct  cggcagtgag ctcgggcccg cggctccgcc
 101  tgctgctgct ggagagtgtt tctggtttgc tgcaacctcg aacggggtct
 151  gccgttgctc cggtgcatcc cccaaaccgc tcggcccac  atttgcccgg
 201  gctcatgtgc ctattgcggc tgcatgggtc ggtgggcggg cccagaacc
 251  tttcagctct tggggcattg gtgagtctca gtaatgcacg tctcagttcc
 301  atcaaaactc ggtttgaggg cctgtgtctg ctgtccctgc tggtagggga
 351  gagccccaca gagctattcc agcagcactg tgtgtcttgg cttcggagca
 401  ttcagcaggt gttacagacc caggaccgc  ctgccacaat ggagctggcc
 451  gtggctgtcc tgagggacct cctccgatat gcagcccagc tgcctgcact
 501  gttccgggac atctccatga ccacctccc  tggccttctc acctccctgc
 551  tgggcctcag ccagagtgt  gagcagtcag cattggaagg aatgaaggct
 601  tgtatgacct atttccctcg ggcttgtggt tctctcaaag gcaagctggc
 651  ctcattttt  ctgtctaggg tggatgcctt gagccctcag ctccaacagt
 701  tggcctgtga gtgttattcc cggctgccct ctttaggggc tggcttttcc
 751  caaggcctga agcacaccga gagctgggag caggagctac acagtctgct
 801  ggcctcactg cacaccctgc tgggggccct gtacgaggga gcagagactg
 851  ctcctgtgca gaatgaaggc cctggggtgg agatgctgct gtcctcagaa
 901  gatggtgatg cccatgtcct tctccagctt cggcagaggt tttcgggact
 951  ggcccgctgc ctagggctca tgctcagctc tgagtttgga gctccgtgt
1001  ccgtccctgt gcaggaaatc ctggatttca tctgccggac cctcagcgtc
1051  agtagcaaga atattagctt gcatggagat ggtccctgcg gctgctgctg
1101  ctgccctcta tccaccttga aggccttgga cctgctgtct gcactcatcc
```

FIG. 10A

```
1151  tcgcgtgtgg aagccggctc ttgcgctttg ggatcctgat cggccgcctg
1201  cttccccagg tcctcaattc ctggagcatc ggtagagatt ccctctctcc
1251  aggccaggag aggccttaca gcacggttcg gaccaaggtg tatgcgatat
1301  tagagctgtg ggtgcaggtt tgtggggcct cggcgggaat gcttcaggga
1351  ggagcctctg gagaggccct gctcacccac ctgctcagcg acatctcccc
1401  gccagctgat gcccttaagc tgcgtagccc gcggggagc cctgatggga
1451  gtttgcagac tgggaagcct agcgccccca agaagctaaa gctggatgtg
1501  ggggaagcta tggccccgcc aagccacctc ctcttgcctg tgccctgcaa
1551  gccttctccc tcggccagcg agaagatagc cttgaggtct cctctttctt
1601  gctcagaagc actggtgacc tgtgctgctc tgacccaccc ccgggttcct
1651  cccctgcagc ccatgggccc cacctgcccc acacctgctc cagtccccct
1701  cctgaggccc catcgccctt cagggcccca ccgttccatc ctccgggccc
1751  catgccctca gtgggctcca tgccctcagc aggccccatg cccttcagca
1801  ggccccatgc cctcagcagg ccctgtgccc tcggagccct ggacctccac
1851  cacagccaac ctcctaggcc ttctgtccag gcctagtgtc tgtcctcccc
1901  ggcttcttcc tggccctgag aaccaccggg caggctcaaa tgaggacccc
1951  atccttgccc ctagtgggac tcccccacct actataccc cagatgaaac
2001  ttttgggggg agagtgccca gaccagcctt tgtccactat gacaaggagg
2051  aggcatctga tgtggagatc tccttggaaa gtgactctga tgacagcgtg
2101  gtgatcgtgc ccgaggggct tccccccctg ccacccccac caccctcagg
2151  tgccacacca cccctatag ccccactgg gccaccaaca gcctcccctc
2201  ctgtgccagc gaaggaggag cctgaagaac ttcctgcggc cccagggcct
2251  ctcccgccgc ccccacctcc gccgccgcct gttcctggtc ctgtgaccct
2301  ccctccaccc cagttggtcc ctgaagggac tcctggtggg ggaggacccc
```

FIG. 10B

```
2351  cagccctgga agaggatttg acagttatta atatcaacag cagtgatgaa
2401  gaggaggagg aagaaggaga agaggaagaa gaagaagaag aagaagaaga
2451  ggaagaagaa gaagaggaag aagaggaaga ggaggaagac tttgaggaag
2501  aggaagagga tgaagaggaa tattttgaag aggaagaaga ggaggaagaa
2551  gagtttgagg aagaatttga ggaagaagaa ggtgagttag aggaagaaga
2601  agaagaggag gatgaggagg aggaagaaga actggaagag gtggaagacc
2651  tggagtttgg cacagcagga ggggaggtag aagaaggtgc accaccaccc
2701  ccaaccctgc ctccagctct gcctccccct gagtctcccc caaaggtgca
2751  gccagaaccc gaacccgaac ccgggctgct tttggaagtg gaggagccag
2801  ggacggagga ggagcgtggg gctgacacag ctcccaccct ggcccctgaa
2851  gcgctccct cccagggaga ggtggagagg gaagggaaa gccctgcggc
2901  agggccccct cccaggagc ttgttgaaga agagccctct cctcccaa
2951  ccctgttgga agaggagact gaggatggga gtgacaaggt gcagccccca
3001  ccagagacac ctgcagaaga agagatggag acagagacag aggccgaagc
3051  tctccaggaa aaggagcagg atgacacagc tgccatgctg ccgacttca
3101  tcgattgtcc ccctgatgat gagaagccac cacctcccac agagcctgac
3151  tcctagccat cttctgcacc ccacctcttt gtttccaata aagttatgtc
3201  cttaaaaaaa a
```

FIG. 10C p160.2

Met Glu Leu Ala Val Ala Val Leu Arg Asp Leu Leu Arg Tyr Ala Ala
1                   5                   10                  15

Gln Leu Pro Ala Leu Phe Arg Asp Ile Ser Met Asn His Leu Pro Gly
            20                  25                  30

Leu Leu Thr Ser Leu Leu Gly Leu Arg Pro Glu Cys Gln Ser Ala
        35                  40                  45

Leu Glu Gly Met Lys Ala Cys Met Thr Tyr Phe Pro Arg Ala Cys Gly
    50                  55                  60

Ser Leu Lys Gly Lys Leu Ala Ser Phe Phe Leu Ser Arg Val Asp Ala
65                  70                  75                  80

Leu Ser Pro Gln Leu Gln Leu Ala Cys Glu Cys Tyr Ser Arg Leu
        85                  90                  95

Pro Ser Leu Gly Ala Gly Phe Ser Gln Gly Leu Lys His Thr Glu Ser
            100                 105                 110

Trp Glu Gln Glu Leu His Ser Leu Leu Ala Ser Leu His Thr Leu Leu
            115                 120                 125

Gly Ala Leu Tyr Glu Gly Ala Glu Thr Ala Pro Val Gln Asn Glu Gly
            130                 135                 140

FIG. IIA

```
Pro Gly Val Glu Met Leu Leu Ser Ser Glu Asp Gly Asp Ala His Val
145                 150                 155                 160

Leu Leu Gln Leu Arg Gln Arg Phe Ser Gly Leu Ala Arg Cys Leu Gly
            165                 170                 175

Leu Met Leu Ser Ser Glu Phe Gly Ala Pro Val Ser Val Pro Val Gln
                180                 185                 190

Glu Ile Leu Asp Phe Ile Cys Arg Thr Leu Ser Val Ser Ser Lys Asn
            195                 200                 205

Ile Ser Leu His Gly Asp Gly Pro Cys Gly Cys Cys Cys Cys Pro Leu
210                 215                 220

Ser Thr Leu Lys Ala Leu Asp Leu Leu Ser Ala Leu Ile Leu Ala Cys
225                 230                 235                 240

Gly Ser Arg Leu Leu Arg Phe Gly Ile Leu Ile Gly Arg Leu Leu Pro
                245                 250                 255

Gln Val Leu Asn Ser Trp Ser Ile Gly Arg Asp Ser Leu Ser Pro Gly
            260                 265                 270
```

FIG. IIB

```
Gln Glu Arg Pro Tyr Ser Thr Val Arg Thr Lys Val Tyr Ala Ile Leu
            275                 280                 285

Glu Leu Trp Val Gln Val Cys Gly Ala Ser Ala Gly Met Leu Gln Gly
            290                 295                 300

Gly Ala Ser Gly Glu Ala Leu Leu Thr His Leu Leu Ser Asp Ile Ser
305                 310                 315                 320

Pro Pro Ala Asp Ala Leu Lys Leu Arg Ser Pro Arg Gly Ser Pro Asp
            325                 330                 335

Gly Ser Leu Gln Thr Gly Lys Pro Ser Ala Pro Lys Lys Leu Lys Leu
            340                 345                 350

Asp Val Gly Glu Ala Met Ala Pro Pro Ser His Leu Leu Leu Pro Val
            355                 360                 365

Pro Cys Lys Pro Ser Pro Ser Ala Ser Glu Lys Ile Ala Leu Arg Ser
            370                 375                 380

Pro Leu Ser Cys Ser Glu Ala Leu Val Thr Cys Ala Ala Leu Thr His
385                 390                 395                 400

Pro Arg Val Pro Pro Leu Gln Pro Met Gly Pro Thr Cys Pro Thr Pro
            405                 410                 415
```

FIG. 11C

Ala Pro Val Pro Leu Leu Arg Pro His Arg Pro Ser Gly Pro His Arg
420                         425                         430

Ser Ile Leu Arg Ala Pro Cys Pro Gln Trp Ala Pro Cys Pro Gln Gln
435                         440                         445

Ala Pro Cys Pro Ser Ala Gly Pro Met Pro Ser Ala Gly Pro Val Pro
450                         455                         460

Ser Glu Pro Trp Thr Ser Thr Thr Ala Asn Leu Leu Gly Leu Leu Ser
465                         470                         475                    480

Arg Pro Ser Val Cys Pro Pro Arg Leu Leu Pro Gly Pro Glu Asn His
485                         490                         495

Arg Ala Gly Ser Asn Glu Asp Pro Ile Leu Ala Pro Ser Gly Thr Pro
500                         505                         510

Pro Pro Thr Ile Pro Pro Asp Glu Thr Phe Gly Gly Arg Val Pro Arg
515                         520                         525

Pro Ala Phe Val His Tyr Asp Lys Glu Glu Ala Ser Asp Val Glu Ile
530                         535                         540

Ser Leu Glu Ser Asp Ser Asp Asp Ser Val Val Ile Val Pro Glu Gly
545                         550                         555                    560

FIG. 11D

Leu Pro Pro Leu Pro Pro Pro Pro Ser Gly Ala Thr Pro Pro Pro
                565                 570                 575

Ile Ala Pro Thr Gly Pro Pro Thr Ala Ser Pro Pro Val Pro Ala Lys
                580                 585                 590

Glu Glu Pro Glu Glu Leu Pro Ala Ala Pro Gly Pro Leu Pro Pro Pro
                595                 600                 605

Pro Pro Pro Pro Val Pro Gly Pro Val Thr Leu Pro Pro Pro
                610                 615                 620

Gln Leu Val Pro Glu Gly Thr Pro Gly Gly Gly Pro Pro Ala Leu
                625                 630                 635                 640

Glu Glu Asp Leu Thr Val Ile Asn Ile Asn Ser Ser Asp Glu Glu Glu
                645                 650                 655

Glu Glu Glu Gly Glu Glu Glu Glu Glu Glu Glu Glu Glu Glu Glu Glu
                660                 665                 670

Glu Glu Glu Glu Glu Glu Glu Glu Glu Glu Glu Asp Phe Glu Glu
                675                 680                 685

Glu Glu Asp Glu Glu Glu Tyr Phe Glu Glu Glu Glu Glu Glu Glu Glu
                690                 695                 700

FIG. IIE

```
Glu Phe Glu Glu Glu Phe Glu Glu Glu Gly Glu Leu Glu Glu Glu
705                 710                 715                 720
Glu Glu Glu Glu Asp Glu Glu Glu Glu Glu Glu Leu Glu Glu Val Glu
                725                 730                 735
Asp Leu Glu Phe Gly Thr Ala Gly Gly Val Glu Gly Ala Pro
        740                 745                 750
Pro Pro Thr Leu Pro Pro Ala Leu Pro Pro Glu Ser Pro Pro
        755                 760                 765
Lys Val Gln Pro Glu Pro Glu Pro Gly Leu Leu Leu Glu Val
        770                 775                 780
Glu Glu Pro Gly Thr Glu Glu Arg Gly Ala Asp Thr Ala Pro Thr
        785                 790                 795             800
Leu Ala Pro Glu Ala Leu Pro Ser Gln Gly Glu Val Glu Arg Glu Gly
                805                 810                 815
Glu Ser Pro Ala Ala Gly Pro Pro Gln Glu Leu Val Glu Glu Glu
                820                 825                 830
Pro Ser Pro Pro Thr Leu Leu Glu Glu Thr Glu Asp Gly Ser
        835                 840                 845
```

FIG. 11F

Asp Lys Val Gln Pro Pro Pro Glu Thr Pro Ala Glu Glu Met Glu
850                 855                 860

Thr Glu Thr Glu Ala Ala Leu Gln Glu Lys Glu Gln Asp Asp Thr
865                 870                 875                 880

Ala Ala Met Leu Ala Asp Phe Ile Asp Cys Pro Pro Asp Asp Glu Lys
885                 890                 895

Pro Pro Pro Thr Glu Pro Asp Ser
900                 905

FIG. 11G 0  1  3  15 (uM)
pY536
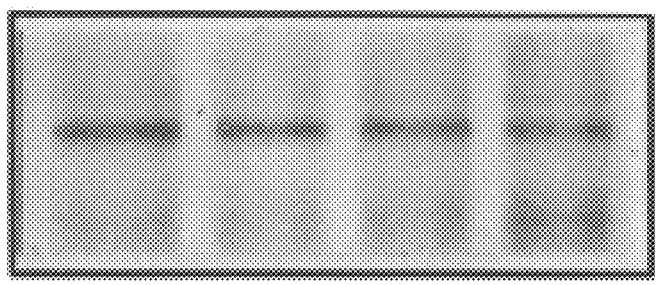
pY771
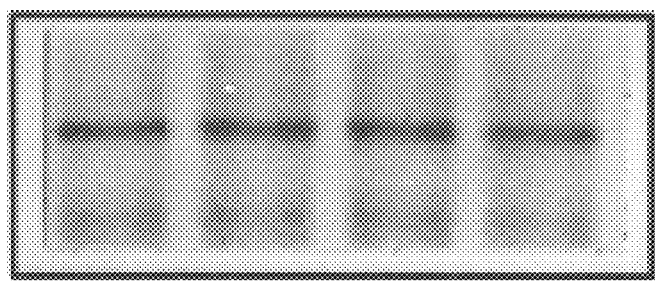
pY324
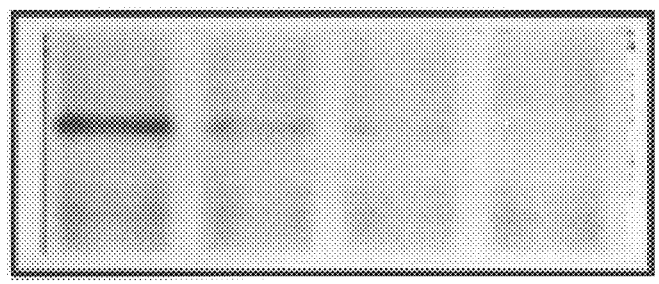
pY505
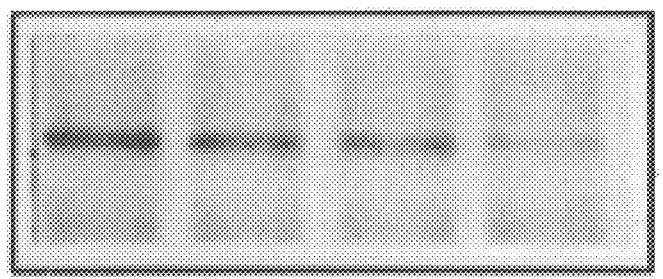
FIG.13

RSRLT PVSPE SSSTE EKSSS QPSS p160dna x p160dna-3

```
  1 ggggcagccgttctgagtgggccctctgcgggctccgcggctggggttcc  50
    ||||||||||||||||||||||||||||||||||||||||||||||||||
  1 ggggcagccgttctgagtgggccctctgcgggctccgcggctggggttcc  50

51 tggcgggaccgggggtctctcggcagtgagctcgggcccgcggctccgcc 100
    ||||||||||||||||||||||||||||||||||||||||||||||||||
 51 tggcgggaccgggggtctctcggcagtgagctcgggcccgcggctccgcc 100

101 tgctgctgctggagagtgtttctggtttgctgcaacctcgaacggggtct 150
    ||||||||||||||||||||||||||||||||||||||||||||||||||
101 tgctgctgctggagagtgtttctggtttgctgcaacctcgaacggggtct 150

151 gccgttgctccggtgcatccccaaaccgctcggccccacatttgcccgg  200
    ||||||||||||||||||||||||||||||||||||||||||||||||||
151 gccgttgctccggtgcatccccaaaccgctcggccccacatttgcccgg  200

201 gctcatgtgcctattgcggctgcatgggtcggtgggcggggcccagaacc 250
    ||||||||||||||||||||||||||||||||||||||||||||||||||
201 gctcatgtgcctattgcggctgcatgggtcggtgggcggggcccagaacc 250

251 tttcagctcttggggcattggtgagtctcagtaatgcacgtctcagttcc 300
    ||||||||||||||||||||||||||||||||||||||||||||||||||
251 tttcagctcttggggcattggtgagtctcagtaatgcacgtctcagttcc 300

301 atcaaaactcggtttgagggcctgtgtctgctgtccctgctggtagggga 350
    ||||||||||||||||||||||||||||||||||||||||||||||||||
301 atcaaaactcggtttgagggcctgtgtctgctgtccctgctggtagggga 350

351 gagccccacagagctattccagcagcactgtgtgtcttggcttcggagca 400
    ||||||||||||||||||||||||||||||||||||||||||||||||||
351 gagccccacagagctattccagcagcactgtgtgtcttggcttcggagca 400

401 ttcagcaggtgttacagacccaggacccgcctgccacaatggagctggcc 450
    ||||||||||||||||||||||||||||||||||||||||||||||||||
401 ttcagcaggtgttacagacccaggacccgcctgccacaatggagctggcc 450
```

FIG. 18A p160dna.pair Page 2

```
451 gtggctgtcctgagggacctcctccgatatgcagcccagctgcctgcact 500
    ||||||||||||||||||||||||||||||||||||||||||||||||||
451 gtggctgtcctgagggacctcctccgatatgcagcccagctgcctgcact 500

501 gttccgggacatctccatgaaccacctccctggccttctcacctccctgc 550
    ||||||||||||||||||||||||||||||||||||||||||||||||||
501 gttccgggacatctccatgaaccacctccctggccttctcacctccctgc 550

551 tgggcctcaggccagagtgtgagcagtcagcattggaaggaatgaaggct 600
    ||||||||||||||||||||||||||||||||||||||||||||||||||
551 tgggcctcaggccagagtgtgagcagtcagcattggaaggaatgaaggct 600

601 tgtatgacctatttccctcgggcttgtggttctctcaaaggcaagctggc 650
    ||||||||||||||||||||||||||||||||||||||||||||||||||
601 tgtatgacctatttccctcgggcttgtggttctctcaaaggcaagctggc 650

651 ctcattttttctgtctaggtggatgccttgagccctcagctccaacagt 700
    ||||||||||||||||||||||||||||||||||||||||||||||||||
651 ctcattttttctgtctaggtggatgccttgagccctcagctccaacagt 700

701 tggcctgtgagtgttattcccggctgccctctttaggggctggcttttcc 750
    ||||||||||||||||||||||||||||||||||||||||||||||||||
701 tggcctgtgagtgttattcccggctgccctctttaggggctggcttttcc 750

751 caaggcctgaagcacaccgagagctgggagcaggagctacacagtctgct 800
    ||||||||||||||||||||||||||||||||||||||||||||||||||
751 caaggcctgaagcacaccgagagctgggagcaggagctacacagtctgct 800

801 ggcctcactgcacaccctgctgggggccctgtacgagggagcagagactg 850
    ||||||||||||||||||||||||||||||||||||||||||||||||||
801 ggcctcactgcacaccctgctgggggccctgtacgagggagcagagactg 850

851 ctcctgtgcagaatgaaggccctggggtggagatgctgctgtcctcagaa 900
    ||||||||||||||||||||||||||||||||||||||||||||||||||
851 ctcctgtgcagaatgaaggccctggggtggagatgctgctgtcctcagaa 900

901 gatggtgatgcccatgtccttctccagcttcggcagaggttttcgggact 950
    ||||||||||||||||||||||||||||||||||||||||||||||||||
901 gatggtgatgcccatgtccttctccagcttcggcagaggttttcgggact 950

951 ggcccgctgcctagggctcatgctcagctctgagtttggagctcccgtgt 1000
    ||||||||||||||||||||||||||||||||||||||||||||||||||
951 ggcccgctgcctagggctcatgctcagctctgagtttggagctcccgtgt 1000

1001 ccgtccctgtgcaggaaatcctggatttcatctgccggaccctcagcgtc 1050
     ||||||||||||||||||||||||||||||||||||||||||||||||||
1001 ccgtccctgtgcaggaaatcctggatttcatctgccggaccctcagcgtc 1050

1051 agtagcaagaatattgtaagtgggatttgtcatctcttcagagcccttgc 1100
     ||||||||||||||
1051 agtagcaagaatatt.................................. 1065

.
                              .

1501 agcttgcatggagatggtccctgcggctgctgctgctgccctctatccac 1550
```

FIG. 18B p160dna.pair Page 3

```
       |||||||||||||||||||||||||||||||||||||||||||||||||
 1066  agcttgcatggagatggtccctgcggctgctgctgctgccctctatccac  1115
 1551  cttgaaggccttggacctgctgtctgcactcatcctcgcgtgtggaagcc  1600
       |||||||||||||||||||||||||||||||||||||||||||||||||
 1116  cttgaaggccttggacctgctgtctgcactcatcctcgcgtgtggaagcc  1165

1601  ggctcttgcgctttgggatcctgatcggccgcctgcttccccaggtcctc  1650
       ||||||||||||||||||||||||||||||||||||||||||||||||||
 1166  ggctcttgcgctttgggatcctgatcggccgcctgcttccccaggtcctc  1215

1651  aattcctggagcatcggtagagattccctctctccaggccaggagaggcc  1700
       ||||||||||||||||||||||||||||||||||||||||||||||||||
 1216  aattcctggagcatcggtagagattccctctctccaggccaggagaggcc  1265

1701  ttacagcacggttcggaccaaggtgtatgcgatattagagctgtgggtgc  1750
       ||||||||||||||||||||||||||||||||||||||||||||||||||
 1266  ttacagcacggttcggaccaaggtgtatgcgatattagagctgtgggtgc  1315

1751  aggtttgtggggcctcggcgggaatgcttcagggaggagcctctggagag  1800
       ||||||||||||||||||||||||||||||||||||||||||||||||||
 1316  aggtttgtggggcctcggcgggaatgcttcagggaggagcctctggagag  1365

1801  gccctgctcacccacctgctcagcgacatctccccgccagctgatgccct  1850
       ||||||||||||||||||||||||||||||||||||||||||||||||||
 1366  gccctgctcacccacctgctcagcgacatctccccgccagctgatgccct  1415

1851  taagctgcgtagcccgcggggagccctgatgggagtttgcagactggga   1900
       ||||||||||||||||||||||||||||||||||||||||||||||||
 1416  taagctgcgtagcccgcggggagccctgatgggagtttgcagactggga   1465

1901  agcctagcgcccccaagaagctaaagctggatgtgggggaagctatggcc  1950
       ||||||||||||||||||||||||||||||||||||||||||||||||||
 1466  agcctagcgcccccaagaagctaaagctggatgtgggggaagctatggcc  1515

1951  ccgccaagccaccggaaagggtgatagcaatgccaacagcgacgtgtgtcc  2000
       ||||||||
 1516  ccgccaag.........................................  1523

2201  gtctcctcgctgcccacctcctcttgcctgtgccctgcaagccttctccc  2250
                  |||||||||||||||||||||||||||||||||||||||
 1524  ..............ccacctcctcttgcctgtgccctgcaagccttctccc  1560

2251  tcggccagcgagaagatagccttgaggtctcctctttcttgctcagaagc  2300
       ||||||||||||||||||||||||||||||||||||||||||||||||||
 1561  tcggccagcgagaagatagccttgaggtctcctctttcttgctcagaagc  1610

2301  actggtgacctgtgctgctctgacccaccccgggttcctcccctgcagc   2350
       ||||||||||||||||||||||||||||||||||||||||||||||||
 1611  actggtgacctgtgctgctctgacccaccccgggttcctcccctgcagc   1660

2351  ccatgggccccacctgccccacacctgctccagtccccctcctgaggccc  2400
       ||||||||||||||||||||||||||||||||||||||||||||||||||
```

FIG. 18C p160dna.pair Page 4

```
1661 ccatgggccccacctgccccacacctgctccagtcccccctcctgaggccc 1710

2401 catcgcccttcagggccccaccgttccatcctccgggcccatgccctca 2450
     ||||||||||||||||||||||||||||||||||||||||||||||||
1711 catcgcccttcagggccccaccgttccatcctccgggcccatgccctca 1760

2451 gtgggctccatgccctcagcaggcccatgcccttcagcaggcccatgc 2500
     ||||||||||||||||||||||||||||||||||||||||||||||||
1761 gtgggctccatgccctcagcaggcccatgcccttcagcaggcccatgc 1810

2501 cctcagcaggccctgtgccctcggagccctggacctccaccacagccaac 2550
     ||||||||||||||||||||||||||||||||||||||||||||||||||
1811 cctcagcaggccctgtgccctcggagccctggacctccaccacagccaac 1860

2551 ctcctaggccttctgtccaggcctagtgtctgtcctccccggcttcttcc 2600
     ||||||||||||||||||||||||||||||||||||||||||||||||||
1861 ctcctaggccttctgtccaggcctagtgtctgtcctccccggcttcttcc 1910

2601 tggccctgagaaccaccgggcaggctcaaatgaggacccatccttgccc 2650
     ||||||||||||||||||||||||||||||||||||||||||||||||
1911 tggccctgagaaccaccgggcaggctcaaatgaggacccatccttgccc 1960

2651 ctagtgggactcccccacctactataccccagatgaaacttttgggggg 2700
     ||||||||||||||||||||||||||||||||||||||||||||||||
1961 ctagtgggactcccccacctactataccccagatgaaacttttgggggg 2010

2701 agagtgcccagaccagcctttgtccactatgacaaggaggaggcatctga 2750
     ||||||||||||||||||||||||||||||||||||||||||||||||||
2011 agagtgcccagaccagcctttgtccactatgacaaggaggaggcatctga 2060

2751 tgtggagatctccttggaaagtgactctgatgacagcgtggtgatcgtgc 2800
     ||||||||||||||||||||||||||||||||||||||||||||||||||
2061 tgtggagatctccttggaaagtgactctgatgacagcgtggtgatcgtgc 2110

2801 ccgaggggcttccccccctgccaccccaccaccctcaggtgccacacca 2850
     ||||||||||||||||||||||||||||||||||||||||||||||||
2111 ccgaggggcttccccccctgccaccccaccaccctcaggtgccacacca 2160

2851 cccctatagcccccactgggccaccaacagcctcccctcctgtgccagc 2900
     ||||||||||||||||||||||||||||||||||||||||||||||||
2161 cccctatagcccccactgggccaccaacagcctcccctcctgtgccagc 2210

2901 gaaggaggagcctgaagaacttcctgcggcccagggcctctcccgccgc 2950
     ||||||||||||||||||||||||||||||||||||||||||||||||
2211 gaaggaggagcctgaagaacttcctgcggcccagggcctctcccgccgc 2260

2951 ccccacctccgccgccgctgttcctggtcctgtgacctccctccaccc 3000
     ||||||||||||||||||||||||||||||||||||||||||||||||
2261 ccccacctccgccgccgctgttcctggtcctgtgacctccctccaccc 2310

3001 cagttggtccctgaagggactcctggtggggaggaccccagccctgga 3050
     ||||||||||||||||||||||||||||||||||||||||||||||||
2311 cagttggtccctgaagggactcctggtggggaggaccccagccctgga 2360

3051 agaggatttgacagttattaatatcaacagcagtgatgaagaggaggagg 3100
     ||||||||||||||||||||||||||||||||||||||||||||||||||
```

FIG. 18D p160dna.pair Page 5

```
2361 agaggatttgacagttattaatatcaacagcagtgatgaagaggaggagg 2410

3101 aagaaggagaagaggaagaagaagaagaagaagaagaagaggaagaagaa 3150
     ||||||||||||||||||||||||||||||||||||||||||||||||||
2411 aagaaggagaagaggaagaagaagaagaagaagaagaagaggaagaagaa 2460

3151 gaagaggaagaagaggaagaggaggaagactttgaggaagaggaagagga 3200
     ||||||||||||||||||||||||||||||||||||||||||||||||||
2461 gaagaggaagaagaggaagaggaggaagactttgaggaagaggaagagga 2510

3201 tgaagaggaatattttgaagaggaagaagaggaggaagaagagtttgagg 3250
     ||||||||||||||||||||||||||||||||||||||||||||||||||
2511 tgaagaggaatattttgaagaggaagaagaggaggaagaagagtttgagg 2560

3251 aagaatttgaggaagaagaaggtgagttagaggaagaagaagaagaggag 3300
     ||||||||||||||||||||||||||||||||||||||||||||||||||
2561 aagaatttgaggaagaagaaggtgagttagaggaagaagaagaagaggag 2610

3301 gatgaggaggaggaagaagaactggaagaggtggaagacctggagtttgg 3350
     ||||||||||||||||||||||||||||||||||||||||||||||||||
2611 gatgaggaggaggaagaagaactggaagaggtggaagacctggagtttgg 2660

3351 cacagcaggaggggaggtagaagaaggtgcaccaccaccccaaccctgc 3400
     ||||||||||||||||||||||||||||||||||||||||||||||||||
2661 cacagcaggaggggaggtagaagaaggtgcaccaccaccccaaccctgc 2710

3401 ctccagctctgcctcccctgagtctcccccaaaggtgcagccagaaccc 3450
     ||||||||||||||||||||||||||||||||||||||||||||||||||
2711 ctccagctctgcctcccctgagtctcccccaaaggtgcagccagaaccc 2760

3451 gaacccgaacccgggctgcttttggaagtggaggagccagggacggagga 3500
     ||||||||||||||||||||||||||||||||||||||||||||||||||
2761 gaacccgaacccgggctgcttttggaagtggaggagccagggacggagga 2810

3501 ggagcgtggggctgacacagctcccaccctggcccctgaagcgctcccct 3550
     ||||||||||||||||||||||||||||||||||||||||||||||||||
2811 ggagcgtggggctgacacagctcccaccctggcccctgaagcgctcccct 2860

3551 cccaggagaggtggagagggaaggggaaagccctgcggcagggcccct 3600
     ||||||||||||||||||||||||||||||||||||||||||||||||||
2861 cccaggagaggtggagagggaaggggaaagccctgcggcagggcccct 2910

3601 ccccaggagcttgttgaagaagagccctctnctcccccaaccctgttgga 3650
     ||||||||||||||||||||||||||||||||||||||||||||||||||
2911 ccccaggagcttgttgaagaagagccctctnctcccccaaccctgttgga 2960

3651 agaggagactgaggatgggagtgacaaggtgcagccccaccagagacac 3700
     ||||||||||||||||||||||||||||||||||||||||||||||||||
2961 agaggagactgaggatgggagtgacaaggtgcagccccaccagagacac 3010

3701 ctgcagaagaagagatggagacagagacagaggccgaagctctccaggaa 3750
     ||||||||||||||||||||||||||||||||||||||||||||||||||
3011 ctgcagaagaagagatggagacagagacagaggccgaagctctccaggaa 3060

3751 aaggagcaggatgacacagctgccatgctggccgacttcatcgattgtcc 3800
     ||||||||||||||||||||||||||||||||||||||||||||||||||
```

FIG. 18E p160dna.pair Page 6

```
3061 aaggagcaggatgacacagctgccatgctggccgacttcatcgattgtcc 3110

3801 ccctgatgatgagaagccaccacctcccacagagcctgactcctagcat 3850
     ||||||||||||||||||||||||||||||||||||||||||||||||
3111 ccctgatgatgagaagccaccacctcccacagagcctgactcctagcat 3160

3851 cttctgcaccccacctctttgtttccaataaagttatgtccttaaaaaaa 3900
     ||||||||||||||||||||||||||||||||||||||||||||||||||
3161 cttctgcaccccacctctttgtttccaataaagttatgtccttaaaaaaa 3210

3901 a 3901
     |
3211 a 3211
```

FIG. 18F p160.1pair Page 1 p160.1 x p160.2

```
  1 MELAVAVLRDLLRYAAQLPALFRDISMNHLPGLLTSLLGLRPECEQSALE  50
    ||||||||||||||||||||||||||||||||||||||||||||||||||
  1 MELAVAVLRDLLRYAAQLPALFRDISMNHLPGLLTSLLGLRPECEQSALE  50

51 GMKACMTYFPRACGSLKGKLASFFLSRVDALSPQLQQLACECYSRLPSLG 100
    ||||||||||||||||||||||||||||||||||||||||||||||||||
 51 GMKACMTYFPRACGSLKGKLASFFLSRVDALSPQLQQLACECYSRLPSLG 100

101 AGFSQGLKHTESWEQELHSLLASLHTLLGALYEGAETAPVQNEGPGVEML 150
    ||||||||||||||||||||||||||||||||||||||||||||||||||
101 AGFSQGLKHTESWEQELHSLLASLHTLLGALYEGAETAPVQNEGPGVEML 150

151 LSSEDGDAHVLLQLRQRFSGLARCLGLMLSSEFGAPVSVPVQEILDFICR 200
    ||||||||||||||||||||||||||||||||||||||||||||||||||
151 LSSEDGDAHVLLQLRQRFSGLARCLGLMLSSEFGAPVSVPVQEILDFICR 200

201 TLSVSSKNIVSGICHLFRALAQDTRQPGKYWGPESPQTVSSWSPSQRAST 250
    ||||||||
201 TLSVSSKNI..........................               209
             ↑
             .
             .
             ↓
351 FFLQSLHGDGPCGCCCCPLSTLKALDLLSALILACGSRLLRFGILIGRLL 400
       ||||||||||||||||||||||||||||||||||||||||||||||
210 ....SLHGDGPCGCCCCPLSTLKALDLLSALILACGSRLLRFGILIGRLL 255

401 PQVLNSWSIGRDSLSPGQERPYSTVRTKVYAILELWVQVCGASAGMLQGG 450
    ||||||||||||||||||||||||||||||||||||||||||||||||||
256 PQVLNSWSIGRDSLSPGQERPYSTVRTKVYAILELWVQVCGASAGMLQGG 305

451 ASGEALLTHLLSDISPPADALKLRSPRGSPDGSLQTGKPSAPKKLKLDVG 500
```

FIG. 19A p160.1pair Page 2

```
           |||||||||||||||||||||||||||||||||||||||||||||||||
 306  ASGEALLTHLLSDISPPADALKLRSPRGSPDGSLQTGKPSAPKKLKLDVG  355

501  EAMAPPSHRKGDSNANSDVCPAALRGLSRTILMCGPLIKEETHRRLHDLV  550
           |||||||
 356  EAMAPPS..........................................  362

551  LPLVMGVQQGEVLGSSPYTSSPAAVNSTACCWRCCWPRLLAAHLLLPVPC  600
                                                |||||||||
 363  .........................................HLLLPVPC  370

601  KPSPSASEKIALRSPLSCSEALVTCAALTHPRVPPLQPMGPTCPTPAPVP  650
      |||||||||||||||||||||||||||||||||||||||||||||||||
 371  KPSPSASEKIALRSPLSCSEALVTCAALTHPRVPPLQPMGPTCPTPAPVP  420

651  LLRPHRPSGPHRSILRAPCPQWAPCPQQAPCPSAGPMPSAGPVPSEPWTS  700
      |||||||||||||||||||||||||||||||||||||||||||||||||
 421  LLRPHRPSGPHRSILRAPCPQWAPCPQQAPCPSAGPMPSAGPVPSEPWTS  470

701  TTANLLGLLSRPSVCPPRLLPGPENHRAGSNEDPILAPSGTPPPTIPPDE  750
      |||||||||||||||||||||||||||||||||||||||||||||||||
 471  TTANLLGLLSRPSVCPPRLLPGPENHRAGSNEDPILAPSGTPPPTIPPDE  520

751  TFGGRVPRPAFVHYDKEEASDVEISLESDSDDSVVIVPEGLPPLPPPPPS  800
      |||||||||||||||||||||||||||||||||||||||||||||||||
 521  TFGGRVPRPAFVHYDKEEASDVEISLESDSDDSVVIVPEGLPPLPPPPPS  570

801  GATPPPIAPTGPPTASPPVPAKEEPEELPAAPGPLPPPPPPPPVPGPVT  850
      |||||||||||||||||||||||||||||||||||||||||||||||||
 571  GATPPPIAPTGPPTASPPVPAKEEPEELPAAPGPLPPPPPPPPVPGPVT  620

851  LPPPQLVPEGTPGGGGPPALEEDLTVININSSDEEEEEGEEEEEEEEEE  900
      |||||||||||||||||||||||||||||||||||||||||||||||||
 621  LPPPQLVPEGTPGGGGPPALEEDLTVININSSDEEEEEGEEEEEEEEEE  670

901  EEEEEEEEEEEEEEDFEEEEEDEEEYFEEEEEEEEEFEEEFEEEEGELEEE  950
      |||||||||||||||||||||||||||||||||||||||||||||||||
 671  EEEEEEEEEEEEEEDFEEEEEDEEEYFEEEEEEEEEFEEEFEEEEGELEEE  720

951  EEEEDEEEEEELEEVEDLEFGTAGGEVEEGAPPPPTLPPALPPPESPPKV  1000
      |||||||||||||||||||||||||||||||||||||||||||||||||
 721  EEEEDEEEEEELEEVEDLEFGTAGGEVEEGAPPPPTLPPALPPPESPPKV  770

1001  QPEPEPEPGLLLEVEEPGTEEERGADTAPTLAPEALPSQGEVEREGESPA  1050
      |||||||||||||||||||||||||||||||||||||||||||||||||
 771  QPEPEPEPGLLLEVEEPGTEEERGADTAPTLAPEALPSQGEVEREGESPA  820

1051  AGPPPQELVEEEPSXPPTLLEEETEDGSDKVQPPPETPAEEEMETETEAE  1100
      |||||||||||||||||||||||||||||||||||||||||||||||||
 821  AGPPPQELVEEEPSXPPTLLEEETEDGSDKVQPPPETPAEEEMETETEAE  870

1101  ALQEKEQDDTAAMLADFIDCPPDDEKPPPPTEPDS  1135
      |||||||||||||||||||||||||||||||||||
 871  ALQEKEQDDTAAMLADFIDCPPDDEKPPPPTEPDS  905
```

FIG. 19B

ISOLATED DNA ENCODING P62 POLYPEPTIDES AND USES THEREFOR

GOVERNMENT FUNDING

Work described herein was supported under grants GM48961, CA47554, and GM20011 awarded by the National Institutes of Health. The U.S. government therefore may have certain rights in this invention.

BACKGROUND OF THE INVENTION

Engagement of the T cell antigen receptor (TCR) by peptide antigen bound to the major histocompatibility complex (MHC) molecules initiates a biochemical cascade involving protein tyrosine kinases (PTKs) and protein tyrosine phosphatases (PTPases). Recent biochemical and genetic evidence has implicated at least three cytoplasmic PTKs, Lck, Fyn, and ZAP-70 that are involved in the initiation of TCR signal transduction. Chan, A. C. et al. (1994) *Annu. Rev. Immunol.* 12:555–592. Lck and Fyn are members of the Src-family (Cooper, J. A. (1989) "The Src Family of Protein Tyrosine Kinases" In Peptides and Protein Phosphorylation ed. Kemp, B. and Alewood, P. F. (CRC Press, Boca Raton) pp. 85–113) and ZAP-70 is a member of the Syk-family. The Src-family PTKs share a number of common structural features including: (1) an N-terminal myristylated glycine at residue 2 that permits membrane localization; (2) a unique approximately 80 amino acid N-terminal region that may dictate specific associations of the kinase; (3) an approximately 60 amino acid Src-homology 3 (SH3) domain involved in interacting with signaling molecules with proline-rich regions (reviewed in Pawson, T. et al. (1992) *Cell* 21:359–362); (4) an approximately 100 amino acid Src-homology 2 (SH2) domain that can specifically mediate the recruitment of tyrosine phosphoproteins (reviewed in Pawson, T. et al. (1992) *Cell* 21:359–362); (5) a C-terminal catalytic domain; and (6) a negative regulatory tyrosine residue C-terminal to the kinase domain. Chan, A. C. et al. (1994) *Annu. Rev. Immunol.* 12:555–592.

Lck is a 56 kDa lymphoid specific PTK that noncovalently associates with the cytoplasmic domains of CD4 and CD8 through cysteine-dependent interactions. Rudd, C. E. et al. (1988) *Proc. Natl. Acad. Sci. USA* 85:5190–5194; Veillette, A. et al. (1988) *Cell* 55:301–308; Turner, J. M. et al. (1990) *Cell* 60:755–765; Shaw, A. S. et al. (1989) *Cell* 59:627–636; Shaw, A. S. et al. (1990) *Mol. Cell Biol.* 10:1853–1862. The extracellular domains of CD4 and CD8 serve as TCR co-receptors by binding the monomorphic regions of MHC class II or I molecules, respectively, to stabilize the interaction between T cells and antigen presenting cells. Doyle, C. et al. (1988) *Nature* 330:256–258; Norment, A. M. et al. (1988) *Nature* 336:79–81. In addition to this stabilizing function, the association of CD4 and CD8 with Lck has also suggested a potential role in signal transduction for these TCR co-receptors. Veillette, A. et al. (1989) *Nature* 338:257–259. Specifically, the association of Lck and CD4 has been shown to be an essential, but not the only, requirement for co-receptor function in TCR signaling. Chan, A. C. et al. (1994) *Annu. Rev. Immunol.* 12:555–592.

Further evidence, in the form of genetic studies, has been derived to demonstrate the importance of Lck in both thymocyte development and TCR-mediated cell signaling. Chan, A. C. et al. (1994) *Annu. Rev. Immunol.* 12:555–592. For example, mice deficient in Lck, as a result of homologous recombination, have a pronounced arrest in thymocyte development with a 10–30 fold decrease in total thymocyte number. Molina, T. J. et al. (1992) *Nature* 357:161–164. Whereas the double-negative ($CD4^-CD8^-$) thymocyte population was similar to normal littermates, there was a dramatic reduction in the double-positive ($CD4^+CD8^+$) thymocyte population (10–60 fold) and no detectable single positive ($CD4^+CD8^-$ and $CD4^-CD8^+$) thymocytes. A marked reduction also occurred in the number of peripheral T cells, though the few peripheral T cells were capable of mounting a diminished proliferative response to antibody-mediated cross-linking of the TCR. Thus, Lck appears to be critical for normal thymocyte development. Chan, A. C. et al. (1994) *Annu. Rev. Immunol.* 12:555–592.

The role of Lck in TCR-mediated signaling is further supported by results from two studies in which loss of a functional Lck protein abrogated TCR-mediated signaling. In the first study, a mutant of the Jurkat leukemic T cell line, J.CaM1.6, lacking a functional Lck PTK failed to mobilize calcium, to induce tyrosine phosphoproteins, or to express activation antigens following TCR stimulation. Straus, D. and Weiss, A. (1992) *Cell* 70:585–593. Reconstitution with wild-type murine Lck in this mutant restored all TCR-mediated functions. In the second study, a spontaneous variant of an IL-2-dependent cytotoxic T cell line lacking Lck also manifested a profound reduction in TCR-mediated cytolysis that was restored following Lck expression. Karnitz, L. et al. (1992) *Mol. Cell Biol.* 12:4521–4530. Both mutants demonstrated comparable levels of Fyn kinase activity relative to their parental counterparts. The fact that normal levels of other Src-family PTKs in these cells are unable to compensate for the Lck deficit demonstrates that Lck plays a critical role in TCR-mediated signal transduction. Chan, A. C. et al. (1994) *Annu. Rev. Immunol.* 12:555–592.

Further studies have yielded results which are consistent with the requirement for Lck in TCR-mediated signaling. Specifically, overexpression of an "activated" form of Lck (F505) in a $CD4^-$ negative murine T cell hybridoma resulted in enhanced antigen-induced IL-2 secretion and TCR-induced cellular tyrosine phosphoproteins. Abraham, N. et al. (1991) *Nature* 350:62–66. In addition, it has been shown through further analysis of the domains within Lck that participate in TCR function that membrane localization and the SH2 domain of Lck are both required. Caron, L. et al. (1992) *Mol. Cell Biol.* 12:2720–2729. Mutation of the N-terminal site of myristylation (thereby preventing membrane localization of Lck(F505)) or deletion of the SH2 domain of Lck(F505) abolished the TCR-induced hyperresponsiveness as indicated by cellular tyrosine phosphorylation and antigen-induced IL-2 production. In contrast, retroviral infection of T helper hybridoma cell lines with a temperature sensitive Lck(F505) resulted in antigen-independent IL-2 production at the permissive temperature. Luo, K. and Sefton, B. M. (1992) *Mol. Cell Biol.* 12:4724–4732. In this system, while deletion of the SH2 domain abrogated antigen-independent IL-2 production, deletion of the SH3 domain did not significantly alter IL-2 production. Thus, the SH2 domain may be required to interact with downstream effector molecules in propagating TCR function. Given the above-described studies, further information about the mechanisms and cellular components which regulate Lck function would offer potential new routes for modulating Lck/TCR-mediated cells signaling and lymphoid cell development and/or function.

SUMMARY OF THE INVENTION

This invention is based, at least in part, on the discovery of a family of polypeptides, designated herein as p62 polypeptides, which share at least two structural/functional properties, at least one of which is relevant to Lck function. The p62 polypeptides include, for example, an SH2 binding domain, e.g., an SH2 binding domain which binds an SH2 domain of Lck independent of phosphotyrosine and a ubiquitin binding domain.

Preferred p62 polypeptides of the present invention include several additional structural/functional domains such as a zinc finger domain, a GTPase binding domain, domains containing phosphorylation sites, a PEST domain, and an SH3 binding domain. p62 polypeptides within the scope of the invention are also characterized functionally by, for example, the ability to modulate T cell activity, e.g., T cell development/differentiation, T cell activation, lymphokine secretion; the ability to modulate B cell activity, e.g., B cell development/differentiation, B cell activation, antibody secretion; the ability to modulate ubiquitin-mediated degradation of cellular proteins; the p62 polypeptide modulates expression of cell cycle dependent kinase inhibitors, e.g., $p21^{cip}$; the ability to bind to at least one polypeptide involved in the ras cell signaling cascade, e.g., p120-GAP; the ability to bind to GTPase; the ability to modulate cell cycle progression; and the ability to modulate cell proliferation.

The present invention also relates to a second family of polypeptides, designated herein as p160 polypeptides. The p160 polypeptides are related functionally to the p62 polypeptides in that the p160 polypeptides bind to the $p62/p56^{lck}$ complex to thereby modulate Lck function in a similar manner as described herein for the p62 polypeptides. The p160 polypeptides activate transcription of a variety of genes upon, for example, activation of p62. The genes which are transcribed in response to p160 activation include those which are involved in T or B cell development/differentiation, T or B cell activation, and production of T or B cell-specific factors, e.g., lymphokines and antibodies, respectively. The p160 polypeptides of the present invention have also been found to be substrates for serine/threonine kinase activity.

Accordingly, this invention pertains to isolated nucleic acid molecules encoding p62 polypeptides. Such nucleic acid molecules (e.g., cDNAs) have a nucleotide sequence encoding a p62 polypeptide (e.g., a human polypeptide) or biologically active portions or fragments thereof, such as a peptide having a p62 activity. In a preferred embodiment, the isolated nucleic acid molecule has a nucleotide sequence shown in FIG. 1, SEQ ID NO:1, or a portion or fragment thereof, or a nucleotide sequence shown in FIG. 3, SEQ ID NO:3, or a portion or fragment thereof. Preferred regions of these nucleotide sequences are the coding regions. Other preferred nucleic acid molecules are those which have at least about 60%, preferably at least about 70%, more preferably at least about 80%, and most preferably at least about 90%, 95%, 97% or 98% or more overall nucleotide sequence identity with a nucleotide sequence shown in FIG. 1, SEQ ID NO:1, or a portion or fragment thereof, or a nucleotide sequence shown in FIG. 3, SEQ ID NO:3, or a portion or fragment thereof. Nucleic acid molecules which hybridize under stringent conditions to the nucleotide sequence shown in FIG. 1, SEQ ID NO:1 or the nucleotide sequence shown in FIG. 3, SEQ ID NO:3 are also within the scope of the invention. Portions or fragments of the nucleic acid molecules of the present invention are also specifically contemplated. Such portions or fragments include nucleotide sequences which encode, for example, polypeptide domains having a p62 activity. Examples of portions or fragments of nucleic acid molecules which encode such domains include portions or fragments of nucleotide sequences of FIG. 1, SEQ ID NO:1 and of FIG. 3, SEQ ID NO:3 which encode one or more of the following: a ubiquitin binding domain; an SH2 binding domain; a zinc finger domain; at least one phosphorylation site; a GTPase binding domain; a PEST domain; and an SH3 domain. Particularly preferred nucleotide sequences encoding each of these domains are described herein.

In another embodiment, the nucleic acid molecules of the invention encode a polypeptide having an amino acid sequence shown in FIG. 2, SEQ ID NO:2, or a portion or fragment thereof having a biological activity, e.g., a p62 activity, or an amino acid sequence shown in FIG. 4, SEQ ID NO:4, or a portion or fragment thereof having a p62 activity. Nucleic acid molecules encoding a polypeptide having at least about 60%, preferably at least about 70%, more preferably at least about 80%, and most preferably at least about 90%, 95%, 97% or 98% overall sequence identity with an amino acid sequence shown in FIG. 2, SEQ ID NO:2, or a portion or fragment thereof having a biological activity, e.g., a p62 activity, or an amino acid sequence shown in FIG. 4, SEQ ID NO:4, or a portion or fragment thereof having a biological activity, e.g., a p62 activity, are also within the scope of the invention.

This invention further pertains to nucleic acid molecules which encode p62 polypeptides which bind to ubiquitin, a ubiquitin analog, derivative or active fragment, and an SH2 domain. In a preferred embodiment, the p62 polypeptides bind an SH2 domain having an amino acid sequence which has at least about 70%, more preferably at least about 80%, and most preferably at least about 90% or more (e.g., 95%, 97% or 98%) sequence identity with an amino acid sequence of the SH2 domain of $p56^{lck}$. In one embodiment, the polypeptide binds to the SH2 domain of $p56^{lck}$ as shown in FIG. 5, SEQ ID NO:5. The p62 polypeptides encoded by the nucleic acids of the present invention can also have one or more, in any combination, of various p62 activities. These activities include (1) the ability to bind to a Lck SH2 domain or Lck related SH2 domain (i.e., an SH2 domain which comprises an amino acid sequence having at least about 70% sequence identity with the amino acid sequence of the SH2 domain of $p56^{lck}$), preferably in a phosphotyrosine (pY)-independent manner; (2) the ability to bind to ubiquitin or a ubiquitin analog, derivative or active fragment thereof; (3) the ability to modulate (e.g., inhibit or stimulate) T cell development (e.g., differentiation) or T cell activation (e.g., lymphokine secretion); (4) the ability to modulate B cell development (e.g., differentiation) or B cell activation (e.g., antibody secretion); (5) the ability to inhibit ubiquitin-mediated degradation of cellular proteins such as cell cycle regulatory proteins (e.g., p53); (6) the ability to modulate expression of cell cycle dependent kinase inhibitors, e.g., $p21^{cip}$; (7) the ability to bind to proteins involved in the ras cell signaling cascade, e.g., p120-GAP; (8) the ability to bind to GTPase; (9) the ability to modulate cell cycle progression, e.g., inhibit or arrest cell cycle progression at, for example, the G1/S boundary; and (10) the ability to modulate (e.g., inhibit or stimulate) cell proliferation.

Another aspect of the invention pertains to nucleic acid molecules which encode polypeptides which are fragments of at least about 20 amino acid residues in length, more preferably at least about 30 amino acid residues in length or more, of an amino acid sequence shown in FIG. 2, SEQ ID NO:2 or an amino acid sequence shown in FIG. 4, SEQ ID NO:4. Other aspects of the invention pertain to nucleic acid molecules which encode polypeptides which are fragments of at least about 20 amino acid residues in length, more preferably at least about 30 amino acid residues in length which have at least about 70%, more preferably at least about 80%, and most preferably at least about 90% or more (e.g., 95%, 97–98%) overall sequence identity with an amino acid sequence shown in FIG. 2, SEQ ID NO:2, or a portion or fragment thereof having a biological activity, e.g., a p62 activity, or an amino acid sequence shown in FIG. 4, SEQ ID NO:4, or a portion or fragment thereof having a biological activity, e.g., a p62 activity. Portions or fragments of the polypeptides encoded by the nucleic acids of the invention include polypeptide regions which comprise, for example, various structural and/or functional domains of p62. Such domains include portions or fragments of nucleotide sequences of FIG. 1, SEQ ID NO:1 and of FIG. 3, SEQ ID NO:3 which encode one or more of the following: a ubiquitin binding domain; an SH2 binding domain; at least one phosphorylation site; a GTPase binding domain; a PEST domain; and an SH3 binding domain. The specific amino acid sequences of each these domains are described herein. Nucleic acid molecules which are antisense to the nucleic acid molecules described herein are also within the scope of the invention.

Another aspect of the invention pertains to recombinant expression vectors containing the nucleic acid molecules of the invention and host cells into which such recombinant expression vectors have been introduced. In one embodiment, such a host cell is used to produce a p62 polypeptide by culturing the host cell in a suitable medium. If desired, a p62 polypeptide protein can be then isolated from the medium or the host cell.

Still another aspect of the invention pertains to isolated p62 polypeptides (e.g., isolated human p62 polypeptides) and active fragments thereof, such as peptides having an activity of a p62 polypeptide (e.g., at least one biological activity of a p62 polypeptide as described herein). The invention also provides an isolated or purified preparation of a p62 polypeptide. In preferred embodiments, a p62 polypeptide comprises an amino acid sequence of FIG. 2, SEQ ID NO:2 or an amino acid sequence of FIG. 4, SEQ ID NO:4. In other embodiments, the isolated p62 polypeptide comprises an amino acid sequence having at least 70%, more preferably 80%, and most preferably 90% (e.g., 95%, 97%–98%) or more overall sequence identity with an amino acid sequence of FIG. 2, SEQ ID NO:2 or an amino acid sequence of FIG. 4, SEQ ID NO:4 and, preferably has an activity of a p62 polypeptide (e.g., at least one biological activity of p62).

This invention also pertains to isolated p62 polypeptides which bind to ubiquitin, a ubiquitin analog, derivative or active fragment, and an SH2 domain. In a preferred embodiment, the p62 polypeptides bind an SH2 domain having an amino acid sequence which is at least about 70%, more preferably at least about 80%, and most preferably at least about 90% or more identical to an amino acid sequence of the SH2 domain of p56$^{lck}$. The binding of the SH2 binding domain to the SH2 domain can be phosphotyrosine independent. In one embodiment, the p62 polypeptides bind to the SH2 domain of p56$^{lck}$ as shown in FIG. 5, SEQ ID NO:5. In other preferred embodiments, the p62 polypeptide domain which binds ubiquitin, a ubiquitin analog, derivative or active fragment which has at least about 50% or more overall sequence identity with an amino acid sequence which includes amino acid residues 323 to 440 of FIG. 2, SEQ ID NO:2 or amino acid residues 303 to 419 of FIG. 4, SEQ ID NO:4. These peptides can optionally include a zinc finger domain, e.g., a zinc finger domain having an amino acid sequence which has at least about 50% or more overall sequence identity with an amino acid sequence which includes amino acid residues 128 to 163 of FIG. 2, SEQ ID NO:2 or an amino acid sequence which includes amino acid residues 108 to 143 of FIG. 4, SEQ ID NO:4 and/or a GTPase binding domain, e.g., a GTPase binding domain having an amino acid sequence which has at least about 50% or more overall sequence identity with an amino acid sequence which includes amino acid residues 66 to 82 of FIG. 2, SEQ ID NO:2 or an amino acid sequence which includes amino acid residues 46 to 62 of FIG. 4, SEQ ID NO:4.

Other optional domains which can be included in the peptides of the present invention include a PEST domain, e.g., a PEST domain having an amino acid sequence which has at least about 50% or more overall sequence identity with an amino acid sequence which includes amino acid residues 266 to 296 of FIG. 2, SEQ ID NO:2 or an amino acid sequence which includes amino acid residues 246 to 276 of FIG. 4, SEQ ID NO:4 and/or an SH3 binding domain, e.g., an SH3 binding domain having an amino acid sequence which has at least about 50% or more overall sequence identity with an amino acid sequence which includes amino acid residues 202 to 211 of FIG. 2, SEQ ID NO:2 or an amino acid sequence which includes amino acid residues 183 to 191 of FIG. 4, SEQ ID NO:4 and an SH3 domain. These isolated p62 polypeptides can have one or more, in any combination, of the p62 biological activities described herein.

Fragments of the p62 polypeptides of the invention can include portions or fragments of the amino acid sequences shown in FIG. 2, SEQ ID NO:2 or FIG. 4, SEQ ID NO:4 which are at least about 20 amino acid residues, at least about 30, or at least about 40 or more amino acid residues in length. The peptide fragments preferably have a p62 activity and can be modified to impart desired characteristics thereon. For example, peptide fragments having a p62 activity can be modified for such purposes as increasing solubility, enhancing therapeutic or prophylactic efficacy, or stability (e.g., shelf life ex vivo and resistance to proteolytic degradation in vivo). Such modified peptides are considered functional equivalents of peptides having an activity of p62 as defined herein. A modified peptide can be produced in which the amino acid sequence has been altered, such as by amino acid substitution, deletion, or addition, to modify a p62 activity, or to which a component has been added for the same purpose. The p62 polypeptide portions or fragments described herein can have a p62 activity, e.g., one or more, in any combination, of the p62 biological activities described herein. Portions or fragments of the polypeptides of the invention can include polypeptide regions which comprise, for example, various structural and/or functional domains. Such domains include portions or fragments of amino acid sequences of FIG. 2, SEQ ID NO:2 and of FIG. 4, SEQ ID NO:4 which encode at least one of the following: a ubiquitin binding domain; an SH2 binding domain; a zinc finger domain; at least one phosphorylation site; a GTPase binding domain; a PEST domain; and an SH3 binding domain. Preferred amino acid sequences of each of these domains are described herein.

The invention also provides for a p62 fusion polypeptide comprising a p62 polypeptide and a second polypeptide portion having an amino acid sequence from a protein unrelated to an amino acid sequence selected from the group consisting of an amino acid sequence shown in FIG. 2, SEQ ID NO:2 and an amino acid sequence shown in FIG. 4, SEQ ID NO:4. In addition, a p62 polypeptide of the invention can be incorporated into a pharmaceutical composition which includes the polypeptide (or active portion thereof) and a pharmaceutically acceptable carrier. In addition, vaccine compositions which include a p62 polypeptide or a vector containing a nucleic acid molecule which encodes a p62 polypeptide are also within the scope of the invention. Antibodies, e.g., monoclonal or polyclonal antibodies, which bind to a p62 polypeptide or fragment thereof are also specifically contemplated in the present invention.

The p62 polypeptides of the invention can be used to modulate, for example, leukocyte proliferation and/or activity in vitro or in vivo. In one embodiment, the invention provides a method for inhibiting cell proliferation in a subject, e.g., a mammal, e.g., a human. This method includes administering to the subject a therapeutically effective amount of an agent which modulates p62 expression such that p62 expression is stimulated. Agents which modulate p62 expression can be used to inhibit cell proliferation which is, for example, associated with tumor formation and growth (i.e., neoplasia), e.g., cervical cancer, e.g., cervical cancer induced by human papilloma virus (HPV), e.g., HPV-1, HPV-2, HPV-3, HPV-4, HPV-5, HPV-6, HPV-7, HPV-8, HPV-9, HPV-10, HPV-11, HPV-12, HPV-14, HPV-13, HPV-15, HPV-16, HPV-17 or HPV-18, and particularly high-risk HPVs, such as HPV-16, HPV-18, HPV-31 and HPV-33. Additional methods for inhibiting cell proliferation in a subject which are within the scope of the invention include administration to the subject of a therapeutically amount of a p62 polypeptide or fragment thereof or a vector comprising a nucleic acid molecule encoding a p62 polypeptide or fragment thereof. In another embodiment, the invention provides a method for promoting cell proliferation in a subject, e.g., a mammal, e.g., a human. This method can include administering to the subject a therapeutically effective amount of an agent which modulates p62 expression such that p62 expression is inhibited. Agents which modulate p62 expression can be used to promote cell proliferation in desired locations and in desired circumstances, e.g., to promote wound healing (e.g., skin cell growth) or hair growth. Other methods for promoting cell proliferation in a subject which are within the scope of the invention include administration to the subject of a therapeutically effective amount of an inhibitor of a p62 polypeptide such as a nucleic acid molecule which is antisense to a nucleic acid molecule encoding a p62 polypeptide or an antibody which binds a p62 polypeptide.

The invention further provides methods for modulating T cell activity, e.g., T cell proliferation, differentiation, cytokine secretion, or B cell activity, e.g., B cell proliferation, differentiation, antibody secretion, in a subject comprising administering to the subject a therapeutically effective amount of an agent which modulates p62 expression, or a therapeutically effective amount of an agent which activates or inhibits a p62 polypeptide.

Additional methods of the invention include assays for identifying agents which inhibit or activate/stimulate a p62 polypeptide. Inhibitory or stimulatory agents identified according to these methods are within the scope of the invention. In one embodiment, for example, an agent which inhibits a p62 polypeptide can be identified by contacting a first polypeptide comprising an SH2 domain of p56$^{lck}$ with a second polypeptide comprising a p62 polypeptide and an agent to be tested and then determining binding of the second polypeptide to the first polypeptide. Inhibition of binding of the first polypeptide to the second polypeptide indicates that the agent is an inhibitor of a p62 polypeptide while activation of binding of the first polypeptide to the second polypeptide indicates that the agent is an activator of a p62 polypeptide.

Alternative methods for identifying an agent which inhibits or activates/stimulates a p62 polypeptide are also within the scope of the invention. For example, an alternative method for identifying an agent which inhibits or activates a p62 polypeptide includes contacting a p53 protein, p53 analog, derivative or active fragment, under conditions which promote ubiquitination of the p53 protein, p53 analog, derivative or active fragment, with an agent to be tested and then determining p53 ubiquitination level in the presence of the agent. Activation of p53 ubiquitination indicates that the agent is an inhibitor of a p62 polypeptide while inhibition of p53 ubiquitination indicates that the agent is an activator/stimulator of a p62 polypeptide.

Other alternative methods for identifying an agent which inhibits or activates/stimulates a p62 polypeptide are contemplated by the present invention. These methods include contacting a first polypeptide comprising ubiquitin, a ubiquitin analog, derivative or active fragment, with a second polypeptide comprising a p62 polypeptide and an agent to be tested and then determining binding of the second polypeptide to the first polypeptide. Inhibition of binding of the first polypeptide to the second polypeptide indicates that the agent is an inhibitor of a p62 polypeptide while activation/ stimulation of binding of the first polypeptide to the second polypeptide indicates that the agent is an activator/stimulator or a p62 polypeptide.

Still other alternative methods for identifying an agent which inhibits or activates/stimulates a p62 polypeptide are provided by the present invention. For example, another method for identifying an agent which inhibits a p62 polypeptide includes contacting a first polypeptide comprising p53 protein, p53 analog, derivative or active fragment, with a second polypeptide comprising a p62 polypeptide and an agent to be tested and then measuring the level of p53 degradation in the presence of the agent. If a comparison of the level of p53 degradation in the presence of the agent to the level of p53 degradation in the absence of the agent shows an increase in the level of p53 degradation in the presence of the agent, the agent is an inhibitor of a p62 polypeptide. If a comparison of the level of p53 degradation in the presence of the agent to the level of p53 degradation in the absence of the agent shows a decrease in the level of p53 degradation in the presence of the agent, the agent is an activator/stimulator of a p62 polypeptide.

Another aspect of the invention includes an isolated nucleic acid molecule comprising a nucleotide sequence encoding a p160 polypeptide. In a preferred embodiment, the nucleic acid sequence encoding a p160 polypeptide comprises a nucleotide sequence shown in FIG. 8, SEQ ID NO:6 or in FIG. 10, SEQ ID NO:7 or a nucleotide sequence encoding an amino acid sequence shown in FIG. 9, SEQ ID NO:8 or FIG. 11, SEQ ID NO:9.

Other aspects of the invention include isolated polypeptides having a p160 activity. Examples of such polypeptides include polypeptides having an amino acid sequence shown in FIG. 9, SEQ ID NO:8 or FIG. 11, SEQ ID NO:9 or a fragment thereof.

Still further aspects of the invention pertain to methods for modulating T cell activity, e.g., T cell proliferation, differentiation, cytokine secretion, or B cell activity, e.g., B cell proliferation, differentiation, antibody secretion, in a subject. These methods include administering to the subject a therapeutically effective amount of an agent which modulates p160 expression, or a therapeutically effective amount of an agent which activates or inhibits a p160 polypeptide. Also specifically contemplated by the present invention are methods for identifying agents which inhibit or activate/ stimulate p160 polypeptides. These methods include steps which are parallel to those described herein for methods of identifying agents which inhibit or activate/stimulate p160 polypeptides. Moreover, as the p160 polypeptides of the present invention are involved in the p62 cellular regulatory activities described herein, the p160 polypeptides have similar applications and uses as the p62 polypeptides.

BRIEF DESCRIPTION OF THE DRAWINGS

FIGS. 1A–1B is the nucleotide sequence of an approximately 2.1 kb (2083 bp) cDNA encoding a first full length human p62 polypeptide (SEQ ID NO:1).

FIG. 2 is the predicted full length amino acid sequence (440 amino acid residues) of the human p62 polypeptide (SEQ ID NO:2) encoded by the nucleotide sequence shown in FIG. 1.

FIGS. 3A–3B is the nucleotide sequence of an approximately 2.0 kb (1977 bp) cDNA encoding a second human p62 polypeptide (SEQ ID NO:3).

FIG. 4 is the predicted amino acid sequence (419 amino acid residues) of the human p62 polypeptide (SEQ ID NO:4) encoded by the nucleotide sequence shown in FIG. 3.

FIG. 5 is the amino acid sequence of the SH2 domain of $p56^{lck}$ (SEQ ID NO:5).

FIGS. 6A–6D is the nucleotide sequence (beginning at nucleotide 101 of SEQ ID NO:1) encoding the first full length human p62 (top) aligned for comparison to the nucleotide sequence (SEQ ID NO:3) encoding the second human p62 polypeptide (bottom). The regions of identity are marked by lines connecting the identical nucleotides.

FIG. 7 is the amino acid sequence (SEQ ID NO:2) encoding the first full length human p62 (top) aligned for comparison to the amino acid sequence (SEQ ID NO:4) encoding the second human p62 polypeptide (bottom). The regions of identity are marked by lines connecting the identical amino acid residues.

FIGS. 8A–8D is the nucleotide sequence of an approximately 3.9 kb (3901 bp) cDNA encoding a first full length human p160 polypeptide (p160.1) (SEQ ID NO:6).

FIGS. 9A–9H is the predicted full length amino acid sequence (1135 amino acid residues) of the first human p160 polypeptide (p160.1) (SEQ ID NO:7) encoded by the nucleotide sequence shown in FIG. 8.

FIGS. 10A–10C is the nucleotide sequence of an approximately 3.2 kb (3211 bp) cDNA encoding a second full length human p160 polypeptide (p160.2) (SEQ ID NO:8).

FIGS. 11A–11C is the predicted full length amino acid sequence (905 amino acid residues) of the second human p160 polypeptide (p160.2) (SEQ ID NO:9) encoded by the nucleotide sequence shown in FIG. 10.

FIG. 12A is a schematic representation of the construction of glutathione S-transferase (GST)-fusion proteins containing regions of $p56^{lck}$. FIG. 12B is an autoradiograph of a 9% SDS-PAGE on which lysates from $^{35}$S-methionine labelled HeLa cells incubated with GST and GST fusion proteins containing unique N-terminal region (1–77), unique N-terminal region and SH3 domain (1–123), and SH2 domain (119–224) were separated. A 62 kD protein (p62) that bound specifically to the SH2 domain is marked with an arrow. FIG. 12C is a photograph of an SDS-PAGE on which lysates from $^{35}$S-methionine labelled HeLa cells (which were lysed in the presence or absence of phosphatase inhibitors (NaVO$_4$ and NaF), protease inhibitors (PMSF and Leupeptin), or reducing reagent (DTT)) incubated with GST.119–224 were analyzed.

FIG. 13 depicts the results of experiments demonstrating that the phosphotyrosine independent binding of p62 to the $p_{56}^{lck}$ SH2 domain is competed by specific phosphotyrosyl peptides. FIG. 13 is an autoradiograph of a 9% SDS-PAGE on which lysates from $^{35}$S-methionine labelled HeLa cells (which were lysed in the presence of phosphatase inhibitors (NaVO$_4$ and NaF)) incubated with increasing concentrations of phosphotyrosyl peptides (pY324, pY505, pY771, and pY536) were separated.

FIG. 14A is a photograph of an immunoblot on which GST alone, GST.119–224, and GST.119–224.R154K incubated with v-src transfected HeLa cell lysate in the presence of phosphatase inhibitor were analyzed using an anti-phosphotyrosine antibody. FIG. 14B is a photograph of an SDS-PAGE on which GST alone, GST.119–224, and GST.119–224.R154K incubated with $^{35}$S-methionine labeled HeLa cell lysate in the presence of phosphatase inhibitors were analyzed. Competition of p62 binding to the SH2 domain by phosphotyrosyl peptide was measured by adding 10 mM pY324 peptide in the incubation mixture.

FIG. 15A is an autoradiograph of an SDS-PAGE on which HeLa cell lysates (from HeLa cells transfected with v-src or vector alone, labelled with $^{35}$S-methionine, and lysed in the presence or absence of phosphatase inhibitors) incubated with GST alone, GST.119–224, and GST.53–224 were analyzed. Samples that were lysed in the absence of phosphatase inhibitors were treated with exogenous recombinant phosphatase mixture (recombinant catalytic fragments of the tyrosine phosphatases LAR, CD45, and SHPTP-1). FIG. 15B shows the same membrane as in FIG. 15A but which was immunoblotted with anti-phosphotyrosine antibody. p62 and two phosphotyrosyl proteins (pp70 and pp80) are marked. FIG. 15C is an autoradiograph on which HeLa cell lysates (from HeLa cells labelled with $^{35}$S-methionine and lysed in the absence of phosphatase inhibitors) incubated with GST alone, GST.119–224, GST.65–224, and GST.53–224.S59E were analyzed. This autoradiograph shows that truncation of the Ser59 region or mutation of Ser59 to Glu59 restores p62 binding to the SH2 domain.

FIG. 16A is an autoradiograph of an SDS-PAGE on which HeLa cell lysates (from HeLa cells labelled with $^{35}$S-methionine and lysed in the presence or absence of phosphatase inhibitors) incubated with GST alone or with GST.119–224 and immunoprecipitated by ras-GAP were analyzed. A protein that comigrates with p62 is coimmunoprecipitated by ras-GAP. FIGS. 16B is autoradiograph of an SDS-PAGE and FIG. 16C is a photograph of an SDS-PAGE stained with Coomassie blue on which the HeLa cell lysates described above were immunoprecipitated with anti-GAP antibody or with a preimmune serum. Recombinant p62 GAP binding protein (rp62$^{GAPbp}$) was run on SDS-PAGE along with GST.119–224 and ras-GAP binding proteins of FIG. 15A. The prominent bands in FIG. 16C are rp62$^{GAPbp}$ (lane 1), antibody (lane 2), and fusion protein (lane 3). FIG. 16D is an autoradiograph of an SDS-PAGE on which V8 partial digestions of p62 bound to GST.119–224 and ras-GAP were analyzed. FIG. 16E depicts the amino acid sequence of a Lys-C digested peptide of purified p62.

FIG. 17A is an autoradiograph of an SDS-PAGE on which HeLa cell lysates (from HeLa cells labelled with $^{35}$S-methionine and lysed in the presence or absence of phosphatase inhibitors and competing peptide pY324) incubated with GST alone or with GST.119–224 were analyzed (lanes 2, 4, 6, and 8). Kinase activity was also measured by incubating the bound proteins with kinase buffer and $^{32}$P-g-ATP (lanes 1, 3, 5, and 7). FIG. 17B is an autoradiograph of an SDS-PAGE on which phosphorylation of myelin basic protein (MBP), incubated with sample aliquots from FIG. 17A, lanes 2, 4, 6, and 8, kinase buffer, and $^{32}$P-g-ATP, was visualized. FIG. 17C is an autoradiograph of an SDS-PAGE on which MBP kinase activity (lane 1) was sequentially eluted with competing pY324 peptide (lane 2) and then with glutathione (lane 3) from glutathione-agarose bound to GST.119–224 and its associated proteins (part of the sample shown in FIG. 17A, lane 6, was used). FIG. 17D is a phospho-amino acid analysis of phosphorylated MBP of FIG. 17B. FIG. 17E is an autoradiograph of an MBP-containing gel on which GST and GST.119–224 bound proteins in HeLa cell lysates, prepared in the absence of NaVO$_4$ as described (lanes 1 and 2 respectively) eluted either with NaVO$_4$ (lane 3) or with pY324 peptide (lane 4) were separated and subjected to kinase assay (Tobe, K. et al. (1992) *J. Biol. Chem.* 267:21089–21097). For a positive control, 0.5 mg of purified p44.erk1 (UBI) was used (lane 5). A sample of an in vitro kinase assay as described in (FIG. 17A), lane 5, was separately run on a SDS-PAGE (lane 6) and compared with in-gel kinase assay.

FIGS. 18A–18F is the nucleotide sequence (SEQ ID NO:6) encoding the first full length human p160 (p160.1) (top) aligned for comparison to the nucleotide sequence (SEQ ID NO:8) encoding the second full length human p160 polypeptide (p160.2) (bottom). The regions of identity are marked by lines connecting the identical nucleotides.

FIGS. 19A–19B is the amino acid sequence (SEQ ID NO:7) encoding the first full length human p160 (p160.1) (top) aligned for comparison to the amino acid sequence (SEQ ID NO:9) encoding the second human p160 polypeptide (p160.2) (bottom). The regions of identity are marked by lines connecting the identical amino acid residues.

DETAILED DESCRIPTION OF THE INVENTION

Figure 12A:
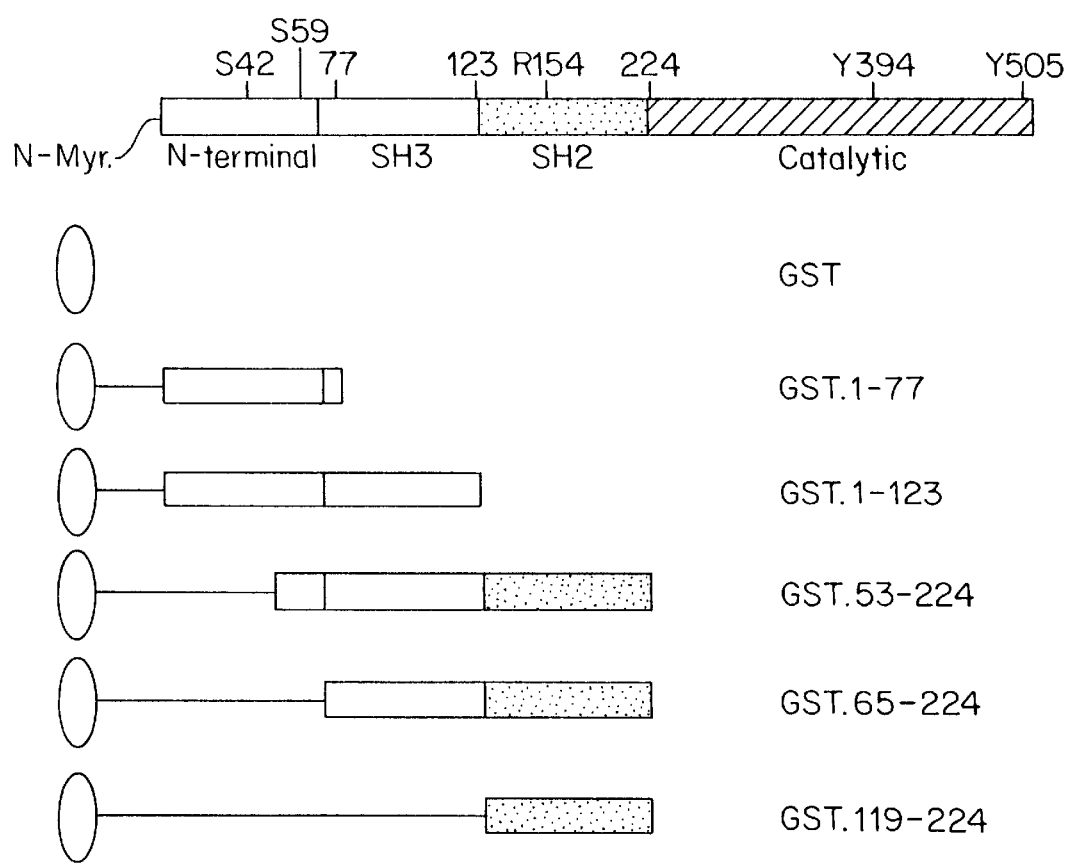
FIGS. 12A–12C depict the results of experiments demonstrating that p62 binds to the Lck SH2 domain in a phosphotyrosine independent manner.

The present invention pertains to the family of novel p62 polypeptides, or active portions thereof which are capable of, for example, modulating T or B cell development (e.g., T or B cell differentiation) and/or T or B cell activation by, for example, modulation of Lck activity. The p62 polypeptides of the invention are also capable of modulating degradation of cellular proteins, e.g., cell cycle regulatory proteins, stimulating expression of cell cycle dependent kinase inhibitors, and arresting cell cycle progression at specific boundaries, to thereby modulate cell proliferation, e.g., cell proliferation associated with tumor formation and growth. Other activities of the p62 polypeptides of the invention are described herein.

Particularly preferred p62 polypeptides are human polypeptides. The complete nucleotide (2083 nucleotides shown in FIG. 1, SEQ ID NO:1) and amino acid sequence (440 amino acids shown in FIG. 2, SEQ ID NO:2) of a first member of the p62 polypeptide family are disclosed herein. A plasmid containing the full length nucleotide sequence encoding this first p62 polypeptide was deposited with the American Type Culture Collection (ATCC) 10801 University Boulevard, Manassas, Va. 20110-2209 on Dec. 19, 1995 and was assigned ATCC Accession Number 97387. This first p62 polypeptide family member is a human cytoplasmic polypeptide with a molecular weight of about 62 kD and is expressed in a variety of tissues including heart, brain, placenta, lung, liver, skeletal muscle, kidney, and pancreas. The mRNA which encodes this polypeptide includes about 2 kb. This p62 polypeptide includes several defined domains. The N-terminal 50 amino acids (amino acid residues 1–50 of the amino acid sequence of FIG. 2, SEQ ID NO:2, which are encoded by nucleotides 67–216 of the nucleotide sequence of FIG. 1, SEQ ID NO:1) of the p62 polypeptide comprise an SH2 binding domain, e.g., an SH2 binding domain which does not include phosphotyrosine. A rac GTPase binding motif appears at amino acid residues 66–82 of FIG. 2, SEQ ID NO:2 (which are encoded by nucleotides 262–312 as shown in FIG. 1, SEQ ID NO:1) of the first p62 polypeptide. The rac GTPase binding motif can be compared as follows to the proposed consensus sequence for rac GTPase set forth in Zhou et al. ((1995) *J. Biol. Chem.* 270:12665–12669) which also appears in human MEK5, scd1 (see also Chang et al. (1994) *Cell* 79:131–141), and cdc24 (see also Miyamoto et al. (1991) *Biochem. Biophys. Res. Commun.* 181:604–610):

| PROTEIN | RAC GTPase CONSENSUS SEQUENCE |
|---|---|
| p62 | 66 HYRDEDGDLVAFSSDEE 82 |
| MEK5 | 61 EYEDEDGDRITVRSDEE 77 |
| scd1 | 786 KYVDEDGDFITITSDED 802 |
| cdc24 | 696 KYQDEDGDFVVLGSDED 715 |

The first p62 polypeptide also includes a zinc finger domain which comprises amino acid residues 128–163 of FIG. 2, SEQ ID NO:2, which are encoded by nucleotides 448–555 of FIG. 1, SEQ ID NO:1. In addition, an SH3 binding domain appears at amino acid residues 202–211 (encoded by nucleotides 670–699 of FIG. 1, SEQ ID NO:1) and a proline-glutamic acid-serine-threonine (PEST) rich motif appears at amino acid residues 266–294 (encoded by nucleotides 862–954 of FIG. 1, SEQ ID NO:1). The presence of PEST motifs are typically associated with rapid degradation of the polypeptide which contains the motif. The first p62 polypeptide family member also includes at least two phosphorylation sites at threonine 269 of the amino acid sequence of FIG. 2, SEQ ID NO:2 (encoded by nucleotides 871–873 of the nucleotide sequence shown in FIG. 1, SEQ ID NO:1) and at serine 272 of the amino acid sequence shown in FIG. 2, SEQ ID NO:2 (encoded by nucleotides 880–882 of the nucleotide sequence shown in FIG. 1, SEQ ID NO:1). The C-terminus of the first p62 polypeptide includes an amino acid sequence comprising amino acid residues 323 to 440 of the amino acid sequence shown in FIG. 2, SEQ ID NO:2 (encoded by nucleotides 1033 to 1386 of the nucleotide sequence shown in FIG. 1, SEQ ID NO:1), which comprise a ubiquitin binding domain.

A nucleotide (1977 nucleotides shown in FIG. 3, SEQ ID NO:3) and amino acid sequence (419 amino acids shown in FIG. 4, SEQ ID NO:4) of a second member of the p62 polypeptide family are also disclosed herein. A plasmid containing the nucleotide sequence encoding this second p62 polypeptide has been deposited with the American Type Culture Collection (ATCC) 10801 University Boulevard, Manassas, Va. 20110-2209 on Dec. 19, 1995 and was assigned ATCC Accession Number 97386. This second p62 polypeptide family member is also a human cytoplasmic polypeptide with a molecular weight of about 62 kD and is expressed in a variety of tissues including B cells and other cells of hematopoietic origin, e.g., T cells. The mRNA which encodes this polypeptide includes about 2 kb. This second p62 polypeptide is encoded by a nucleic acid sequence which has a 77.5% overall sequence identity with the nucleotide sequences shown in FIG. 1, SEQ ID NO:1. The amino acid sequence of the second p62 polypeptide has an 88.5% overall sequence identity with the amino acid sequence shown in FIG. 2, SEQ ID NO:2. A comparison of the nucleotide sequences of the first p62 polypeptide and the second p62 polypeptide is shown in FIG. 6. A comparison of the amino acid sequences of the first p62 polypeptide and the second p62 polypeptide is shown in FIG. 7. Like the first p62 polypeptide, the second p62 polypeptide family member includes several defined domains. The SH2 binding domain of the second p62 polypeptide comprises at least amino acid residues 1–20 of the amino acid sequence of FIG. 4, SEQ ID NO:4. A rac GTPase binding motif appears at amino acid residues 46–62 as shown in FIG. 4, SEQ ID NO:4 (which are encoded by nucleotides 136–186 as shown in FIG. 3, SEQ ID NO:3) of the second p62 polypeptide. The second p62 polypeptide also includes a zinc finger domain which comprises amino acid residues 108–143 of FIG. 4, SEQ ID NO:4, which are encoded by nucleotides 322–429 of FIG. 3, SEQ ID NO:3. In addition, an SH3 binding domain appears at amino acid residues 183–191 (encoded by nucleotides 548–573 of FIG. 3, SEQ ID NO:3) and a PEST motif appears at amino acid residues 246–276 of FIG. 4, SEQ ID NO:4 (encoded by nucleotides 736–828 of FIG. 3, SEQ ID NO:3). The second p62 polypeptide family member also includes at least one phosphorylation site at threonine 249 of the amino acid sequence of FIG. 4, SEQ ID NO:4 (encoded by nucleotides 745–747 of the nucleotide sequence shown in FIG. 3, SEQ ID NO:3). The C-terminus of the second p62 polypeptide includes an amino acid sequence comprising amino acid residues 303–419 of the amino acid sequence shown in FIG. 4, SEQ ID NO:4 (encoded by nucleotides 907–1257 of the nucleotide sequence shown in FIG. 3, SEQ ID NO:3), which comprise a ubiquitin binding domain.

Members of the human p62 polypeptide family are the first polypeptides shown to have both an SH2 binding domain and a ubiquitin binding domain. Furthermore, the p62 polypeptides bind to SH2 domains in a phosphotyrosine-independent manner. Although other proteins have been demonstrated as having this characteristic (see e.g., Malek, S. N. et al. (1994) *J. Biol. Chem.* 269(52) :33009–33020 (p130$^{PITSLRE}$ protein); Cleghon, V. et al. (1994) *J. Biol. Chem.* 269(26):17749–17755 (raf-1 protein); Muller, A. J. et al. (1992) *Mol. Cell Biol.* 12(11):5087–5093 (BCR protein)), these proteins require phosphorylation of one or more of their serine residues. Binding of the p62 polypeptides to an SH2 domain, e.g., the SH2 domain of Lck, however, does not require phosphorylation of a p62 serine residue. Moreover, neither the p130$^{PITSLRE}$ protein, the raf-1 protein, nor the BCR protein, has been shown to include a ubiquitin binding domain.

Accordingly, this invention pertains to p62 polypeptides and to active portions or fragments thereof, such as peptides having an activity of p62. The phrases "an activity of p62" or "having a p62 activity" are used interchangeably herein to refer to molecules such as proteins, polypeptides, and peptides which have one or more of the following functional characteristics:

(1) the p62 polypeptide binds to an SH2 domain, e.g., an SH2 domain which comprises an amino acid sequence having at least about 70% or more (e.g., 80%, 90%, 95%, 97%, 98%) sequence identity with the amino acid sequence of the SH2 domain of p56$^{lck}$. In a preferred embodiment, the p62 polypeptide binds to the SH2 domain of p56$^{lck}$. The binding of the p62 polypeptide to an SH2 domain is preferably phosphotyrosine independent;

(2) the p62 polypeptide binds, e.g., binds noncovalently, to ubiquitin, a ubiquitin analog, derivative or active fragment;

(3) the p62 polypeptide modulates T cell development (e.g., T cell differentiation) and/or T cell activation (e.g., lymphokine secretion);

(4) the p62 polypeptide modulates B cell development (e.g., B cell differentiation) and/or B cell activation (e.g., antibody secretion);

(5) the p62 polypeptide modulates (e.g., inhibits) ubiquitin-mediated degradation of cellular proteins such as cell cycle regulatory proteins (e.g., p53);

(6) the p62 polypeptide modulates (e.g., stimulates) expression of cell cycle dependent kinase inhibitors (e.g., p21$^{cip}$);

(7) the p62 polypeptide binds to or interacts with proteins involved in the ras cell signaling cascade, e.g., p120-GAP;

(8) the p62 polypeptide binds to or interacts with GTPase;

(9) the p62 polypeptide modulates cell cycle progression, e.g., arrests cell cycle progression at, for example, the G1/S boundary;

(10) the p62 polypeptide modulates, e.g., inhibits, cell proliferation (e.g., cell proliferation associated with neoplasia); and

(11) the p62 polypeptide associates with a Ser/Thr protein kinase activity.

The p62 polypeptides can have different activities in different tissues. For example, in T and B cells, the p62 polypeptides can activate T or B cell development as described herein. In other cells, e.g., epithelial cells, e.g., HeLa cells, however, the p62 polypeptides can inhibit cell cycle progression.

The phrase "SH2 domain", as used herein, refers to a conserved sequence of approximately 100 amino acids found in many signal transduction proteins including Fps, Stc, Abl, GAP, PLCλ, v-Crk, Nck, Lck, Fyn, p85, and Vav. See, e.g., Koch et al. (1991) *Science* 252:668, incorporated herein by reference (provides the amino acid sequences of the SH2 domain of 27 proteins). The SH2 domain mediates protein-protein interactions between the SH2 containing protein and other proteins by recognition of a specific site on a second protein. The SH2/second protein site interaction usually results in an association of the SH2 contacting protein and the second protein. As used herein, SH2 domain refers to any sequence with at least about 70%, preferably at least about 80%, and more preferably at least about 90% or more (95%, 97%–98%) sequence identity with a naturally occurring SH2 domain, e.g., the SH2 domain of Lck (also referred to herein as "p56$^{lck}$") as shown in FIG. 5, SEQ ID NO:5.

As used herein, the term "ubiquitin" is art recognized and refers to a polypeptide, e.g., a polypeptide of about 76 amino acids, which mediates degradation of intracellular proteins in eukaryotic cells. Ubiquitin modification of a variety of protein targets within the cell is important in a number of basic cellular functions such as regulation of gene expression, regulation of the cell-cycle, modification of cell surface receptors, biogenesis of ribosomes, and DNA repair. Several key regulatory proteins are known to be degraded through the ubiquitin-mediated pathway, including certain transcriptional regulators, key enzymes of metabolic pathways, cyclins, and the tumor suppressor p53. Targeted proteins which undergo selective ubiquitin-mediated degradation are covalently tagged with ubiquitin through the formation of an isopeptide bond between the C-terminal glycyl residue of ubiquitin and a specific lysyl residue in the substrate protein. This process is catalyzed by a ubiquitin-activating enzyme (E1) and a ubiquitin-conjugating enzyme (E2), and in some instances may also require auxiliary substrate recognition proteins (E3s). Following the linkage of the first ubiquitin chain, additional molecules of ubiquitin may be attached to lysine side chains of the previously conjugated moiety to form branched multi-ubiquitin chains. Once ubiquitin is conjugated to the target protein, a variety of evidence suggests that ubiquitin protein conjugates are degraded by a proteasome, a multi subunit protein complex. The term "ubiquitin" encompasses ubiquitin analogs, derivatives or active fragments thereof which are capable of mediating degradation of intracellular proteins as described herein.

Ubiquitin binds to proteins via three known mechanisms. In the first mechanism, ubiquitin is conjugated to a target protein through an isopeptide bond between the C-terminal glycyl residue of ubiquitin and the $\epsilon$-amino group of a specific lysyl residue in the substrate protein. The second mechanism of ubiquitin binding to a target protein is a covalent binding of monoubiquitin to a protein such as that observed when ubiquitin binds to ubiquitin activating enzyme (E1), ubiquitin conjugating enzyme (E2), or ubiquitin ligase (E3). This mechanism of binding uses an ATP-dependent thioester formation between a cysteine residue in the active site of these enzymes. Dissociation of these enzyme-ubiquitin complexes requires dithiothreitol (DTT). In the third mechanism, ubiquitin binds noncovalently to certain proteins such as ubiquitin hydrolase and deubiquitinase. This mode of interaction is a simple noncovalent protein-protein interaction.

Association and dissociation of p62 with ubiquitin does not require ATP or DTT. This mode of binding indicates that the p62-ubiquitin interaction involves noncovalent binding. p62, however, does not share conserved regions with ubiquitin hydrolase and ubiquitinase. Furthermore, p62 cannot cleave covalently attached ubiquitin from a target protein. Thus, although p62-ubiquitin binding is noncovalent binding, the specific mode of binding is unlike that previously demonstrated for ubiquitin hydrolase and deubiquitinase.

As used herein, the phrase "cell cycle dependent kinase inhibitor" refers to molecules, e.g., proteins or peptides, which inhibit at least one cyclin dependent kinase (cdk). In the eukaryotic cell cycle, a key role is played by the cdks. Cdk complexes are formed via the association of a regulatory cyclin subunit and a catalytic kinase subunit. In mammalian cells, the combination of the kinase subunits (cdc2, cdk2, cdk4, cdk5, cdk6) with a variety of cyclin subunits (cyclin A, B1, B2, D1, D2, D3 and E) results in the assembly of functionally distinct kinase complexes. The coordinated activation of these complexes drives the cells through the cell cycle and ensures the fidelity of the process (Draetta (1990) *Trends Biochem. Sci.* 15:378–382; Sherr (1993) *Cell* 73:1059–1065). Recently, a link has been established between the regulation of the activity of cyclin-dependent kinases and cancer by the discovery of a group of cdk inhibitors including $p27^{Kip1}$, $p21^{Waf1/Cip1}$ and $p16^{Ink4/MTS1}$. $p21^{Waf1/Cip1}$ is positively regulated by the tumor suppressor p53 which is mutated in approximately 50% of all human cancers. Harper et al. (1993) *Cell* 75:805–816. $p21^{Waf1/Cip1}$ may mediate the tumor suppressor activity of p53 at the level of cyclin-dependent kinase activity. The inhibitory activity of $p27^{Kip1}$ is induced by the negative growth factor TGF-$\mu$ and by contact inhibition (Polyak et al. (1994) *Cell* 78:66–69). These proteins, when bound to cdk complexes, inhibit their kinase activity, thereby inhibiting progression through the cell cycle. Although their precise mechanism of action is unknown, it is thought that binding of these inhibitors to the cdk/cyclin complex prevents its activation. Alternatively, these inhibitors may interfere with the interaction of the enzyme with its substrates or its cofactors. In addition to modulating the expression of cdks, the p62 polypeptides can be targets of the cdks, e.g., the p62 polypeptides can be phosphorylated, e.g., at one or more of the phosphorylation sites described herein, by a cdk.

Proteins involved in the ras cell signaling pathway or cascade are art recognized. See, e.g., Murray, A. and Hunt, T. eds. The Cell Cycle: An Introduction (W. H. Freeman and Company, New York) pp. 109–110. Briefly, the ras cell signaling cascade begins with cell activation, e.g., cell activation by a growth factor, and activation of the growth factor receptor. Receptor binding leads to the binding of adaptor proteins, such as GRB2 and SEM5, which contain SH2 and SH3 domains. The adaptor proteins activate guanine nucleotide-exchange proteins and GTPase activating proteins, e.g., p120-GAP, which, in turn, activate small G proteins such as ras. Ras, which is a GTPase, in turn, induces activation and phosphorylation of raf, a protein kinase. Raf is the first member of the protein kinase cascade which ultimately leads to the phosphorylation and activation of MAP kinase. Activation of MAP kinase leads to its translocation into the nucleus where it induces transcription. The p62 polypeptides of the present invention can bind to one or more of the molecules involved in the ras cell signaling cascade. Moreover, the p62 polypeptides of the invention can also be targets of the kinases of this cascade, e.g., the p62 polypeptides can be phosphorylated, e.g., at one or more of the phosphorylation sites described herein, by a kinase, e.g., MAP kinase, involved in the ras cascade.

GTPases have been found to control processes as diverse as growth control, apoptosis, translation, vesicular transport, cytoskeletal organization, and nuclear transport (Chant, J. and Stowers, L. (1995) *Cell* 81:1–4). Examples of other known GTPases include rac, rho, and cdc42. p62 binding to a GTPase demonstrates that p62 also controls a number of cellular events including focal adhesion and stress fiber formation, that are all important in cell growth and cell cycle progression.

Polypeptides having a p62 activity can have any one or more of the activities described herein. An example of a preferred polypeptide having a p62 activity is a polypeptide which is capable of binding to an SH2 domain and to ubiquitin.

Various aspects of the invention are described in further detail in the following subsections:

I. Isolated Nucleic acid Molecules

One aspect of this invention pertains to isolated nucleic acid molecules that encode a novel p62 polypeptide, such as human p62, portions or fragments of such nucleic acids, or equivalents thereof. The term "nucleic acid molecule" as used herein is intended to include such fragments or equivalents and refers to DNA molecules (e.g., cDNA or genomic DNA) and RNA molecules (e.g., mRNA). The nucleic acid molecule can be single-stranded or double-stranded, but preferably is double-stranded DNA. An "isolated" nucleic acid molecule is free of sequences which naturally flank the nucleic acid (i.e., sequences located at the 5' and 3' ends of the nucleic acid) in the genomic DNA of the organism from which the nucleic acid is derived. Moreover, an "isolated" nucleic acid molecule, such as a cDNA molecule, can be free of other cellular material.

The term "equivalent" is intended to include nucleotide sequences encoding a functionally equivalent p62 polypeptide or functionally equivalent polypeptide or peptides having a p62 activity. Functionally equivalent p62 polypeptide or peptides include polypeptides which have one or more of the functional characteristics described herein.

Other equivalents of p62 polypeptides include structural equivalents. Structural equivalents of a p62 polypeptide preferably comprise an SH2 binding domain and a ubiquitin binding domain. Preferably the SH2 binding domain binds to the SH2 domain of Lck as set forth herein. Other preferred structural equivalents of p62 polypeptides include an SH2 binding domain, a ubiquitin binding domain, and optionally one or more of the domains present in p62 polypeptides described herein. Preferred nucleic acids of the invention include nucleic acid molecules comprising a nucleotide sequence provided in FIG. 1 (SEQ ID NO: 1) or FIG. 3 (SEQ ID NO:3) or fragments, portions or equivalents thereof.

In one embodiment, the invention pertains to a nucleic acid molecule which is a naturally occuring form of a nucleic acid molecule encoding a p62 polypeptide, such as a p62 polypeptide having an amino acid sequence shown in FIG. 2 (SEQ ID NO:2) or FIG. 4 (SEQ ID NO:4). A naturally occuring form of a nucleic acid encoding p62 is derived from hematopoietic cells. Such naturally occuring equivalents can be obtained, for example, by screening a cDNA library, prepared with RNA from hematopoietic cells, with a nucleic acid molecule having a sequence shown in FIG. 1 (SEQ ID NO:1) or FIG. 3 (SEQ ID NO:3) under high stringency hybridization conditions. Such conditions are further described herein. Also within the scope of the invention are nucleic acids encoding natural variants and isoforms of p62 polypeptides, such as splice forms. Such natural variants are within the scope of the invention.

In a preferred embodiment, the nucleic acid molecule encoding a p62 polypeptide is a cDNA. Preferably, the nucleic acid molecule is a cDNA molecule consisting of at least a portion of a nucleotide sequence encoding human p62, as shown in FIG. 1 (SEQ ID NO:1) or as shown in FIG. 3 (SEQ ID NO:3). A preferred portion of the cDNA molecule of FIG. 1 (SEQ ID NO:1) or FIG. 3 (SEQ ID NO:3) includes the coding region of the molecule. Other preferred portions include those which code for domains of p62, such as the SH2 binding domain, the GTPase binding domain, the zinc finger domain, the domain containing at least one of the above-described phosphorylation sites, and the ubiquitin binding, or any combination thereof. Additional regions of the nucleic acid molecules of the invention encode polypeptides which comprise an SH3 binding domain and a PEST domain.

In another embodiment, the nucleic acid of the invention encodes a p62 polypeptide or an active portion or fragment thereof having an amino acid sequence shown in FIG. 2 (SEQ ID NO:2) or in FIG. 4 (SEQ ID NO:4). In yet another embodiment, preferred nucleic acid molecules encode a polypeptide having an overall amino acid sequence identity of at least about 50%, more preferably at least about 60%, more preferably at least about 70%, more preferably at least about 80%, and most preferably at least about 90% or more with an amino acid sequence shown in FIG. 2 (SEQ ID NO:2) or FIG. 4 (SEQ ID NO:4). Nucleic acid molecules which encode peptides having an overall amino acid sequence identity of at least about 93%, more preferably at least about 95%, and most preferably at least about 98–99% with a sequence set forth in FIG. 2 (SEQ ID NO:2) or FIG. 4 (SEQ ID NO:4) are also within the scope of the invention. Homology, also termed herein "identity" refers to sequence similarity between two protein (peptides) or between two nucleic acid molecules. Homology can be determined by comparing a position in each sequence which may be aligned for purposes of comparison. When a position in the compared sequences is occupied by the same nucleotide base or amino acid, then the molecules are homologous, or identical, at that position. A degree (or percentage) of homology between sequences is a function of the number of matching or homologous positions shared by the sequences.

Isolated nucleic acids encoding a peptide having a p62 activity, as described herein, and having a sequence which differs from nucleotide sequence shown in FIG. 1 (SEQ ID NO:1) or FIG. 3 (SEQ ID NO:3) due to degeneracy in the genetic code are also within the scope of the invention. Such nucleic acids encode functionally equivalent peptides (e.g., having a p62 activity) or structurally equivalent polypeptides but differ in sequence from the sequence of FIG. 2 (SEQ ID NO:2) or FIG. 4 (SEQ ID NO:4) due to degeneracy in the genetic code. For example, a number of amino acids are designated by more than one triplet. Codons that specify the same amino acid, or synonyms (for example, CAU and CAC are synonyms for histidine) may occur due to degeneracy in the genetic code. As one example, DNA sequence polymorphisms within the nucleotide sequence of a p62 polypeptide (especially those within the third base of a codon) may result in "silent" mutations in the DNA which do not affect the amino acid encoded. However, it is expected that DNA sequence polymorphisms that do lead to changes in the amino acid sequences of the p62 polypeptide will exist within a population. It will be appreciated by one skilled in the art that these variations in one or more nucleotides (up to about 3–4% of the nucleotides) of the nucleic acids encoding peptides having the activity of a p62 polypeptide may exist among individuals within a population due to natural allelic variation. Any and all such nucleotide variations and resulting amino acid polymorphisms are within the scope of the invention. Furthermore, there are likely to be isoforms or family members of the p62 polypeptide family in addition to those described herein. Such isoforms or family members are defined as proteins related in function and amino acid sequence to a p62 polypeptide, but encoded by genes at different loci. Such isoforms or family members are within the scope of the invention. Additional members of the p62 polypeptide family can be isolated by, for example, screening a library of interest under low stringency conditions described herein or by screening or amplifying with degenerate probes derived from highly conserved amino acids sequences, for example, from the amino acid sequences in FIG. 2, SEQ ID NO:2 or in FIG. 4, SEQ ID NO:4. Alternatively, other members of the p62 polypeptide family as well as the remaining N-terminal portion of the second p62 polypeptide described herein, can be isolated using one or more of the following techniques. For example, the Daudi cell library which was initially screened to obtain the second p62 cDNA (i.e., by analyzing three positive clones from a pool of $0.5 \times 10^5$ individual colonies) can be further screened by analyzing $5 \times 10^5$ individual colonies. This library can be screened using a 150 base pair probe obtained from the 5' end of the cDNA shown in FIG. 3, SEQ ID NO:3. Alternatively, using a protocol known as RACE ("Rapid Amplification of cDNA End" described in Frohman, M. A. PCR Protocols (Academic Press, Inc. 1990) pp. 28–38, the missing 5' end of the nucleotide sequence encoding the second p62 polypeptide can be obtained. The RACE protocol begins with a purification of 1 µg of polyA RNA from cultured Daudi cells. The polyA RNA is then used as a template for the RACE reaction. A gene specific primer encoding a 17-mer minus strand complementary to nucleotide 11 to 27 of SEQ ID NO:3 (AGCGGCGGAATTCCACC (SEQ ID NO:22)) is then used to extend the 5' end of the cDNA by AMV reverse transcriptase. A homopolymer (oligo dC) is then appended by using terminal transferase to tail the first-strand reaction product. Finally, amplification by PCR is accomplished using a gene specific primer synthesized as described above and a hybrid primer containing oligo dG. The amplified gene product can then be sequenced. Other techniques for isolating additional members of the p62 polypeptide family as well as the N-terminal portion of the second p62 polypeptide include screening a genomic B cell library to obtain genes of the p62 family. Positive clones are then analyzed and sequenced to obtain additional family members.

A "fragment" or "portion" of a nucleic acid encoding a p62 polypeptide is defined as a nucleotide sequence having fewer nucleotides than the nucleotide sequence encoding the entire amino acid sequence of a p62 polypeptide, such as human p62. A fragment or portion of a nucleic acid molecule is at least about 20 nucleotides, preferably at least about 30 nucleotides, more preferably at least about 40 nucleotides, even more preferably at least about 50 nucleotides in length. Also within the scope of the invention are nucleic acid fragments which are at least about 60, 70, 80, 90, 100 or more nucleotides in length. Preferred fragments or portions include fragments which encode a polypeptide having a p62 activity as described herein. To identify fragments of portions of the nucleic acids encoding fragments or portions of polypeptides which have a p62 activity, several different assays can be employed. For example, to determine the binding characteristics of p62 peptides, commonly practiced binding studies, for example, those described in the Examples section herein can be performed to obtain p62 peptides which bind to, for example, an SH2 domain, ubiquitin, or GTPase.

For determining whether a p62 polypeptide or portion or fragment thereof, such as a fragment of human p62 is capable of modulating T cell activity, such as T cell proliferation or lymphokine secretion, e.g., IL-2 secretion, the polypeptide, is added to a culture of T cells, such as CD4+ T cells, and incubated in the presence of a primary activation signal, such as an anti-CD3 antibody and various amounts of a p62 portion or fragment. Following incubation for about 3 days, a proliferation assay is performed, which is indicative of the proliferation rate of the T cells. Thus, a fragment of a p62 antigen which is capable of costimulating T cells is a fragment of a p62 antigen which in the presence of a primary T cell activation signal stimulates the T cells to proliferate at a rate that is greater than proliferation rate of T cells contacted only with a primary activation signal. Proliferation assays can also be performed as described in the PCT Application No. PCT/US94/08423. Lymphokine secretion, e.g., secretion of the lymphokines IL-2, tumor necrosis factor (TNF), granulocyte-macrophage-colony stimulating factor (GM-CSF), and gamma interferon can be measured using standard assays. Alternatively, T cells transfected with a cDNA encoding a p62 polypeptide or fragment or portion thereof which has a p62 activity can be used to screen for agents which inhibit p62. In such cells, the level of IL-2 gene activation and/or level of stimulation could be measured to indicate inhibition or activation of p62.

Another aspect of the invention provides a nucleic acid which hybridizes under high or low stringency conditions to a nucleic acid which encodes a peptide having all or a portion of an amino acid sequence shown in FIG. 2 (SEQ ID NO:2) or FIG. 4 (SEQ ID NO:4). Appropriate stringency conditions which promote DNA hybridization, for example, 6.0× sodium chloride/sodium citrate (SSC) at about 45° C., followed by a wash of 2.0× SSC at 50° C. are known to those skilled in the art or can be found in Current Protocols in Molecular Biology, John Wiley & Sons, N.Y. (1989), 6.3.1–6.3.6. For example, the salt concentration in the wash step can be selected from a low stringency of about 2.0× SSC at 25 ° C. to a high stringency of about 0.2× SSC at 65° C. In addition, the temperature in the wash step can be increased from low stringency conditions at room temperature, about 22° C., to high stringency conditions, at about 65° C. Preferably, an isolated nucleic acid molecule of the invention that hybridizes under stringent conditions to the sequence of FIG. 1, SEQ ID NO:1 or FIG. 3, SEQ ID NO:3 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural p62 polypeptide.

In addition to naturally-occurring allelic variants of the p62 sequence that may exist in the population, the skilled artisan will further appreciate that changes may be introduced by mutation into the nucleotide sequence of FIG. 1, SEQ ID NO:1 or FIG. 3, SEQ ID NO:3, thereby leading to changes in the amino acid sequence of the encoded p62 polypeptide, without altering the functional ability of the p62 polypeptide. For example, nucleotide substitutions leading to amino acid substitutions at "non-essential" amino acid residues may be made in the sequence of FIG. 1, SEQ ID NO:1 or FIG. 3, SEQ ID NO:3. A "non-essential" amino acid residue is a residue that can be altered from the wild-type sequence of p62 (e.g., the sequence of FIG. 2, SEQ ID NO:2 or FIG. 4, SEQ ID NO:4) without altering the p62 activity of the polypeptide.

An isolated nucleic acid molecule encoding a p62 polypeptide homologous to the protein of FIG. 2, SEQ ID NO:2 or FIG. 4, SEQ ID NO:4 can be created by introducing one or more nucleotide substitutions, additions or deletions into the nucleotide sequence of FIG. 1, SEQ ID NO:1 or FIG. 3, SEQ ID NO:3 such that one or more amino acid substitutions, additions or deletions are introduced into the encoded polypeptide. Mutations can be introduced into FIG. 1, SEQ ID NO:1 or FIG. 3, SEQ ID NO:3 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in p62 is preferably replaced with another amino acid residue from the same side chain family. Alternatively, in another embodiment, mutations can be introduced randomly along all or part of a p62 coding sequence, such as by saturation mutagenesis, and the resultant mutants can be screened for proteolytic activity to identify mutants that retain proteolytic activity. Following mutagenesis of the nucleotide sequence of FIG. 1, SEQ ID NO:1 or FIG. 3, SEQ ID NO:3, the encoded polypeptide can be expressed recombinantly and activity of the protein can be determined.

In addition to the nucleic acid molecules encoding p62 polypeptides described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire p62 coding strand, or to only a portion thereof. In one embodiment, an antisense nucleic acid molecule is antisense to a "coding region" of the coding strand of a nucleotide sequence encoding p62. The term "coding region" refers to the region of the nucleotide sequence comprising codons which are translated into amino acid residues (e.g., the entire coding region of FIG. 1, SEQ ID NO:1 or FIG. 3, SEQ ID NO:3). In another embodiment, the antisense nucleic acid molecule is antisense to a "noncoding region" of the coding strand of a nucleotide sequence encoding p62. The term "noncoding region" refers to 5' and 3' sequences which flank the coding region that are not translated into amino acids (i.e., also referred to as 5' and 3' untranslated regions).

Given the coding strand sequences encoding p62 polypeptides disclosed herein (e.g., FIG. 1, SEQ ID NO:1 and FIG. 3, SEQ ID NO:3), antisense nucleic acids of the invention can be designed according to the rules of Watson and Crick base pairing. The antisense nucleic acid molecule can be complementary to the entire coding region of p62 mRNA, but more preferably is an oligonucleotide which is antisense to only a portion of the coding or noncoding region of p62 mRNA. For example, the antisense oligonucleotide can be complementary to the region surrounding the translation start site of p62 mRNA. An antisense oligonucleotide can be, for example, about 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. A ribozyme having specificity for a p62-encoding nucleic acid can be designed based upon the nucleotide sequence of a p62 cDNA disclosed herein (i.e., FIG. 1, SEQ ID NO:1 or FIG. 3, SEQ ID NO:3). See, e.g, Cech et al. U.S. Pat. No. 4,987,071; and Cech et al. U.S. Pat. No. 5,116,742. Alternatively, p62 mRNA can be used to select a catalytic RNA having a specific ribonuclease activity from a pool of RNA molecules. See, e.g., Bartel, D. and Szostak, J. W. (1993) *Science* 261: 1411–1418.

The nucleic acid sequences of the invention can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al U.S. Pat. No. 4,458,066; and Itakura U.S. Pat. Nos. 4,401,796 and 4,373,071, incorporated by reference herein).

II. Recombinant Expression Vectors and Host Cells

Another aspect of the invention pertains to vectors, preferably expression vectors, containing a nucleic acid encoding p62 (or a portion or fragment thereof). As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., p62 polypeptides, mutant forms of p62, fusion proteins, etc.).

The recombinant expression vectors of the invention can be designed for expression of p62 in prokaryotic or eukaryotic cells. For example, p62 can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nuc. Acids Res.* 20:2111–2118). Such alteration of nucleic acid sequences of the invention can be carried out by standard DNA synthesis techniques.

In another embodiment, the p62 expression vector is a yeast expression vector. Examples of vectors for expression in yeast *S. cerivisae* include pYepSec1 (Baldari. et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Alternatively, p62 can be expressed in insect cells using baculovirus expression vectors. Baculovirus vectors available for expression of proteins in cultured insect cells (e.g., Sf9 cells) include the pAc series (Smith et al., (1983) *Mol. Cell Biol.* 3:2156–2165) and the pVL series (Lucklow, V. A., and Summers, M. D., (1989) *Virology* 170:31–39).

In yet another embodiment, a nucleic acid of the invention is expressed in mammalian cells using a mammalian expression vector. Examples of mammalian expression vectors include pCDM8 (Seed, B., (1987) *Nature* 329:840) and pMT2PC (Kaufman et al. (1987), *EMBO J.* 6:187–195). When used in mammalian cells, the expression vector's control functions are often provided by viral regulatory elements. For example, commonly used promoters are derived from polyoma, adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

In one embodiment, a recombinant expression vector containing DNA encoding a p62 fusion protein is produced. A p62 fusion protein can be produced by recombinant expression of a nucleotide sequence encoding a first polypeptide peptide having a p62 activity and a nucleotide sequence encoding a second polypeptide having an amino acid sequence unrelated to an amino acid sequence selected from the group consisting of an amino acid sequence shown in FIG. 2 (SEQ ID NO:2) and FIG. 4 (SEQ ID NO:4). In many instances, the second polypeptide correspond to a moiety that alters a characteristic of the first peptide, e.g., its solubility, affinity, stability or valency. For example, a p62 polypeptide of the present invention can be generated as a glutathione-S-transferase (GST-fusion protein). Such GST fusion proteins can enable easy purification of the p62 polypeptide, such as by the use of glutathione-derivatized matrices (see, for example, *Current Protocols in Molecular Biology*, eds. Ausabel et al. (N.Y.: John Wiley & Sons, 1991)). Preferably the fusion proteins of the invention are functional in a two hybrid assay. Fusion proteins and peptides produced by recombinant techniques may be secreted and isolated from a mixture of cells and medium containing the protein or peptide. Alternatively, the protein or peptide may be retained cytoplasmically and the cells harvested, lysed and the protein isolated. A cell culture typically includes host cells, media and other byproducts. Suitable media for cell culture are well known in the art. Protein and peptides can be isolated from cell culture medium, host cells, or both using techniques known in the art for purifying proteins and peptides. Techniques for transfecting host cells and purifying proteins and peptides are described in further detail herein.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to p62 RNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to recombinant host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell may be any prokaryotic or eukaryotic cell. For example, a p62 polypeptide can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same vector as that encoding p62 or may be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) p62 polypeptide. Accordingly, the invention further provides methods for producing p62 polypeptides using the host cells of the invention. In one embodiment, the method comprises culturing the host cell of invention (into which a recombinant expression vector encoding p62 has been introduced) in a suitable medium until p62 is produced. In another embodiment, the method further comprises isolating p62 from the medium or the host cell.

The host cells of the invention can also be used to produce nonhuman transgenic animals. For example, in one embodiment, a host cell of the invention is a fertilized oocyte or an embryonic stem cell into which p62-coding sequences have been introduced. Such host cells can then be used to create non-human transgenic animals in which exogenous p62 sequences have been introduced into their genome or homologous recombinant animals in which endogenous p62 sequences have been altered. Such animals are useful for studying the function and/or activity of p62 and for identifying and/or evaluating modulators of p62 activity. As used herein, a "transgenic animal" is a non-human animal, preferably a mammal, more preferably a mouse, in which one or more of the cells of the animal includes a transgene. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous p62 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing p62-encoding nucleic acid into the male pronuclei of a fertilized oocyte, e.g., by microinjection, and allowing the oocyte to develop in a pseudopregnant female foster animal. The human p62 cDNA sequence of FIG. 1, SEQ ID NO:1 or FIG. 3, SEQ ID NO:3 can be introduced as a transgene into the genome of a non-human animal. Alternatively, a nonhuman homologue of the human p62 gene, such as a mouse p62 gene, can be isolated based on hybridization to the human p62 cDNA (described further in subsection I above) and used as a transgene. Intronic sequences and polyadenylation signals can also be included in the transgene to increase the efficiency of expression of the transgene. A tissue-specific regulatory sequence(s) can be operably linked to the p62 transgene to direct expression of a p62 polypeptide to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the p62 transgene in its genome and/or expression of p62 mRNA in tissues or cells of the animals. A transgenic founder animal can then be used to breed additional animals carrying the transgene. Moreover, transgenic animals carrying a transgene encoding p62 can further be bred to other transgenic animals carrying other transgenes.

To create a homologous recombinant animal, a vector is prepared which contains at least a portion of a p62 gene into which a deletion, addition or substitution has been introduced to thereby alter, e.g., functionally disrupt, the p62 gene. The p62 gene can be a human gene (e.g., from a human genomic clone isolated from a human genomic library screened with the cDNA of FIG. 1, SEQ ID NO:1 or FIG. 3, SEQ ID NO:3), but more preferably, is a non-human homologue of a human p62 gene. For example, a mouse p62 gene can be isolated from a mouse genomic DNA library using the human p62 cDNA of FIG. 1, SEQ ID NO:1 or FIG. 3, SEQ ID NO:3 as a probe. The mouse p62 gene then can be used to construct a homologous recombination vector suitable for altering an endogenous p62 gene in the mouse genome. In a preferred embodiment, the vector is designed such that, upon homologous recombination, the endogenous p62 gene is functionally disrupted (i.e., no longer encodes a functional protein; also referred to as a "knock out" vector). Alternatively, the vector can be designed such that, upon homologous recombination, the endogenous p62 gene is mutated or otherwise altered but still encodes functional protein (e.g., the upstream regulatory region can be altered to thereby alter the expression of the endogenous p62 polypeptide). In the homologous recombination vector, the altered portion of the p62 gene is flanked at its 5' and 3' ends by additional nucleic acid of the p62 gene to allow for homologous recombination to occur between the exogenous p62 gene carried by the vector and an endogenous p62 gene in an embryonic stem cell. The additional flanking p62 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced p62 gene has homologously recombined with the endogenous p62 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Fmbryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

III. Isolated p62 Proteins and Anti-p62 Antibodies

Another aspect of the invention pertains to isolated p62 polypeptides and active fragments or portions thereof, i.e., peptides having a p62 activity, such as human p62. This invention also provides a preparation of p62 or fragment or portion thereof. An "isolated" protein is substantially free of cellular material or culture medium when produced by recombinant DNA techniques, or chemical precursors or other chemicals when chemically synthesized. In a preferred embodiment, the p62 polypeptide has an amino acid sequence shown in FIG. 2, SEQ ID NO:2 or FIG. 4, SEQ ID NO:4. In other embodiments, the p62 polypeptide is substantially homologous or similar to FIG. 2, SEQ ID NO:2 or FIG. 4, SEQ ID NO:4 and retains the functional activity of the polypeptide of FIG. 2, SEQ ID NO:2 or FIG. 4, SEQ ID NO:4 yet differs in amino acid sequence due to natural allelic variation or mutagenesis, as described in detail in subsection I above. Accordingly, in another embodiment, the p62 polypeptide is a polypeptide which comprises an amino acid sequence at least about 70% overall amino acid identity with the amino acid sequence of FIG. 2, SEQ ID NO:2 or FIG. 4, SEQ ID NO:4. Preferably, the polypeptide is at least about 80%, more preferably at least about 90%, yet more preferably at least about 95%, and most preferably at least about 98–99% identical to FIG. 2, SEQ ID NO:2 or FIG. 4, SEQ ID NO:4.

An isolated p62 polypeptide can comprise the entire amino acid sequence of FIG. 2, SEQ ID NO:2 or FIG. 4, SEQ ID NO:4 or a biologically active portion or fragment thereof. For example, an active portion of p62 can comprise a selected domain of p62, such as the SH2 binding domain or the ubiquitin binding domain. Moreover, other biologically active portions, in which other regions of the protein are deleted, can be prepared by recombinant techniques and evaluated for a p62 activity as described in detail above. For example, a peptide having a p62 activity can differ in amino acid sequence from the human p62 depicted in FIG. 2, SEQ ID NO:2 or FIG. 4, SEQ ID NO:4, but such differences result in a peptide which functions in the same or similar manner as p62. Thus, peptides having the ability to modulate T cell activity, such as by inducing IL-2 production or T cell proliferation or having the ability to inhibit ubiquitin-mediated degradation of cell cycle regulatory proteins and which preferably have an SH2 binding domain and a ubiquitin binding domain. Preferred peptides of the invention include those which are further capable of modulating B cell activity such as by inducing B cell differentiation or stimulating B cell survival.

A peptide can be produced by modification of the amino acid sequence of the human p62 polypeptide shown in FIG. 2, SEQ ID NO:2 or FIG. 4, SEQ ID NO:4, such as a substitution, addition or deletion of an amino acid residue which is not directly involved in the function of p62. For example, in order to enhance stability and/or reactivity, the polypeptides or peptides of the invention can also be modified to incorporate one or more polymorphisms in the amino acid sequence of the protein allergen resulting from natural allelic variation. Additionally, D-amino acids, non-natural amino acids or non-amino acid analogues can be substituted or added to produce a modified protein or peptide within the scope of this invention. Furthermore, proteins or peptides of the present invention can be modified using the polyethylene glycol (PEG) method of A. Sehon and co-workers (Wie et al. supra) to produce a protein or peptide conjugated with PEG. In addition, PEG can be added during chemical synthesis of a protein or peptide of the invention. Modifications of proteins or peptides or portions thereof can also include reduction/alkylation (Tarr in: *Methods of Protein Microcharacterization*, J. E. Silver ed. Humana Press, Clifton, N.J., pp 155–194 (1986)); acylation (Tarr, supra); chemical coupling to an appropriate carrier (Mishell and Shiigi, eds, *Selected Methods in Cellular Immunology*, WH Freeman, San Francisco, Calif. (1980); U.S. Pat. No. 4,939, 239; or mild formalin treatment (Marsh *International Archives of Allergy and Applied Immunology*, 41:199–215 (1971)).

To facilitate purification and potentially increase solubility of proteins or peptides of the invention, it is possible to add reporter group(s) to the peptide backbone. For example, poly-histidine can be added to a peptide to purify the peptide on immobilized metal ion affinity chromatography (Hochuli, E. et al., *Bio/Technology*, 6:1321–1325 (1988)). In addition, specific endoprotease cleavage sites can be introduced, if desired, between a reporter group and amino acid sequences of a peptide to facilitate isolation of peptides free of irrelevant sequences.

Peptides of the invention are typically at least 30 amino acid residues in length, preferably at least 40 amino acid residues in length, more preferably at least 50 amino acid residues in length, and most preferably 60 amino acid residues in length. Peptides having p62 activity and including at least 80 amino acid residues in length, at least 100 amino acid residues in length, at least about 200, at least about 300, at least about 400, or at least about 500 or more amino acid residues in length are also within the scope of the invention. Other peptides within the scope of the invention include those encoded by the nucleic acids described herein.

Another embodiment of the invention provides a substantially pure preparation of a peptide having a p62 activity. Such a preparation is substantially free of proteins and peptides with which the peptide naturally occurs in a cell or with which it naturally occurs when secreted by a cell.

The term "isolated" as used throughout this application refers to a nucleic acid, protein or peptide having an activity of a p62 polypeptide substantially free of cellular material or culture medium when produced by recombinant DNA techniques, or chemical precursors or other chemicals when chemically synthesized. An isolated nucleic acid is also free of sequences which naturally flank the nucleic acid (i.e., sequences located at the 5' and 3' ends of the nucleic acid) in the organism from which the nucleic acid is derived.

The peptides and fusion proteins produced from the nucleic acid molecules of the present invention can also be used to produce antibodies specifically reactive with p62 polypeptides. For example, by using a full-length p62 polypeptide, such as an antigen having an amino acid sequence shown in FIG. 2, SEQ ID NO:2 or FIG. 4, SEQ ID NO:4, or a peptide fragment thereof, anti-protein/anti-peptide polyclonal antisera or monoclonal antibodies can be made using standard methods. A mammal, (e.g., a mouse, hamster, or rabbit) can be immunized with an immunogenic form of the protein or peptide which elicits an antibody response in the mammal. The immunogen can be, for example, a recombinant p62 polypeptide, or fragment or portion thereof or a synthetic peptide fragment. The immunogen can be modified to increase its immunogenicity. For example, techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay can be used with the immunogen as antigen to assess the levels of antibodies.

Following immunization, antisera can be obtained and, if desired, polyclonal antibodies isolated from the sera. To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. For example, the hybridoma technique originally developed by Kohler and Milstein (*Nature* (1975) 256:495–497) as well as other techniques such as the human B-cell hybridoma technique (Kozbar et al., *Immunol. Today* (1983) 4:72), the EBV-hybridoma technique to produce human monoclonal antibodies (Cole et al. *Monoclonal Antibodies in Cancer Therapy* (1985) Allen R. Bliss, Inc., pages 77–96), and screening of combinatorial antibody libraries (Huse et al., *Science* (1989) 246:1275). Hybridoma cells can be screened immunochemically for production of antibodies specifically reactive with the peptide and monoclonal antibodies isolated.

The term "antibody" as used herein is intended to include fragments thereof which are also specifically reactive with a peptide having the activity of a novel B lymphocyte antigen or fusion protein as described herein. Antibodies can be fragmented using conventional techniques and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules having an anti-p62 polypeptide (i.e., p62) portion.

When antibodies produced in non-human subjects are used therapeutically in humans, they are recognized to varying degrees as foreign and an immune response may be generated in the patient. One approach for minimizing or eliminating this problem, which is preferable to general immunosuppression, is to produce chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes the gene product of the novel p62 polypeptides of the invention. See, e.g., Morrison et al., (1985), *Proc. Natl. Acad Sci. USA*. 81:6851; Takedaetal., (1985), *Nature* 314:452, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. It is expected that such chimeric antibodies would be less immunogenic in a human subject than the corresponding non-chimeric antibody.

For human therapeutic purposes, the monoclonal or chimeric antibodies specifically reactive with a p62 polypeptide as described herein can be further humanized by producing human variable region chimeras, in which parts of the variable regions, especially the conserved framework regions of the antigen-binding domain, are of human origin and only the hypervariable regions are of non-human origin. General reviews of "humanized" chimeric antibodies are provided by Morrison, S. L. (1985) *Science* 229:1202–1207 and by Oi et al. (1986) *BioTechniques* 4:214. Such altered immunoglobulin molecules may be made by any of several techniques known in the art, (e.g., Teng et al., (1983), *Proc. NatL Acad Sci. USA*., 80:7308–7312; Kozbor et al., (1983), *Immunology Today*, 4:7279; Olsson et al., (1982), *Meth. Enzymol.*, 92:3–16), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain. Suitable "humanized" antibodies can be alternatively produced by CDR or CEA substitution (see U.S. Pat. No. 5,225,539 to Winter; Jones et al. (1986) *Nature* 321:552–525; Verhoeyan et al. (1988) *Science* 239:1534; and Beidler et al. (1988) *J. Immunol.* 141:4053–4060). Humanized antibodies which have reduced immunogenicity are preferred for immunotherapy in human subjects. Immunotherapy with a humanized antibody will likely reduce the necessity for any concomitant immunosuppression and may result in increased long term effectiveness for the treatment of chronic disease situations or situations requiring repeated antibody treatments.

As an alternative to humanizing a monoclonal antibody from a mouse or other species, a human monoclonal antibody directed against a human protein can be generated. Transgenic mice carrying human antibody repertoires have been created which can be immunized with a p62 polypeptide, such as human p62. Splenocytes from these immunized transgenic mice can then be used to create hybridomas that secrete human monoclonal antibodies specifically reactive with a p62 polypeptide (see, e.g., Wood et al. PCT publication WO 91/00906, Kucherlapati et al. PCT publication WO 91/10741; Lonberg et al. PCT publication WO 92/03918; Kay et al. PCT publication 92/03917; Lonberg, N. et al. (1994) *Nature* 368:856–859; Green, L. L. et al. (1994) *Nature Genet.* 7:13–21; Morrison, S. L. et al. (1994) *Proc. Natl. Acad. Sci. USA* 81:6851–6855; Bruggeman et al. (1993) *Year Immunol* 7:33–40; Tuaillon et al. (1993) *Proc. Natl. Acad. Sci. USA* 90:3720–3724; and Bruggeman et al. (1991) *Eur J Immunol* 21:1323–1326).

Monoclonal antibody compositions of the invention can also be produced by other methods well known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies that bind a p62 polypeptide of the invention (for descriptions of combinatorial antibody display see e.g., Sastry et al. (1989) *PNAS* 86:5728; Huse et al. (1989) *Science* 246:1275; and Orlandi et al. (1989) *PNAS* 86:3833). After immunizing an animal with a p62 polypeptide, the antibody repertoire of the resulting B-cell pool is cloned. Methods are generally known for directly obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al. (1991) *Biotechniques* 11: 152–156). A similar strategy can also been used to amplify human heavy and light chain variable regions from human antibodies (Larrick et al. (1991) *Methods: Companion to Methods in Enzymology* 2:106–110).

In an illustrative embodiment, RNA is isolated from activated B cells of, for example, peripheral blood cells, bone marrow, or spleen preparations, using standard protocols (e.g., U.S. Pat. No. 4,683,202; Orlandi, et al. *PNAS* (1989) 86:3833–3837; Sastry et al., *PNAS* (1989) 86:5728–5732; and Huse et al. (1989) *Science* 246:1275–1281.) First-strand cDNA is synthesized using primers specific for the constant region of the heavy chain(s) and each of the κ and λ light chains, as well as primers for the signal sequence. Using variable region PCR primers, the variable regions of both heavy and light chains are amplified, each alone or in combination, and ligated into appropriate vectors for further manipulation in generating the display packages. Oligonucleotide primers useful in amplification protocols may be unique or degenerate or incorporate inosine at degenerate positions. Restriction endonuclease recognition sequences may also be incorporated into the primers to allow for the cloning of the amplified fragment into a vector in a predetermined reading frame for expression.

The V-gene library cloned from the immunization-derived antibody repertoire can be expressed by a population of display packages, preferably derived from filamentous phage, to form an antibody display library. Ideally, the display package comprises a system that allows the sampling of very large diverse antibody display libraries, rapid sorting after each affinity separation round, and easy isolation of the antibody gene from purified display packages. In addition to commercially available kits for generating phage display libraries (e.g., the Pharmacia *Recombinant Phage Antibody System*, catalog no. 27-9400-01; and the Stratagene SurfZAP™ phage display kit, catalog no. 240612), examples of methods and reagents particularly amenable for use in generating a diverse antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370–1372; Hay et al. (1992) *Hum Antibod Hybridomas* 3:81–85; Huse et al. (1989) *Science* 246:1275–1281; Griffths et al. (1993) *EMBO J* 12:725–734; Hawkins et al. (1992) *J Mol Biol* 226:889–896; Clackson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; and Barbas et al. (1991) *PNAS* 88:7978–7982.

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., *Nature* (1990) 348:552–554, complete $V_H$ and $V_L$ domains of an antibody, joined by a flexible $(Gly_4\text{-}Ser)_3$ linker can be used to produce a single chain antibody which can render the display package separable based on antigen affinity. Isolated scFV antibodies immunoreactive with a peptide having activity of a p62 polypeptide can subsequently be formulated into a pharmaceutical preparation for use in the subject method.

Once displayed on the surface of a display package (e.g., filamentous phage), the antibody library is screened with a p62 polypeptide, or peptide fragment thereof, to identify and isolate packages that express an antibody having specificity for the p62 polypeptide. Nucleic acid encoding the selected antibody can be recovered from the display package (e.g., from the phage genome) and subcloned into other expression vectors by standard recombinant DNA techniques.

The polyclonal or monoclonal antibodies of the current invention, such as an antibody specifically reactive with a recombinant or synthetic peptide having a p62 activity can also be used to isolate the native p62 polypeptides from cells. For example, antibodies reactive with the peptide can be used to isolate the naturally-occurring or native form of p62 from, for example, B cells by immunoaffinity chromatography. In addition, the native form of cross-reactive p62-like molecules can be isolated from B cells or other cells by immunoaffinity chromatography with an anti-p62 antibody.

IV. Uses and Methods of the Invention

The invention further pertains to methods for inhibiting cell proliferation in a subject. These methods include administering to the subject a therapeutically effective amount of an agent which modulates p62 expression such that p62 expression is stimulated. Alternative methods for inhibiting cell proliferation in a subject include administering to the subject a therapeutically effective amount of a p62 polypeptide or fragment thereof or a vector comprising a nucleic acid molecule encoding a p62 polypeptide or fragment thereof. The term "inhibiting" as used herein refers to prevention, retardation, and/or termination of cell proliferation. As used herein, the phrase "cell proliferation" includes cell reproduction by, for example, cell division. Cell proliferation can be associated with normal cellular reproduction or can be associated with abnormal cellular reproduction, such as neoplasia. Subjects who can be treated by the method of this invention include living organisms, e.g. mammals. Examples of preferred subjects are those who have or are susceptible to unwanted cell proliferation, e.g., cell proliferation associated with neoplasia, e.g., neoplasia associated with p53 deregulation. Agents which modulate p62 expression, p62 polypeptides, and vectors containing nucleic acid encoding p62 polypeptides can be administered to the subject by a route of administration which allows the agent, polypeptide, or vector to perform its intended function. Various routes of administration are described herein in the section entitled "Pharmaceutical Compositions". Administration of a therapeutically active or therapeutically effective amount of an agent, polypeptide, or vector of the present invention is defined as an amount effective, at dosages and for periods of time necessary to achieve the desired result.

Other methods of the invention include methods for promoting cell proliferation in a subject. In one embodiment, these methods include administering to the subject a therapeutically effective amount of an agent which modulates p62 expression such that p62 expression is inhibited. In other embodiments, these methods include administering to the subject a therapeutically effective amount of an inhibitor of a p62 polypeptide such as a nucleic acid molecule which is antisense to a nucleic acid molecule encoding a p62 polypeptide or an antibody which binds a p62 polypeptide. The term "promoting" as used herein refers to activation or inducement of cell proliferation. In certain instances, it is desirable to promote cell proliferation. For example, promotion of cell proliferation would be desirable to promote would healing or to promote hair growth.

Still other methods of the present invention include methods for treating cancer, e.g., cancer associated with inhibition or deregulation of the tumor suppressor p53, e.g., cervical cancer, e.g., HPV-induced cervical cancer, in a subject. These methods include administering to the subject a therapeutically effective amount of a p62 polypeptide or fragment thereof, a therapeutically effective amount of a vector comprising a nucleic acid molecule encoding a p62 polypeptide, or a therapeutically effective amount of an agent which modulates p62 expression.

In one embodiment, the methods of the invention can used to treat cervical cancer, specifically cervical cancer induced by HPV, e.g. HPV-1, HPV-2, HPV-3, HPV-4, HPV-5, HPV-6, HPV-7, HPV-8, HPV-9, HPV-10, HPV-11, HPV-12, HPV-14, HPV-13, HPV-15, HPV-16, HPV-17 or HPV-18, and particularly high-risk HPVs, such as HPV-16, HPV-18, HPV-31 and HPV-33. The papillomaviruses (PV) are infectious agents that can cause benign epithelial tumors, or warts, in their natural hosts. Infection with specific HPVs has been associated with the development of human epithelial malignancies, including that of the uterine cervix, genitalia, skin and less frequently, other sites. Two of the transforming proteins produced by papillomaviruses, the E6 protein and E7 protein, form complexes with the tumor suppressor gene products p53 and Rb, respectively, indicating that these viral proteins may exert their functions through critical pathways that regulate cellular growth control. Such agents can be of use therapeutically to prevent E6-AP/E6 complexes in cells infected by, for example, human papillomaviruses, e.g. HPV-1, HPV-2, HPV-3, HPV-4, HPV-5, HPV-6, HPV-7, HPV-8, HPV-9, HPV-10, HPV-11, HPV-12, HPV-14, HPV-13, HPV-15, HPV-16, HPV-17 or HPV-18, particularly high-risk HPVs, such as HPV-16, HPV-18, HPV-31 and HPV-33. Contacting such cells with agents that alter the formation of one or more E6-BP/E6 complexes can inhibit pathological progression of papillomavirus infection, such as preventing or reversing the formation of warts, e.g. Plantar warts (verruca plantaris), common warts (verruca plana), Butcher's common warts, flat warts, genital warts (condyloma acuminatum), or epidermodysplasia verruciformis; as well as treating papillomavirus cells which have become, or are at risk of becoming, transformed and/or immortalized, e.g. cancerous, e.g. a laryngeal papilloma, a focal epithelial, a cervical carcinoma.

Further methods of the invention include methods for modulating T cell activity in a subject comprising administering to the subject a therapeutically effective amount of an agent which modulates p62 expression. Alternative methods for modulating T cell activity in a subject include administering to the subject a therapeutically effective amount of an agent which activates or inhibits a p62 polypeptide. Similar methods can be employed for modulating B cell activity. The term "modulate" as used herein refers to inhibition or activation/stimulation of a cell, e.g., a leukocyte. The term "leukocyte" is intended to include a cell of the blood which is not a red blood cell and includes lymphocytes, granulocytes, and monocytes. A preferred leukocyte is a lymphocyte, such as a B cell or a T cell.

T cell activity can be modulated, e.g., stimulated, in the methods of the present invention. T cell activation refers to a T cell response such as T cell proliferation, T cytotoxic activity, secretion of cytokines, differentiation or any T cell effector function. The term "T cell activation" is used herein to define a state in which a T cell response has been initiated or activated by a primary signal, such as through the TCR/CD3 complex, but not necessarily due to interaction with a protein antigen. A T cell is activated if it has received a primary signaling event which initiates an immune response by the T cell.

T cell activation can be accomplished by stimulating the T cell TCR/CD3 complex or via stimulation of the CD2 surface protein. An anti-CD3 monoclonal antibody can be used to activate a population of T cells via the TCR/CD3 complex. Although a number of anti-human CD3 monoclonal antibodies are commercially available, OKT3 prepared from hybridoma cells obtained from the American Type Culture Collection or monoclonal antibody G19-4 is preferred. Similarly, binding of an anti-CD2 antibody will activate T cells. Stimulatory forms of anti-CD2 antibodies are known and available. Stimulation through CD2 with anti-CD2 antibodies is typically accomplished using a combination of at least two different anti-CD2 antibodies. Stimulatory combinations of anti-CD2 antibodies which have been described include the following: the T11.3 antibody in combination with the T11.1 or T11.2 antibody (Meuer, S. C. et al. (1984) *Cell* 36:897–906) and the 9.6 antibody (which recognizes the same epitope as T11.1) in combination with the 9-1 antibody (Yang, S. Y. et al. (1986) *J. Immunol.* 137:1097–1 100). Other antibodies which bind to the same epitopes as any of the above described antibodies can also be used. Additional antibodies, or combinations of antibodies, can be prepared and identified by standard techniques.

A primary activation signal can also be provided by a polyclonal activator. Polyclonal activators include agents that bind to glycoproteins expressed on the plasma membrane of T cells and include lectins, such as phytohemaglutinin (PHA), concanavalin (Con A) and pokeweed mitogen (PWM).

A primary activation signal can also be delivered to a T cell through use of a combination of a protein kinase C (PKC) activator such as a phorbol ester (e.g., phorbol myristate acetate) and a calcium ionophore (e.g., ionomycin which raises cytoplasmic calcium concentrations). The use of these agents bypasses the TCR/CD3 complex but delivers a stimulatory signal to T cells. These agents are also known to exert a synergistic effect on T cells to promote T cell activation and can be used in the absence of antigen to deliver a primary activation signal to T cells.

The term "B cell" is intended to include a B lymphocyte that is at any state of maturation. Thus, the B cell can be a progenitor cell, a pre-B cell, an immature B cell, a mature B cell, a blast cell, a centroblast, a centrocyte, an activated B cell, a memory B cell, or an antibody secreting plasma cell. A preferred B cell is an activated B cell, i.e., a B cell which has encountered an antigen. The term "B cell response" is intended to include a response of a B cell to a stimulus. The stimulus can be a soluble stimulus such as an antigen, a lymphokine, or a growth factor or a combination thereof. Alternatively, the stimulus can be a membrane bound molecule, such as a receptor on T helper (Th) cells, e.g., CD28, CTLA4, gp39, or an adhesion molecule. Since a change in a B cell, such as a change occuring during the process of B cell maturation or activation is mediated by extracellular factors and membrane bound molecules, a response of a B cell is intended to include any change in a B cell, such as a change in stage of differentiation, secretion of factors, e.g., antibodies. Thus, a modulation of a B cell response can be a modulation of B cell aggregation, a modulation of B cell differentiation, such as differentiation into a plasma cell or into a memory B cell, or a modulation of cell viability. In a preferred embodiment, the invention provides a method for stimulating the differentiation of a B cell from a lymphoblast to a centrocyte. In another preferred embodiment, the invention provides a method for modulating B cell aggregation, such as homotypic B cell aggregation. In another embodiment, the invention provides a method for modulating B cell survival. In yet another preferred embodiment, the invention provides a method for modulating production of antibodies by B cells. In a further embodiment, the invention provides a method for modulating proliferation of B cells.

Other aspects of the invention pertain to methods for identifying agents which modulate, e.g., inhibit or activate/stimulate, a p62 polypeptide or expression thereof. Also contemplated by the invention are the agents which modulate, e.g., inhibit or activate/stimulate p62 polypeptides or p62 polypeptide expression and which are identified according to methods of the present invention. In one embodiment, these methods include contacting a first polypeptide comprising an SH2 domain of $p56^{lck}$ with a second polypeptide comprising a p62 polypeptide and an agent to be tested and determining binding of the second polypeptide to the first polypeptide. Inhibition of binding of the first polypeptide to the second polypeptide indicates that the agent is an inhibitor of a p62 polypeptide. Activation of binding of the first polypeptide to the second polypeptide indicates that the agent is an activator/stimulator of a p62 polypeptide. Methods for testing the binding of an agent to the SH2 domain of $p56^{lck}$ are described herein.

In another embodiment, these methods include contacting a p53 protein, p53 analog, derivative or active fragment, under conditions which promote ubiquitination of the p53 protein, p53 analog, derivative or active fragment, with an agent to be tested and determining p53 ubiquitination level in the presence of the agent. An activation of p53 ubiquitination indicates that the agent is an inhibitor of a p62 polypeptide. An inhibition of p53 ubiquitination indicates that the agent is an activator of a p62 polypeptide. To measure p53 ubiquitination, a skilled artisan can follow the protocol set forth in Scheffner et al. (1993) *Cell* 75:495. In particular, p53 ubiquitination can measured by using in vitro translated human wild type p53 as a p53 source. Human E6AP, papilloma E6 and HeLa p62 can then be expressed as GST fusion proteins in *E. coli*. Other components used in the system to measure p53 ubiquitination include E1 and UBC8, which can be expressed in *E. coli* using a pET expression system as previously described (Hatfield and Vierstra (1992) *J. Biol. Chem.* 267:14799). A 50 ml total reaction mixture typically contains 4 ml of p53, 100–200 ng of E6, p62, E6AP, E1 and UBC8 in a reaction buffer. The reaction buffer typically includes 25 mM Tris, pH7.5, 50 mM NaCl, 5 mM $MgCl_2$, 0.1 mM DTT, 5 mM ubiquitin, and 5 mMATPgS. The reaction mixture is generally incubated at 30° C. for two hours and stopped with the addition of SDS-buffer. The reaction products are separated on a 10% SDS-PAGE gel and visualized by fluorography to determine ubiquitination of p53.

In yet another embodiment, these methods include contacting a first polypeptide comprising ubiquitin, a ubiquitin analogs derivative or active fragment, with a second polypeptide comprising a p62 polypeptide and an agent to be tested and determining binding of the second polypeptide to the first polypeptide. Inhibition of binding of the first polypeptide to the second polypeptide indicates that the agent is an inhibitor of a p62 polypeptide. Activation of binding of the first polypeptide to the second polypeptide indicates that the agent is an activator of a p62 polypeptide. Methods for testing the binding of an agent to ubiquitin are described herein.

In yet another embodiment, these methods include contacting a first polypeptide comprising a p53 protein, p53 analog, derivative or active fragment, with a second polypeptide comprising a p62 polypeptide and an agent to be tested, measuring the level of p53 degradation in the presence of the agent, and comparing the level of p53 degradation in the presence of the agent to level of p53 degradation in the absence of the agent. An increase in the level of p53 degradation in the presence of the agent indicates that the agent is an inhibitor of a p62 polypeptide. A decrease in the level of p53 degradation in the presence of the agent indicates that the agent is an activator of a p62 polypeptide. p53 degradation can be measured using the method described in Scheffner et al. (1990) Cell 63:1129–1136). For example, p53 degradation can be measured by using two milliliters of in vitro translated human wild type p53 and ten milliliters of papilloma virus E6-GST fusion protein incubated together at 25° C. for three hours in 25 mM Tris, pH 7.5, 50 mM NaCl and 2 mM DTT. Reaction mixtures also contain a total of about ten milliliters of rabbit reticulolysate per forty milliliters of reaction mixture. The reactions are stopped with the addition of SDS-buffer and samples are separated on 10% SDS-PAGE gels and visualized by fluorography to determine p53 degradation. p53 degradation can also be measured using a reaction mixture which include E6 and E6AP-supplemented wheat-germ lysate or a reaction mixture containing purified E1, appropriate E2, E6, and E6AP. Scheffner et al. (1993) Cell 75:495–505.

V. p160 Nucleic Acids. Polypeptides. and Methods of Use

As described herein, the present invention is also based on the discovery of a second family of polypeptides, designated herein as p160 polypeptides. The p160 polypeptides act downstream from the p62 polypeptides. Specifically, p160 polypeptides of the invention are capable of binding to the p62/p56$^{lck}$ complex to thereby modulate Lck function in a similar manner as described herein for the p62 polypeptides, The p160 polypeptides activate transcription. p160 polypeptides include leucine zipper domains which are found in some transcription factors, e.g., jun, fos, myc, CEBP, etc. The leucine zipper domain in the 160.1 polypeptide comprises amino acids 3 to 138 of the amino acid sequence of FIG. 9, SEQ ID NO:7 (encoded by nucleotides 447–888 of the nucleotide sequence of FIG. 8, SEQ ID NO:6) and the leucine zipper domain of the p160.2 polypeptide comprises amino acids 3 to 138 of the amino acid sequence of FIG. 11, SEQ ID NO:9 (encoded by nucleotides 447–888 of the nucleotide sequence of FIG. 10, SEQ ID NO:8). The p160 polypeptides also include proline/lysine rich and glutamic acid rich regions. For example, the p160.1 polypeptide includes a proline/lysine rich region at amino acid residues 740 to 868 of the amino acid sequence of FIG. 9, SEQ ID NO:7 (encoded by nucleotides 2656 to 3042 of the nucleotide sequence of FIG. 8, SEQ ID NO:6). The p160.2 polypeptide includes a proline/lysine rich region at amino acid residues 510 to 638 of the amino acid sequence of FIG. 11, SEQ ID NO:9 (encoded by nucleotides 1966 to 2352 of the nucleotide sequence of FIG. 10, SEQ ID NO:8). The glutamic acid rich regions of the p160.1 and p160.2 polypeptides appear at amino acid residues 884 to 1100 of the amino acid sequence of FIG. 9, SEQ ID NO:7 (encoded by nucleotides 3088 to 3732 of the nucleotide sequence of FIG. 8, SEQ ID NO:6) and 654 to 870 of the amino acid sequence of FIG. 11, SEQ ID NO:9 (encoded by nucleotides 2398 to 3032 of the nucleotide sequence of FIG. 10, SEQ ID NO:8).

The p160 polypeptides also contain regions which are homologous to regions found in other transcription factors such as oct-2. Specifically, the p160 polypeptides activate transcription of a variety of genes upon, for example, activation of p62. The genes which are transcribed in response to p160 activation likely include those which are involved in T or B cell development/differentiation, T or B cell activation, and production of T or B cell-specific factors, e.g., lymphokines and antibodies, respectively. The p160 polypeptides of the present invention have also been found to be substrates for serine/threonine kinase activity. A plasmid containing the full length nucleotide sequence (as shown in FIG. 8, SEQ ID NO:6) encoding the first p160 polypeptide (also designated herein as p160.1) was deposited with the American Type Culture Collection (ATCC) 10801 University Boulevard, Manassas, Va. 20110-2209 on Dec. 19, 1995 and was assigned ATCC Accession Number 97385. A second plasmid containing the full length nucleotide sequence (as shown in FIG. 10, SEQ ID NO:8) encoding the second p160 polypeptide (also designated herein as p160.2) was deposited with the American Type Culture Collection (ATCC) 10801 University Boulevard, Manassa, Va. 20110-2209 and was assigned ATCC Accession Number 97384. A comparison of the nucleotide sequences of the first p160 polypeptide and the second p160 polypeptide is shown in FIG. 18. A comparison of the amino acid sequences of the first p160 polypeptide and the second p160 polypeptide is shown in FIG. 19.

Accordingly, the present invention pertains to isolated nucleic acid molecules comprising a nucleotide sequence, or a portion or fragment thereof, shown in FIG. 8, SEQ ID NO:6 or FIG. 10, SEQ ID NO:8 or have at least about 60%, more preferably at least about 70%, yet more preferably at least about 80%, and most preferably 90% or more overall sequence identity with the nucleotide sequence shown in FIG. 8, SEQ ID NO:6 or FIG. 10, SEQ ID NO:8 or a portion or fragment thereof. These nucleotide sequences represent two isoforms of the p160 nucleic acid. The second p160 polypeptide, p160.2 is missing two exons which are included in the first p160 polypeptide, p160.1. These exons are located at amino acid residues 210–354 of FIG. 9, SEQ ID NO:7, which are encoded by nucleotides 1066–1500 of FIG. 8, SEQ ID NO:6 and at amino acid residues 508–592 of FIG. 9, SEQ ID NO:7, which are encoded by nucleotides 1959–2213 of FIG. 8, SEQ ID NO:6. In other embodiments, the isolated nucleic acid molecules comprise nucleotide sequences which encode an amino acid sequence, or portion or fragment thereof, shown in FIG. 9, SEQ ID NO:7 or FIG. 11, SEQ ID NO:9 or have at least about 60%, more preferably at least about 70%, yet more preferably at least about 80%, and most preferably 90% or more overall sequence identity with the amino acid sequence, or portion or fragment thereof, shown in FIG. 9, SEQ ID NO:7 or FIG. 11, SEQ ID NO:9. The p160 nucleic acid molecules of the present invention can be contained within vectors as described herein. Such vectors can be introduced into host cells as described herein.

The present invention also pertains to isolated polypeptides having a p160 activity. p160 activities parallel the activities set forth herein for p62. Thus, polypeptides having p160 activity can have one or more of the activities set forth herein for p62 polypeptides. Preferred polypeptides include those which comprise an amino acid sequence shown in FIG. 9, SEQ ID NO:7 or FIG. 11, SEQ ID NO:9 or a fragment or portion thereof. The p160 polypeptides of the present invention can be included in fusion proteins, used to generate antibodies, and used in methods for modulating cell proliferation, methods for modulating leukocyte activity, and methods for identifying modulators of p160 polypeptides as described herein for p62 polypeptides.

VI. Applications of the Invention

The invention provides a method for modulating B cell activity in a subject. In one embodiment, the invention provides a method for stimulating a B cell response. Stimulation of a B cell response can result in increased B cell aggregation, increased B cell differentiation and/or increased B cell survival. The B cells can, for example, be stimulated to differentiate from a lymphoblast to a centroblast or centrocyte and thereby stimulate the differentiation of B cells into either antibody secreting plasma cells or memory B cells. In another embodiment, the invention provides a method for stimulating a T cell response, such as T cell proliferation. In a preferred embodiment, the invention provides a method for stimulating a B cell response and a T cell response, such as T cell proliferation. It will be appreciated that it is particularly advantageous to stimulate both B cells and T cells for most applications.

A p62 polypeptide or an agent which stimulates a p62 polypeptide or expression thereof can also be used for treating disorders in which boosting of a B cell response is beneficial. Such disorders include infections by pathogenic microorganisms, such as bacteria, viruses, and protozoans. Preferred disorders for treating according to the method of the invention include extracellular bacterial infections, wherein bacteria are eliminated through opsonization and phagocytosis or through activation of the complement. Other preferred infections that can be treated according to the method of the invention include viral infections, including infections with an Epstein-Barr virus or retroviruses, e.g., a human immunodeficiency virus.

In another embodiment of the invention, p62 polypeptides and/or agents which stimulate p62 polypeptides can be administered to a subject having an antibody deficiency disorder resulting, for example, in recurrent infections and hypogammaglobulinemia (Ochs et al. (1989) Disorders in Infants and Children, Stiehm (ed.) Philadelphia, W. B. Sanders, pp 226–256). These disorders include common variable immunodeficiency (CVI), hyper-IgM syndrome (HIM), and X-linked agammaglobulinemia (XLA). Some of these disorders, e.g., HIS, are caused by a mutation in the CD40 ligand, gp39, on the T cell and administration of a p62 polypeptide or an agent which stimulates a p62 polypeptide or expression thereof would thus compensate for at least some of the B cell deficiencies, such as stimulation of B cell differentiation.

Furthermore, upregulation of a B cell response is also useful for treating a subject with a tumor. In one embodiment, a p62 polypeptide or an agent which stimulates a p62 polypeptide is administered at the site of the tumor. In another embodiment, a p62 polypeptide and/or an agent which stimulates a p62 polypeptide is administered systemically.

In another embodiment, the invention provides a method for stimulating B cells in culture, such as hybridoma cells. In a preferred embodiment, stimulation of the population of B cells results in increased antibody production. Thus, a p62 polypeptide or an agent which stimulates a p62 polypeptide can be added at an effective dose to a B cell culture, such as a hybridoma, such that antibody production by the B cells is enhanced. The effective dose of the p62 polypeptide or the agent which stimulates a p62 polypeptide to be added to the culture can easily be determined experimentally. This can be done, for example, by adding various amounts of the polypeptide or agent to a constant amount of B cells, and by monitoring the amount of antibody produced, e.g., by ELISA. The effective dose corresponds to the dose at which highest amounts of antibodies are produced.

In yet another embodiment, a p62 polypeptide or an agent which stimulates a p62 polypeptide is administered together with a hybridoma into the peritoneal cavity of a mouse, such that the amount of antibody produced by the hybridoma is increased.

In another embodiment of the invention, a T cell is contacted with a p62 polypeptide or an agent which stimulates a p62 polypeptide and a primary activation signal, such that T cell proliferation is increased. The primary activation signal can be an antigen, or a combination of antigens, such that proliferation of one or more clonal populations of T cells is stimulated. Alternatively the primary activation signal can be a polyclonal agent, such as an antibody to CD3, such that T cell proliferation is stimulated in a non clonal manner.

In one embodiment, the invention provides a method for expanding a population of T cells ex vivo. Accordingly, primary T cells obtained from a subject are incubated with a p62 polypeptide or an agent which stimulates a p62 polypeptide and a primary activation signal. Following activation and stimulation of the T cells, the progress of proliferation of the T cells in response to continuing exposure to the p62 polypeptide or the agent which stimulates a p62 polypeptide is monitored. When the rate of T cell proliferation decreases, the T cells are reactivated and restimulated, such as with additional anti-CD3 antibody and a p62 polypeptide or an agent which stimulates a p62 polypeptide in the T cell, to induce further proliferation. The monitoring and restimulation of the T cells can be repeated for sustained proliferation to produce a population of T cells increased in number from about 100- to about 100,000-fold over the original T cell population. Methods for stimulating the expansion of a population of T cells are further described in the published PCT application PCT/US94/06255.

The method of the invention can be used to expand selected T cell populations for use in treating an infectious disease or cancer. The resulting T cell population can be genetically transduced and used for immunotherapy or can be used for in vitro analysis of infectious agents such as HIV. Proliferation of a population of $CD4^+$ cells obtained from an individual infected with HIV can be achieved and the cells rendered resistant to HIV infection. Following expansion of the T cell population to sufficient numbers, the expanded T cells are restored to the individual. The expanded population of T cells can further be genetically transduced before restoration to a subject. Similarly, a population of tumor-infiltrating lymphocytes can be obtained from an individual afflicted with cancer and the T cells stimulated to proliferate to sufficient numbers and restored to the individual. In addition, supernatants from cultures of T cells expanded in accordance with the method of the invention are a rich source of cytokines and can be used to sustain T cells in vivo or ex vivo.

In another embodiment of the invention, T cell proliferation is stimulated in vivo. In a preferred embodiment, a p62 polypeptide or an agent which stimulates a p62 polypeptide in the T cell is administered to a subject, such that T cell proliferation in the subject is stimulated. The subject can be a subject that is immunodepressed, a subject having a tumor, or a subject infected with a pathogen. The agent of the invention can be administered locally or systemically. The agent can be administered in a soluble form or a membrane bound form. Additional applications for an agent capable of providing a costimulatory signal to T cells, such that their proliferation is stimulated, are described in the published PCT applications PCT/US94/13782 and PCT/US94/08423, the content of which are incorporated herein by reference.

Inhibitors of p62 can also be used to reduce B cell and/or T cell responses in autoimmune diseases which involve autoreactive B and/or T cells. Accordingly, administration of an inhibitor of p62 to a subject can be used for treating a variety of autoimmune diseases and disorders having an autoimmune component, including diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

The efficacy of a p62 inhibitor in preventing or alleviating autoimmune disorders can be determined using a number of well-characterized animal models of human autoimmune diseases. Examples include murine experimental autoimmune encephalitis, systemic lupus erythmatosis in MRL/lpr/ lpr mice or NZB hybrid mice, murine autoimmune collagen arthritis, diabetes mellitus in NOD mice and BB rats, and murine experimental myasthenia gravis (see Paul ed., *Fundamental Immunology*, Raven Press, New York, 1989, pp. 840–856).

VII. Pharmaceutical Compositions

The p62 polypeptides, portions or fragments thereof, and other agents described herein can be incorporated into pharmaceutical compositions suitable for administration. Such compositions typically comprise the polypeptide, a portion or fragment thereof, or agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In one embodiment, the agents of the invention can be administered to a subject to modulate a B cell response in the subject, e.g., for stimulating the clearance of a pathogen from the subject. The agents are administered to the subjects in a biologically compatible form suitable for pharmaceutical administration in vivo. By "biologically compatible form suitable for administration in vivo" is meant a form of the agents, e.g., protein to be administered in which any toxic effects are outweighed by the therapeutic effects of the agent. Administration of a therapeutically active or therapeutically effective amount of an agent of the present invention is defined as an amount effective, at dosages and for periods of time necessary to achieve the desired result. For example, a therapeutically active amount of a p62 molecule can vary according to factors such as the disease state, age, sex, and weight of the subject, and the ability of agent to elicit a desired response in the subject. Dosage regimens may be adjusted to provide the optimum therapeutic response. For example, several divided doses may be administered daily or the dose may be proportionally reduced as indicated by the exigencies of the therapeutic situation.

The agent may be administered in a convenient manner such as by injection (subcutaneous, intravenous, etc.), oral administration, inhalation, transdermal application, or rectal administration. Depending on the route of administration, the agent may be coated in a material to protect it from the action of enzymes, acids and other natural conditions which may inactivate the agent. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

To administer an agent by other than parenteral administration, it may be necessary to coat the agent with, or co-administer the agent with, a material to prevent its inactivation. For example, a p62 molecule may be administered to a subject in an appropriate carrier or diluent co-administered with enzyme inhibitors or in an appropriate carrier such as liposomes. Pharmaceutically acceptable diluents include saline and aqueous buffer solutions. Enzyme inhibitors include pancreatic trypsin inhibitor, diisopropylfluorophosphate (DEP) and trasylol. Liposomes include water-in-oil-in-water emulsions as well as conventional liposomes (Strejan et al., (1984) *J. Neuroimmunol* 7:27). Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the agent in the required amount in an appropriate solvent with one or a combination of ingredients enumerated above, as required, followed by filtered sterilization. Generally, dispersions are prepared by incorporating the agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (e.g., peptide) plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of individuals.

The present invention is further illustrated by the following examples which in no way should be construed as being further limiting. The contents of all cited references (including literature references, issued patents, published patent applications, and co-pending patent applications) cited throughout this application are hereby expressly incorporated by reference.

EXAMPLES

Example I

Cloning of cDNA Encoding p62 Polypeptides p62 was purified from cell lysate of 300 liter culture of HeLa cells using GST.lckSH2 conjugated glutathione agarose beads as an affinity matrix followed by separation on the SDS-PAGE. Two major proteins (62 kD and 160 kD; p62 and p160 respectively) on the SDS-PAGE were transferred to PVDF membrane. Internal peptides of purified p62 were obtained by Lys-C digestion followed by reverse-phase HPLC. Five well resolved peptides peaks were subjected to automated Edman degradation to determine amino acid sequence. These five peptides had the following amino acid sequences:

```
pk5,   WLRK or IYIKE (SEQ ID NOs:10 and 11, respectively)

pk7,   LTPVSPESSSTEEK (SEQ ID NO:12)

pk50,  NVGESVAAALSPLGI(Q)VDIDVEHGGK (SEQ ID NO:13)

pk55,  VAALFPALRPGGFQAHYRDEDGDLVAFSSDEELTMAMSYVK (SEQ ID NO:14)
```

A HeLa Uni-Zap cDNA library (Stratagene, LaJolla, Calif.) was then screened using a degenerate oligonucleotide synthesized based on the internal peptide sequence of pk55. One of twenty seven positive clones isolated from the library was a full length cDNA (2,083 bp) containing a 1,320 bp open reading frame. Northern Blot analysis performed following standard protocols using a $^{32}$P-dCTP labelled probe derived from the p62 sequence. The mRNA sources used in the Northern analysis were (i) tissue blot membrane purchased from Clontech, Palo Alto, Calif.; and (ii) total or polyA mRNA purified from cultured HeLa cells, T cells (Jurkat, HPB-ALL and CEM) and B cells (Daudi and Raji). The Northern analysis showed that p62 is expressed ubiquitously in tissues observed including heart, brain, placenta, lung, liver, skeletal muscle, kidney, and pancreas and that the size of mRNA is around 2.0 kb confirming that the cDNA isolated is full length. The deduced amino acid sequence from the cloned p62 cDNA contains 440 amino acids including all five peptide sequences derived from protein sequencing.

In parallel, a Daudi B cell cDNA library was screened using the same oligonucleotide probe. A 1,977 bp long partial cDNA was obtained and sequenced. This cDNA has 88.5% identity in amino acid sequence and 77.5% identity in nucleotide sequence to the cDNA isolated from the HeLa cell library. A comparison of the two p62 nucleotide sequences is shown in FIG. 6. A comparison of the two p62 amino acid sequences is shown in FIG. 7.

Example II

Cloning of cDNA Encoding p160 Polypeptides p160 was purified from HeLa cell lysates using Lck SH2 affinity chromatography. The purified protein was subjected to Lys-C digestion and the resulting peptides were purified on HPLC. Amino acid sequences of seven well separated peptides were determined and are set forth below:

pk5,  GSPDGSLQTGKPSAPK(S) (SEQ ID NO:15)

pk9,  LRSPRGSPDGSLQTGK (SEQ ID NO:16)

pk14, LDVGEAMAP(Q) (SEQ ID NO:17)

pk36, EQDDTAAVLADFID (SEQ ID NO:18)

pk39, VQPEPEPEPGLLLEVEEPGTEEERGADD (SEQ ID NO:19)

pk43, VQPPPETPAEEEMETETEAEALQEKE(G)QDD(A)A(A)ML (SEQ ID NO:20)

pk47, VQPEPEPEPGLLLEVEEPGT (SEQ ID NO:21)

A HeLa cell cDNA (Stratagene, LaJolla Calif.) was screened with $^{32}$P-labeled degenerate oligonucleotide probes synthesized based on the pk36 peptide sequence shown above. Positives were plaque purified and sequenced. All of the positives had the same sequence at the C-terminus but differed in length at the N-terminus. The length of the longest clone obtained was 1.3 kb. A probe based on the N-terminal 300 base pairs of the 1.3 kb probe was used to rescreen the cDNA library. The second screening resulted in the isolation of an overlapping clone with an extension of 1.9 kb. Construction of the full length clone using internal restriction sites resulted in a 3.2 kb clone (encoding the second p160 polypeptide designated herein as p160.2). Further screening of the cDNA library with a probe which included the N-terminus of the 3.2 kb clone resulted in the isolation of an isoform of p160 which was 3.9 kb in length (designated herein as p160.1).

Example III

Biochemical Characterization of p62

The following materials and methods were used throughout this Example:
Cell Culture, Transfection, and Metabolic Labeling
HeLa and CD4$^+$HeLa cells (Shin, J. et al. (1990) *EMBO J.* 9:425–434) and Jurkat T cells were maintained in 10% fetal bovine serum supplemented DMEM and RPMI respectively. For v-src expression, HeLa cells were transiently transfected with 20 mg of cDNA per 10 cm plate using the calcium phosphate precipitation method (Chen, C. et al. (1987) *Mol. Cell Biol.* 7:2745–2752). For metabolic labeling, cells were incubated with 100 mCi/ml $^{35}$S-methionine in methionine free DMEM for one hour.
Site Directed Mutagenesis, GST Fusion Protein Production, and Protein Precipitation
Site-directed mutagenesis was performed on uracil-containing phage DNA (Kunkel, T. (1985) *Proc. Natl. Acad. Sci USA* 82:488–492) using the M13 Muta-Gene kit (Bio-Rad). GST fusion proteins were produced as described elsewhere (Joung, I. et al. (1995) *Proc. Natl. Acad. Sci. USA* 92:5778–5782; Payne, G. et al. (1993) *Proc. Natl. Acad. Sci. USA* 90:4902–4906). HeLa cell lysate was prepared and used for GST fusion protein binding as described (Joung, I. et al. (1995) *Proc. Natl. Acad. Sci. USA* 92:5778–5782). Phosphatase inhibitors were added as indicated in the Brief Description of the Drawings section. For the competition assay, the stated amounts of phosphotyrosyl peptides were added to the lysates during incubation. After washing three times with lysis buffer, bound proteins were eluted by boiling in SDS-PAGE loading buffer. After SDS-PAGE, $^{35}$S-methionine labeled proteins on the gel were fluorographed, dried, and visualized by autoradiography. For Western analysis, proteins were electrotransferred to nitrocellulose and immunoblotted using 4G10 monoclonal antibody and HRP-conjugated Goat anti-Mouse antibody. Signals were developed using enhanced chemiluminescence (Amersham).

Figure 12B:
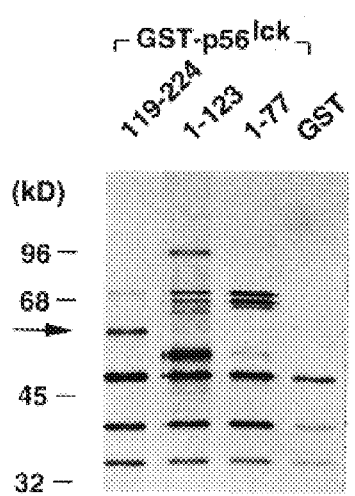

Results of Biochemical Characterization of p62
A. p62 Binds to the p56$^{lck}$ SH2 Domain in a Phosphotyrosine-Independent Manner
GST and GST fusion proteins Of p56$^{lck}$ subdomains (FIG. 12A) containing unique N-terminal region (1–77), unique N-terminal region and SH3 domain (1–123), and SH2 domain (119–224) were incubated with lysates from $^{35}$S-methionine labelled CD4+ HeLa cells. Bound proteins were separated on 9% SDS-PAGE, fluorographed, and detected by autoradiography. Each subdomain of p56$^{lck}$ can specifically bind to proteins from this HeLa cell lysate (FIG. 12B). In FIG. 12B, a 62 kD protein (p62) that bound specifically to the S112 domain is marked with an arrow. GST 119–224 (the SH2 domain alone) uniquely precipitated a 62 kD protein (p62) that was not precipitated by any of the other proteins (FIG. 12B). The binding of p62 to the p56$^{lck}$ SH2 domain was also observed in cell lysate of non-activated Jurkat T cells.

Figure 12C:
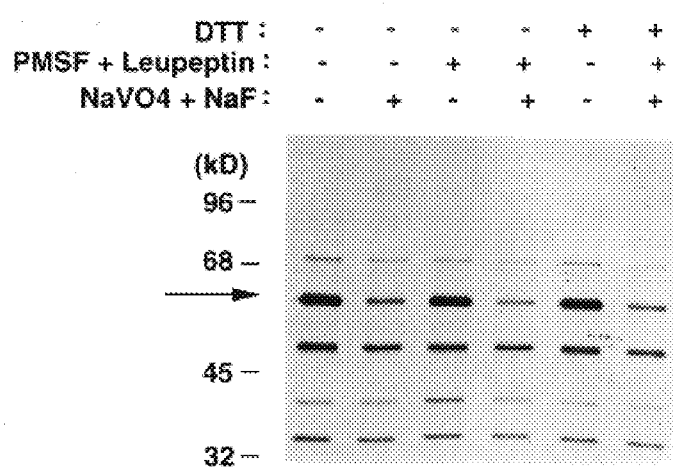

$^{35}$S-methionine labelled HeLa cells were lysed in the presence or absence of phosphatase inhibitors (sodium vanadate (NaVO$_4$) and sodium fluoride (NaF)), protease inhibitors (PMSF and Leupeptin), or reducing reagent (DTT). The lysates were incubated with GST.119–224, and bound proteins were analyzed by SDS-PAGE. p62 could not be detected by immunoblotting using 4G10 anti-phosphotyrosine antibody (see FIG. 15). Furthermore, p62 binding to the SH2 domain was enhanced in cell lysates prepared in the absence of phosphatase inhibitors, NaVO$_4$ and NaF, while the binding was insensitive to the lack of protease inhibitors and reducing reagents (FIG. 12C). These data suggest that p62 binding to the p56$^{lck}$ SH2 domain is phosphotyrosine (pY)-independent.

B. p62 Binds to a Specific Site Other than the Phosphotyrosine-dependent Binding Site of the SH2 Domain.

$^{35}$S-methionine labelled HeLa cells were lysed in the presence of phosphatase inhibitors (NaVO$_4$ and NaF). The lysates were incubated with increasing concentrations of phosphotyrosyl peptides; pY324, pY505, pY771, and pY536. Bound p62 was separated on 9% SDS-PAGE, fluorographed, and detected by autoradiography.

Two phosphotyrosyl peptides, pY324 and pY505 (derived from polyoma middle T antigen (EPQpYEEIPIYL) and from the C-terminal negative regulatory region of p56$^{lck}$ (TEGQpYQPQPA) respectively) bind strongly and specifically to the p56$^{lck}$ SH2 domain (Payne, G. et al. (1993) *Proc. Natl. Acad. Sci. USA* 90:4902–4906). These two specific peptides competed away p62 binding to GST.119–224 at 1 mM and 15 mM of pY324 and pY505 peptides respectively (FIG. 13). Phosphotyrosyl peptides that bind poorly (pY771 (SSNpYMAPYDNY) and pY536 (ESEpYGNITYPP)), however, did not affect p62 binding to GST.119–224. Thus, pY-independent binding of p62 to the p56$^{lck}$ SH2 domain is interrupted by binding of the phosphotyrosyl peptide to the SH2 domain.

Figure 14A:
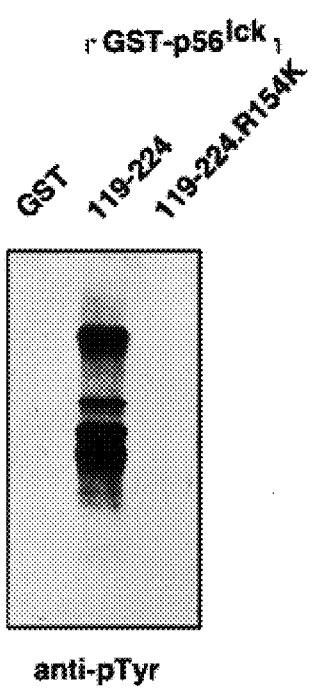
FIGS. 14A–14B depict the results of experiments demonstrating distinct mechanisms for phosphotyrosine-dependent and -independent protein binding to the SH2 domain.
Figure 14B:
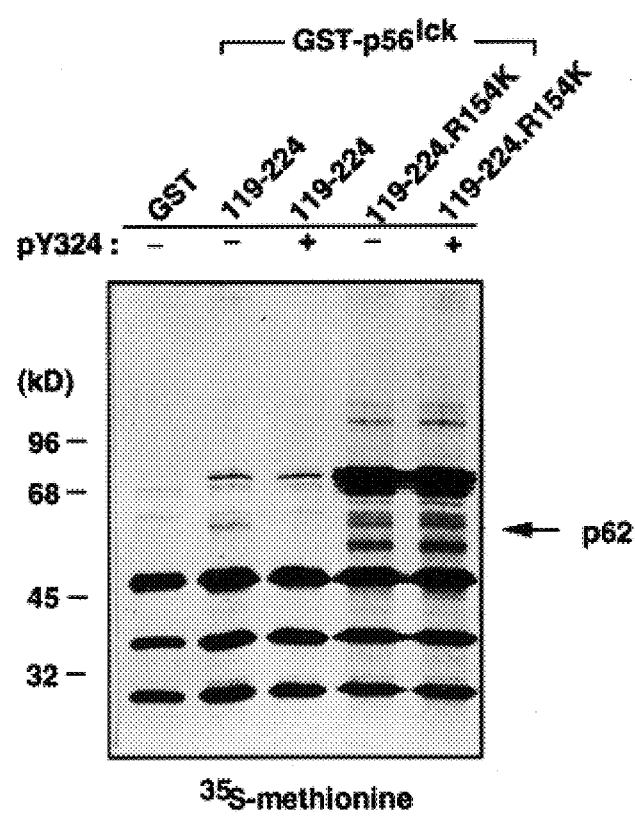

An arginine residue (Arg154 of p56$^{lck}$) that is conserved in all SH2 domains and is a part of the pY binding pocket (Mayer, B. et al. (1992) *Mol. Cell Biol.* 12:609–618; Eck, M. et al. (1993) *Nature* 362:87–91) was mutated to lysine (GST.119–224.R154K). Specifically, GST alone, GST.119–224, and GST.119–224.R154K were incubated with v-src transfected HeLa cell lysate in the presence of phosphatase inhibitors. Bound proteins were analyzed by immunoblotting with anti-phosphotyrosine antibody (FIG. 14A). GST alone, GST.119–224, and GST.119–224.R154K were incubated with $^{35}$S-methionine labeled HeLa cell lysate in the presence of phosphatase inhibitors. Competition of p62 binding to the SH2 domain by phosphotyrosyl peptide was measured by adding 10 mM pY324 peptide to the incubation mixture. Bound proteins were analyzed by SDS-PAGE. The mutant did not bind to phosphotyrosyl proteins (FIG. 14A). The binding of p62, however, was unaltered in the GST.119–224.R154K protein and was not inhibited by high concentration of pY324 (FIG. 14B). These data suggest that p62 binds to a specific site other than the pY-dependent binding site of the SH2 domain.

Figure 15A:
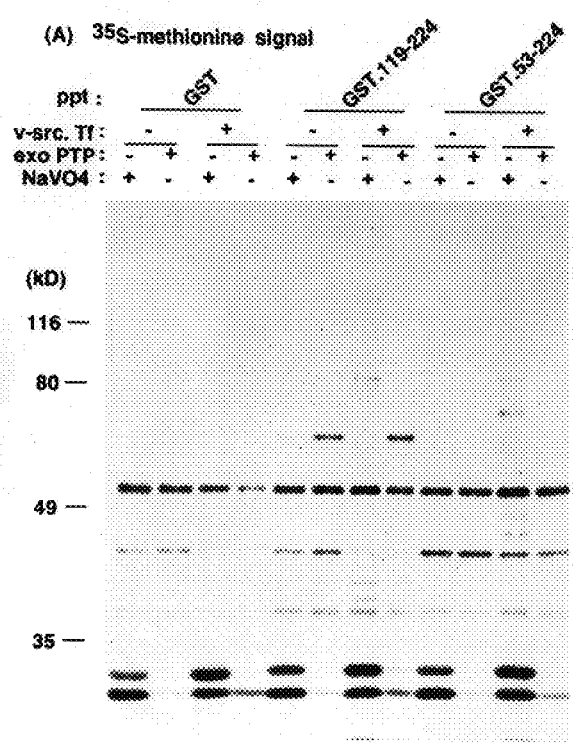
FIGS. 15A–15C depict the results of experiments demonstrating regulation of p62 binding to the p56$^{lck}$ SH2 domain by Ser59 phosphorylation of p56$^{lck}$.
Figure 15B:
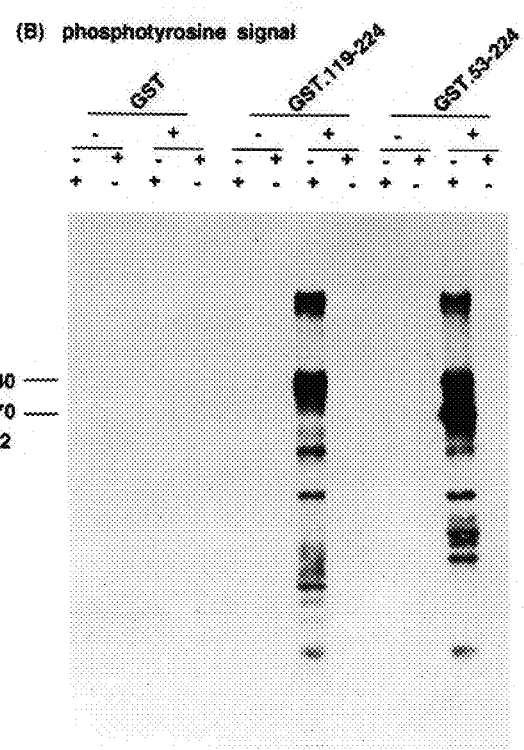

C. Phosphotyrosine-Independent Binding of p62 to the p56$^{lck}$ SH2 Domain is also Regulated by Phosphorylation of Ser59 of p56$^{lck}$ The Ser59 phosphorylation site in the unique N-terminal region affects the binding affinity and specificity of the SH2 domain of p56$^{lck}$ for phosphotyrosyl proteins (Joung, I. et al. (1995) *Proc. Natl Acad. Sci. USA* 92:5778–5782; Winkler, D. et al. (1993) *Proc. Natl. Acad. Sci. USA* 90:5176–5180). The effect of the Ser59 phosphorylation site on p62 binding to the p56$^{lck}$ SH2 domain was therefore examined by comparing protein binding to GST.119–224 and to GST.53–224 which contains the Ser59 phosphorylation site (amino acid residues 53 to 64). HeLa cells transfected with v-src or vector alone were labelled with $^{35}$S-methionine and lysed in the presence or absence of phosphatase inhibitors. Samples that were lysed in the absence of phosphatase inhibitors were treated with exogenous recombinant phosphatase mixture (recombinant catalytic fragments of the tyrosine phosphatases LAR, CD45, and SHPTP-1). The lysates were incubated with GST alone, GST.119–224, and GST.53–224. Bound proteins were separated on 8% SDS-PAGE, electrotransferred to nitrocellulose, and detected by autoradiography (FIG. 15A). In FIG. 15B, the same membrane in FIG. 15A was immunoblotted with anti-phosphotyrosine antibody (4G10). p62 and two phosphotyrosyl proteins (pp70 and pp80) are marked. As expected, GST.119–224 precipitated a unique set of phosphotyrosyl proteins (pp130 and pp80) from v-src transfected cell lysate in the presence of phosphatase inhibitors, while GST.53–224 precipitated phosphotyrosyl proteins pp70 as well as pp130 and pp80 (Joung, I. et al. (1995) *Proc. Natl Acad Sci. USA* 92:5778–5782). However, in the absence of phosphatase inhibitors, GST.119–224, but not GST.53–224 or GST alone, strongly bound to $^{35}$S-labeled p62 in both v-src transfected and untransfected cell lysates (FIG. 15A).

Figure 15C:
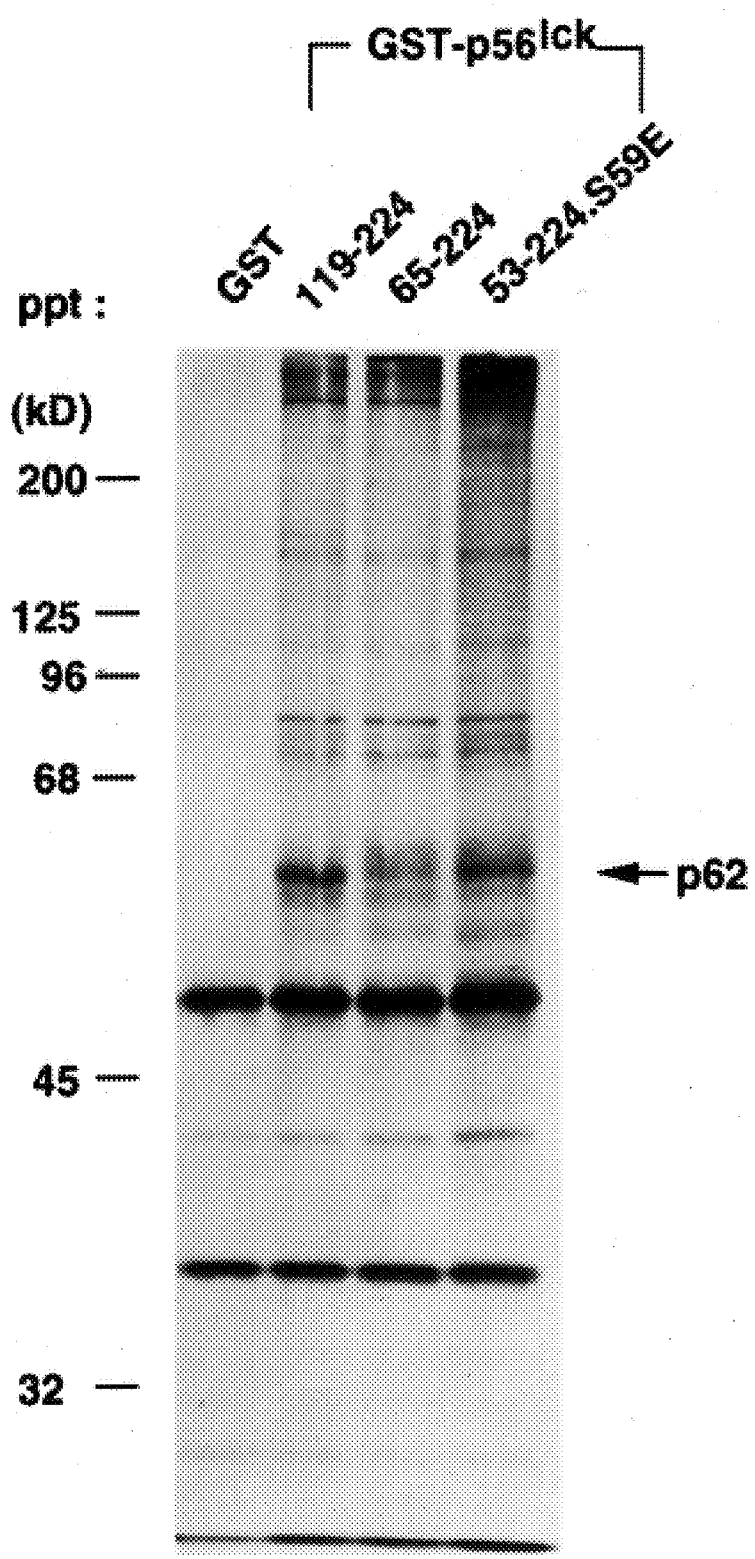

HeLa cells were labelled with $^{35}$S-methionine, lysed in the absence of phosphatase inhibitors, incubated with GST alone, GST.119–224, GST.65–224, and GST.53–224.S59E. Bound proteins were separated on 9% SDS-PAGE, fluorographed, and detected by autoradiography (FIG. 15C). Binding of the SH2 domain in GST.53–224 to p62 was restored by truncation of the unique N-terminal region (using GST.65–224 which contains SH3 and SH2 domains only) or by mutation of Ser59 to Glu59 of the protein (using GST.53–224.S59E) (FIG. 15C and compare to FIG. 15A). These data suggest that the pY-independent binding of p62 to the p56$^{lck}$ SH2 domain is also regulated by phosphorylation of Ser59, for which the S59E mutation is a substitution.

D. p62 is a Novel Protein and also Binds to p120 ras-GAP

Figures 16A, 16B:
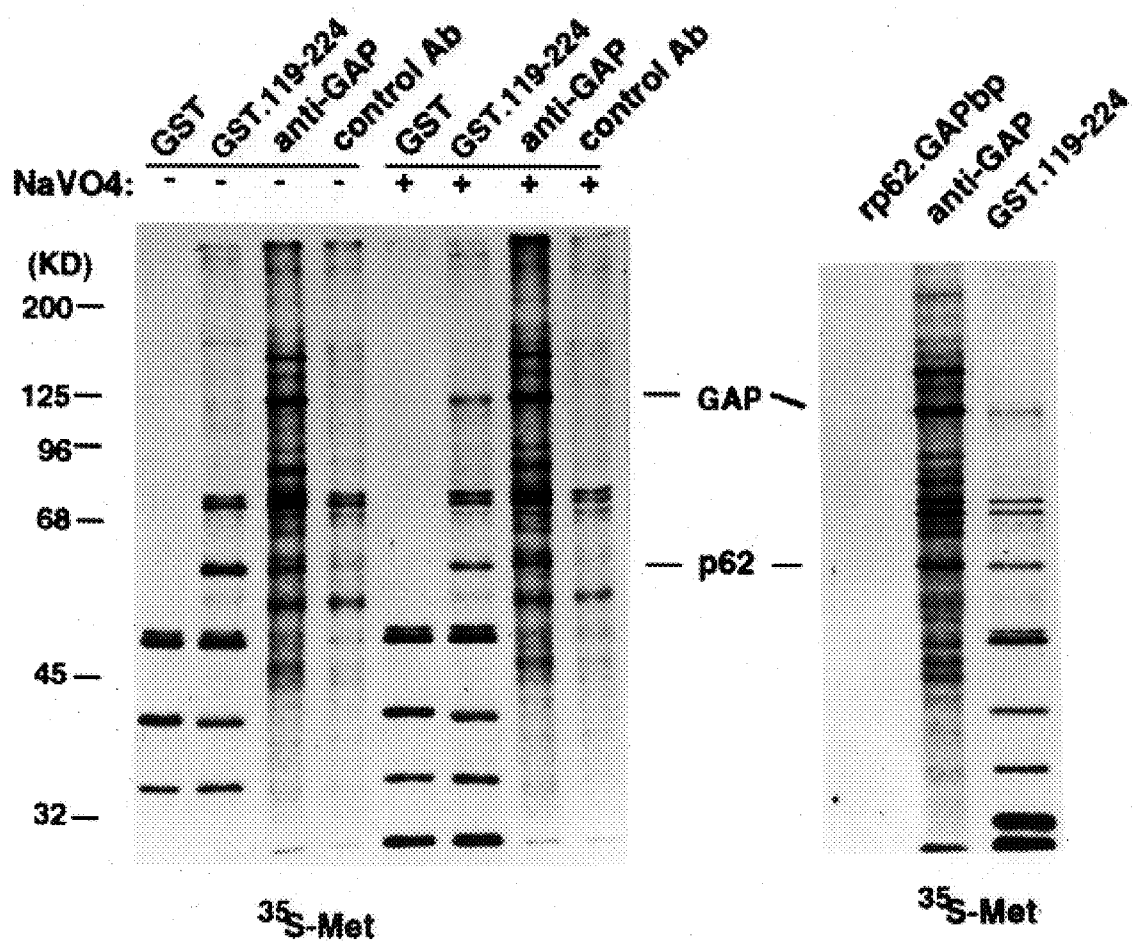
FIGS. 16A–16E depicts the results of experiments demonstrating that p62 is a novel polypeptide which binds to p120 ras-GAP.
Figures 16C, 16D, 16E:
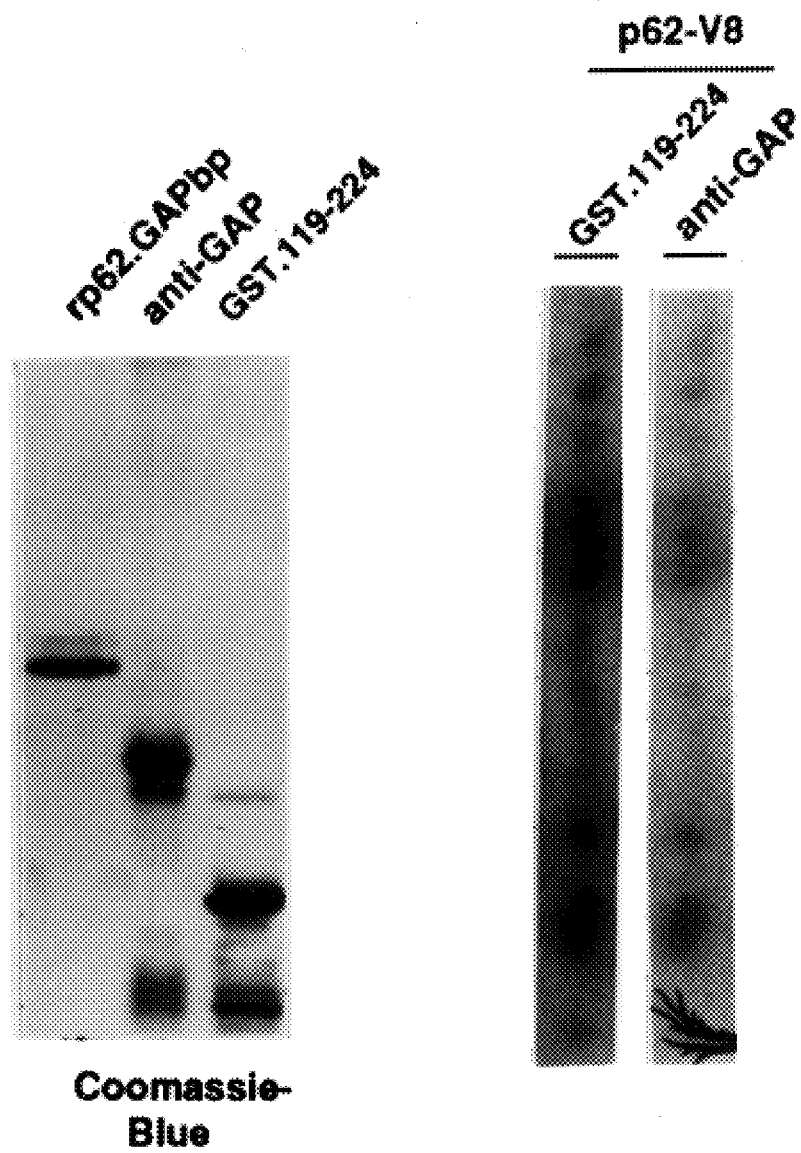

A protein of the same molecular weight as p62 (62 kD) was precipitated by an antiserum raised against p120 ras-GAP but not by control rabbit serum (FIG. 16A) or by antibodies against PI-3 kinase, MAP kinase, CD4, or PLC-g. $^{35}$S-methionine labelled HeLa cells were lysed in the presence or absence of phosphatase inhibitors. The lysates were incubated with GST alone or with GST.119–224. Alternatively, the lysates were immunoprecipitated with anti-GAP antibody or with a preimmune serum. Bound proteins were separated on 9% SDS-PAGE, fluorographed, and detected by autoradiography (FIGS. 16B and 16C). Recombinant p62 GAP binding protein (rp62$^{GAPbP}$) was run on SDS-PAGE along with GST.119–224 and ras-GAP binding proteins of FIG. 16A. Proteins were detected both by autoradiography (FIG. 16B) and by Coomassie blue staining (FIG. 16C). The prominent bands in FIG. 16C are rp62$^{GAPbp}$ (lane 1), antibody (lane 2), and fusion protein (lane 3). The 62 kD protein was precipitated by two different anti-ras-GAP antibodies, indicating that the association between the 62 kD protein and ras-GAP may be a specific interaction. $^{35}$S-methionine labelled p62 protein bands from FIG. 16B were excised and partially digested in the second dimensional 15% SDS-PAGE. V8 protease digestion of the 62 kD proteins precipitated by GST.119–224 and anti-GAP antibody produced identical cleavage patterns (FIG. 16D), indicating that p62 can bind to both the p56$^{lck}$ SH2 domain and ras-GAP.

A "62 kD to 68 kD" phosphotyrosyl-protein has been recognized as a pY dependent ras-GAP SH2 domain binding protein (p62$^{GAPbp}$) and its cDNA has been cloned (Wong, G. et al. (1992) *Cell* 69:551–558). However, recombinant p62$^{GAPbp}$ runs slower than p62 on SDS-PAGE, and in this gel is closer to 68 kD (FIGS. 16B and 16C). p62 was purified from a 200 liter HeLa cell culture using GST.119–224 affinity column, separated on 8% SDS-PAGE, electrotransferred to PVDF membrane, and the p62 band was cut from the blot. The p62 was digested with Lys-C. Furthermore, the amino acid sequence of an internal peptide of purified p62 (FIG. 16E) does not match p62$^{GAPbp}$ or any other known protein sequence in the data base. Thus, p62 is a novel protein and is different from the previously characterized pp62$^{GAPbp}$.

E. p62 Associates with Ser/Thr Protein Kinase Activity

Figure 17A:
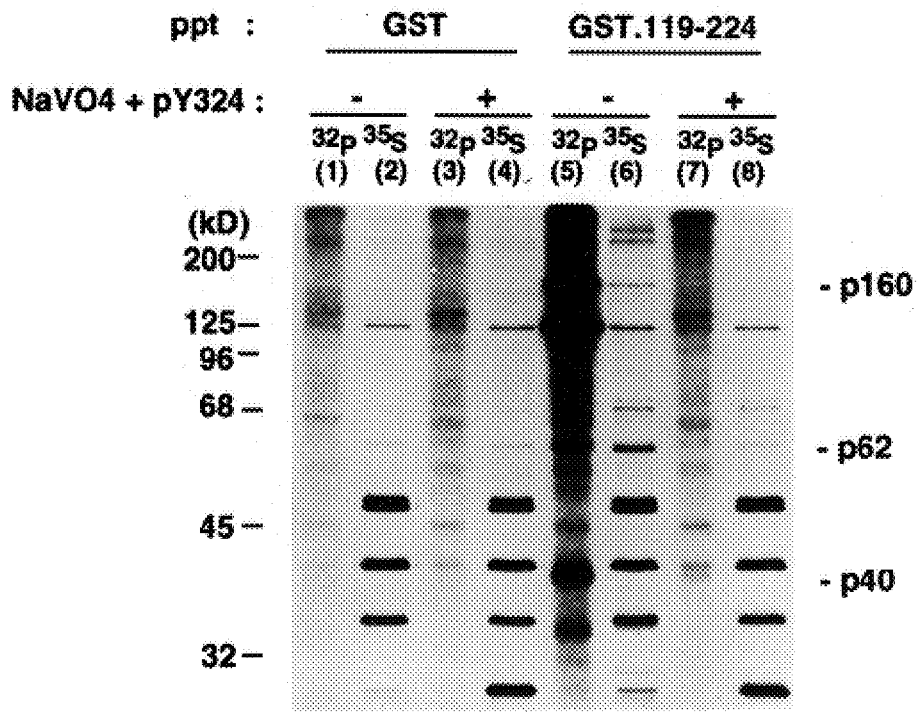
FIGS. 17A–17E depict the results of experiments demonstrating that one of the phosphotyrosine-independent proteins binding to the Lck SH2 domain is a ser/thr kinase.

Protein kinase activity as a potential role of proteins that bind to the p56$^{lck}$ SH2 domain in a pY-independent manner was examined. $^{35}$S-methionine labelled HeLa cells were lysed in the presence or absence of phosphatase inhibitors and competing peptide pY324. The lysates were incubated with GST alone or with GST.119–224. Bound proteins were separated on 9% SDS-PAGE, fluorographed, and detected by autoradiography (lanes 2, 4, 6, and 8). Kinase activity was also measured by incubating the bound proteins with kinase buffer and $^{32}$P-g-ATP (lanes 1, 3, 5, and 7). In addition to p62, three additional discrete $^{35}$S-labeled protein bands including p160, and two high molecular weight protein bands were sometimes observed in HeLa cell lysate as p56$^{lck}$ SH2 domain binding proteins (FIG. 17A, lane 6). When $^{32}$PATP and kinase reaction buffer were added, the protein complex containing the p56$^{lck}$ SH2 domain and the bound proteins induced phosphorylation of p62, p160, and a few other binding proteins including a 100 kD common GST binding protein (lane 5). This phosphorylation event was observed neither in the GST-protein complex (lanes 1 and 3) nor in the GST.SH2-protein complex formed in the presence of NaVO$_4$ and pY324 (lane 7). This kinase activity can also use myelin basic protein (MBP) as an exogenous substrate (FIG. 17B) and the kinase activity can be eluted from the protein complex by NaVO$_4$ and pY324 (FIG. 17C). Sample aliquots of FIG. 17A, lanes 2, 4, 6, and 8 were incubated with kinase buffer, $^{32}$P-g-ATP, and myelin basic protein (MBP) as exogenous substrate. MBP was separated on 12% SDS-PAGE, and its phosphorylation was visualized by autoradiography. In FIG. 17C, MBP kinase activity (lane 1) was sequentially eluted with competing pY324 peptide (lane 2) and then with glutathione (lane 3) from glutathione-agarose bound to GST.119–224 and its associated proteins (part of the sample shown in FIG. 17A lane 6 was used).

Figure 17B:
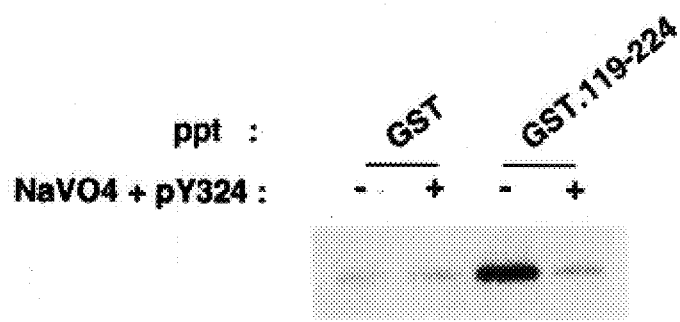
Figure 17C:
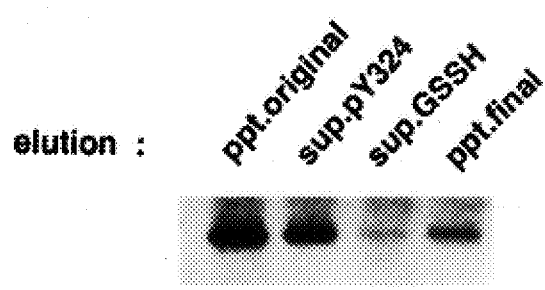
Figure 17D:
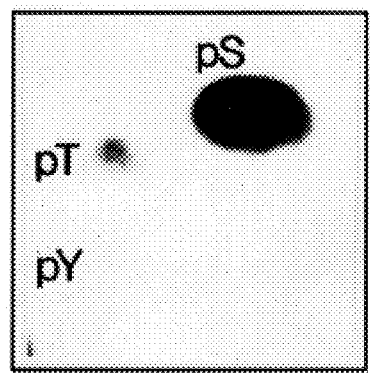

Phospho-amino acid analysis of phosphorylated MBP of FIG. 17B produced mostly phosphoserine and some phosphothreonine (FIG. 17D). The same phosphoamino acid composition was found for endogenous substrates such as p35, p62, p110, and p160 of FIG. 17A, lane 5. These results suggest that one of the pY-independent proteins binding to the p$_{56}^{lck}$ SH2 domain is a ser/thr kinase.

Figure 17E:
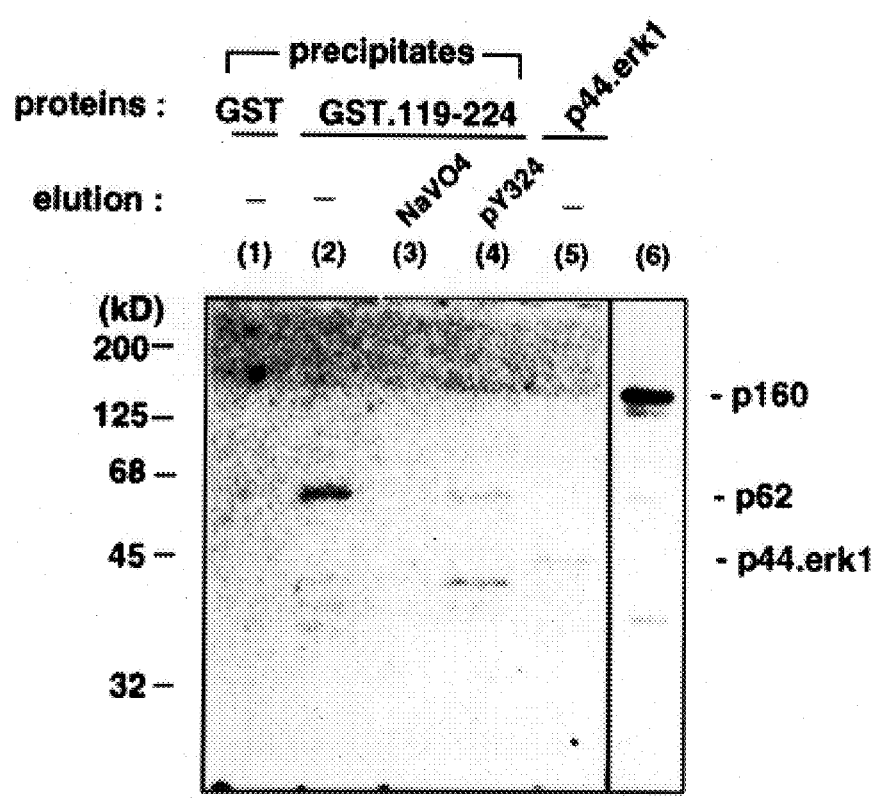

The GST.SH2-protein complex (the same as FIG. 17A, lane 5) was separated on SDS-PAGE that was polymerized in the presence of MBP. Proteins on the gel were renatured and the location of kinase activity was measured (FIG. 17E and Tobe, K. et al. (1992) *J. Biol. Chem.* 267:21089–21097). For a positive control, 0.5 mg of purified p44.erk1 (UBI) was used (lane 5). A sample of an in vitro kinase assay as described in FIG. 17A, lane 5, was separately run on a SDS-PAGE (lane 6) and compared with in-gel kinase assay. Neither GST itself nor GST-SH2 in the presence of NaVO$_4$ and pY324 brought down any MBP kinase activity. However, GST-SH2, in the absence of NaVO$_4$ and the competing peptide, associated with an MBP kinase activity with migration the same as p62. Thus p62 itself or a protein with similar molecular weight appears to be a Ser/Thr protein kinase, indicative of its potential role in a kinase cascade distinct from pathways initiated by binding of pY-proteins.

The pY-independent binding of proteins to the p56$^{lck}$ SH2 domain suggests another class of protein-protein interactions mediated by SH2 domains. However, p62 interaction with the p56$^{lck}$ SH2 domain does not appear to require serine phosphorylation, as evidenced by reduced binding in the presence of phosphatase inhibitors (FIG. 12C).

The binding of the SH2 domain, a small module composed of about 100 amino acids (Pawson, T. et al. (1993) *Current Biology* 3:434–442), to proteins in two different ways requires efficient use of the accessible surface. Competition between p62 and specific phosphotyrosyl-peptide binding to the p56$^{lck}$ SH2 domain (FIG. 13) indicates that occupation of one of these protein binding sites excludes binding to the other site. Possible mechanisms for this exclusion include (i) the use of a single binding site or two adjacent sites for these two types of protein interaction resulting in steric hindrance induced by the binding of one ligand, or (ii) the allosteric alteration of one site by the occupation of the other. Although the possibility of a single binding site has not been excluded, the observation that GST.53–224 binds tightly to phosphotyrosyl proteins but not to p62 (FIGS. 15A–15C) indicates that pY-independent binding may use a site other than the pY binding pocket. Successful binding of GST.SH2.R154K, which has a dysfunctional pY binding pocket, to p62 (FIGS. 14A–14B) suggests that these two binding modes of the SH2 domain have different binding mechanisms if not separate binding sites. In any case, competition between phosphotyrosyl peptides and p62 for the p56$^{lck}$ SH2 domain permits only one of these two binding sites to be used at any given time, thus allowing the maintenance of two separate binding sites on such a small domain.

The C-terminal pTyr505 suppresses the catalytic activity through intramolecular interaction with the SH2 domain of p56$^{lck}$ (Cooper, J. et al. (1993) *Cell* 73:1051–1054; Chan, A. et al. (1994) *Annu. Rev. Immunol.* 12:555–592). During T cell activation, the C-terminal Tyr505 is dephosphorylated, freeing the pY binding pocket of the SH2 domain, and Ser59 undergoes transient phosphorylation following the activation of MAP kinase. Since the binding of p62 to the p56$^{lck}$ SH2 domain is sensitive both to Ser59 phosphorylation (FIGS. 15A–15C) and to phosphotyrosyl peptide binding (FIG. 13), interaction of p62 and SH2 domain in full length p56$^{lck}$ would be likely to occur at the time when Tyr505 is dephosphorylated and Ser59 is phosphorylated. Since MAP kinase activation precedes Ser59 phosphorylation, the pY-independent binding of the p56$^{lck}$ SH2 domain may be involved in regulation of later stages of signal transduction.

F. p62 is Localized to the Cytoplasm and Binds to lck SH2 Domain in a Phosphotyrosine-independent Manner Immunofluorescence staining of p62 in HeLa cells showed that p62 is mostly, if not exclusively, localized to the cytoplasm. Expression of T7-epitope tagged p62 and its deletion mutants of p62 followed by GST-SH2 binding assay shows that (i) the binding is stronger in the absence of NaVO$_4$ as expected and (ii) binding site for the lck SH2 domain is located in the N-terminal 50 amino acids. A tyrosine residue (Tyr 9) present in the N-terminal 50 amino acids can be mutated to phenylalanine without any change in binding to the lck SH2 domain. Thus, p62 indeed binds the lck SH2 domain in a phosphotyrosine-independent manner.

In addition, T7-epitope specific immunoprecipitation of p62 pulled down the same MBP Ser/Thr kinase activity which has been seen in p62-lck.SH2 complex. Furthermore, transient expression of p62 augmented PMA/Ionomycin induced gene activation of NF-AT transcription factor and IL-2 20 and 5 fold, respectively, in Jurkat T cells. These results suggest that the cloned cDNA indeed encodes p62 protein and its binding mechanism to the lck.SH2 domain is unique and significant in T cell signaling.

G. p62 Can Arrest Cell Cycle Progression

When p62 was transiently expressed in p62 positive HeLa cells, the cells stopped their cell cycle progression at the G1/S boundary as shown by DNA content analysis. This result was confirmed by biochemical analysis. p62 overexpressing HeLa cells were found only in interphase while cells which were not transfected were found in all stages of cell cycle including M phase.

H. p62 Binds Directly and Noncovalently to Ubiquitin

Potential binding proteins for p62 have been sought using p62 as a bait in the GAL4-fusion based yeast two hybrid system. Forty-six truly positive clones were obtained and twenty-six of them were initially analyzed. Twenty-three of the twenty-six positive clones contained the human ubiquitin gene fused to the GAL4-activation domain. Furthermore, ubiquitin-conjugated Sepharose bead (Ub-Spharose) but not sepharose bead itself precipitated p62 from HeLa cell lysate, and this ubiquitin-p62 interaction was competed by excess soluble ubiquitin in reaction mixture. However, unlike enzymes for the ubiquitin conjugation process such as E1, E2, and E3, ubiquitin and p62 do not require ATP and DTT for association and dissociation respectively. In addition, the ubiquitin binding region of p62 has been mapped in the C-terminal 150 amino acids. These results suggest that p62 directly and noncovalently binds to ubiquitin and thus that a physiological role of p62 is coupled to the ubiquitination-mediated specific protein degradation.

I. p62 Overexpression in HeLa Cells Stabilizes the Tumor Suppressor p53

Ubiquitination followed by rapid destruction of cyclins, the mitotic inhibitor p27, and the tumor suppressor p53 have been recently recognized as major cell cycle regulation mechanisms. Particularly, in HeLa cells which were transformed by papilloma virus type 18, viral E6 protein induced rapid degradation of p53 via activation of a E6-AP ubiquitin ligase. Destabilization of p53 resulted in suppressed expression of cdk inhibitor p21$^{cip}$, thus resulting in tumorigenesis.

Overexpression of p62 in HeLa cells substantially stabilized p53 and induced increased expression level of p21$^{cip}$. However, expression levels of G1/S cyclins (D and E) were not affected by p62 overexpression. In in vitro analysis, p53 was rapidly degraded upon addition of E6 to rabbit reticulocyte lysate. Addition of p62 to this reaction prevented p53 from rapid degradation. Furthermore, p62 prevents the formation of E6 dependent ubiquitin-p53 conjugates. These results suggest that cell cycle arrest observed in p62 over-expressing HeLa cells is at least partly due to a reactivated p53-p21$^{cip}$ cell cycle surveillance system, and that p62 regulates the stability of p53 by blocking the E6-induced ubiquitination.

J. p62 (From HeLa Cells) Modification is Dependent on The Cell Cycle

When HeLa cells were arrested at M-phase by nocodazol treatment, 100% of p62H undergo apparent modification(s) as shown by its gel mobility changes either migrating as 64 kD or as 65 kD size. This modification is not an artifactual modification by the nocodazol treatment because mitotic cells that were released from hydroxylurea-induced G1/S blockage showed the same modification. Furthermore, when the mitotic cells entered G1 phase, p62 regained its mobility on the SDS-PAGE as 62 kD. Additional experiments with more defined time intervals confirmed that the p62 modification occurred only during M-phase.

A few proteins change their mobility on SDS-PAGE upon Ser/Thr phosphorylation(s) of proline-directed kinase substrate site(s). Interestingly, p62 has several such phosphorylation sites. In many cases, this type of modification serves as a critical regulatory element for the function of target protein. Thus, it is expected that p62 may also have a role in cell division process in addition to a regulatory role in interphase event, and that its function is tightly regulated.

K. p62 Gene Family Members have Distinct Roles/Mechanisms of Action

Stable overexpression of p62 in a leukemic T cell line Jurkat has been successfully established. Unlike epithelial cells and fibroblasts (exemplified in HeLa and NIH3T3 cells), Jurkat cells that overexpress p62 maintain their proliferation as compared to untransfected Jurkat cells. In two independent parallel experiments using Jurkat cells and the p56$^{lck}$ negative mutant cell line J.Cam.1.6, only Jurkat cell lines overexpressing p62 were obtained. No J.Cam.1.6 cell lines overexpressing p62 were obtained. As p62 was originally identified as a cellular ligand for the SH2 domain of p56$^{lck}$, it is possible that lack of p56lck may be critical in resistance to p62 overexpression not only in fibroblast and epithelial cells but also in T cells. This result also indicates that T cells may have a distinct mechanism(s) which can be compatible with p56$^{lck}$ for cell cycle regulation regarding p62 function. As described, the presence of hematopoietic lineage specific isoform(s) of p62 may partly account for this discrepancy.

In addition to some key proteins in cell cycle machinery, components of mitogenic transcription factors such as NFkB, lkB, c-jun, and c-fos are also regulated by ubiquitination mediated degradation initiated by external signals. Transient expression of p62 augmented PMA/Ca$^{++}$ induced activation of IL-2 gene in Jurkat T cells. As the IL-2 promoter contains binding sites for NF-kB and AP-1, it is possible that, in a T cell environment, overexpression of p62 may affect the fate of some of these transcription factors upon PMA/Ca$^{++}$ signals and lead to augmented activation of the IL-2 gene.

In conclusion, based on the results described herein, p62 can be described as a protein (i) that binds to the p56$^{lck}$ SH2 domain and thus is likely to be involved in initiation of signal mediating process upon external stimulus; (ii) that binds to ubiquitin and is involved in ubiquitin-mediated specific protein degradation at the downstream of the signal transduction; (iii) that binds to and uses a Ser/Thr kinase and the p125 ras-GAP as signal mediators; (iv) that contains regulatory features in itself for tight control of its functions; and (v) that is expressed as a tissue specific isoform in order to maintain its functional compatibility or to be used in distinct functions.

M-phase specific modification of p62 as well as its ability to bind to ubiquitin, to bind the p56$^{lck}$ SH2 domain, to bind to a Ser/Thr kinase, and to bind p120 ras-GAP strongly suggest that p62 would be the first identified protein having such a regulated ubiquitination process.

Example IV

Production of Anti-p62 Antibody

A 17-mer synthetic peptide (comprising amino acids Ser407 to Asp423 of the amino acid sequence of FIG. 2, SEQ ID NO:2 and encoded by nucleotides 1285 to 1335 of the nucleotide sequence of FIG. 1, SEQ ID NO:1) was generated. This peptide was used as an immunogen in two rabbits. Polyclonal antisera against the 17-mer peptide was then isolated.

Example V

Modification of p62 Polypeptide Domains and Effects of Modification on p62 Activity Site-directed mutagenesis was performed on uracil-containing phage DNA (Kunkel, T. (1985) *Proc. Natl. Acad. Sci USA* 82:488–492) using the M13 Muta-Gene kit (Bio-Rad). The results of the mutagenesis are shown in Table I below.

TABLE I

| Deletion Sites amino acids (nucleic acids) | SH2 Binding | Ubiquitin Binding | Inhibition of p53 Ubiquitination | Inhibition of p53 Degradation |
|---|---|---|---|---|
| Wild type (no deletion) | + | + | + | + |
| Tyr9 to Ser28 (t91 to c150) | − | nd | nd | nd |
| Pro29 to Arg50 (c151 to g216) | − | nd | nd | nd |
| Met1 to Arg50 (a67 to g216) | − | nd | nd | nd |
| Met1 to Lys187 (a67 to g627) | − | + | nd | nd |
| Asp258 to Leu440 (t840 to g1386) | + | − | nd | nd |
| Glu32 to Pro322 (g160 to t1032) | nd | + | nd | nd |
| Met1 to Lys295 (a67 to g951) | nd | + | + | + |

Equivalents

Those skilled in the art will recognize, or be able to ascertain using no more than routine experimentation, many equivalents of the specific embodiments of the invention described herein. Such equivalents are intended to be encompassed by the following claims.

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
(A) LENGTH: 2083 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 67..1390

(xi) SEQUENCE DESCRIPTION: SEQ ID NO:1:

```
GAATTCGGCA CGAGGCGCGG CGGCTGCGAC CGGGACGGCC CATTTTCCGC CAGCTCGCCG        60

CTCGCT ATG GCG TCG CTC ACC GTG AAG GCC TAC CTT CTG GGC AAG GAG          108
       Met Ala Ser Leu Thr Val Lys Ala Tyr Leu Leu Gly Lys Glu
         1               5                  10

GAC GCG GCG CGC GAG ATT CGC CGC TTC AGC TTC TGC TGC AGC CCC GAG          156
Asp Ala Ala Arg Glu Ile Arg Arg Phe Ser Phe Cys Cys Ser Pro Glu
 15                  20                  25                  30

CCT GAG GCG GAA GCC GAG GCT GCG GCG GGT CCG GGA CCC TGC GAG CGG          204
Pro Glu Ala Glu Ala Glu Ala Ala Ala Gly Pro Gly Pro Cys Glu Arg
                 35                  40                  45

CTG CTG AGC CGG GTG GCC GCC CTG TTC CCC GCG CTG CGG CCT GGC GGC          252
Leu Leu Ser Arg Val Ala Ala Leu Phe Pro Ala Leu Arg Pro Gly Gly
         50                  55                  60

TTC CAG GCG CAC TAC CGC GAT GAG GAC GGG GAC TTG GTT GCC TTT TCC          300
Phe Gln Ala His Tyr Arg Asp Glu Asp Gly Asp Leu Val Ala Phe Ser
     65                  70                  75

AGT GAC GAG GAA TTG ACA ATG GCC ATG TCC TAC GTG AAG GAT GAC ATC          348
Ser Asp Glu Glu Leu Thr Met Ala Met Ser Tyr Val Lys Asp Asp Ile
 80                  85                  90

TTC CGA ATC TAC ATT AAA GAG AAA AAA GAG TGC CGG CGG GAC CAC CGC          396
Phe Arg Ile Tyr Ile Lys Glu Lys Lys Glu Cys Arg Arg Asp His Arg
 95                 100                 105                 110

CCA CCG TGT GCT CAG GAG GCG CCC CGC AAC ATG GTG CAC CCC AAT GTG          444
```

-continued

| | |
|---|---|
| Pro Pro Cys Ala Gln Glu Ala Pro Arg Asn Met Val His Pro Asn Val<br>                115                      120                      125 | |
| ATC TGC GAT GGC TGC AAT GGG CCT GTG GTA GGA ACC CGC TAC AAG TGC<br>Ile Cys Asp Gly Cys Asn Gly Pro Val Val Gly Thr Arg Tyr Lys Cys<br>            130                      135                      140 | 492 |
| AGC GTC TGC CCA GAC TAC GAC TTG TGT AGC GTC TGC GAG GGA AAG GGC<br>Ser Val Cys Pro Asp Tyr Asp Leu Cys Ser Val Cys Glu Gly Lys Gly<br>            145                      150                      155 | 540 |
| TTG CAC CGG GGG CAC ACC AAG CTC GCA TTC CCC AGC CCC TTC GGG CAC<br>Leu His Arg Gly His Thr Lys Leu Ala Phe Pro Ser Pro Phe Gly His<br>            160                      165                      170 | 588 |
| CTG TCT GAG GGC TTC TCG CAC AGC CGC TGG CTC CGG AAG GTG AAA CAC<br>Leu Ser Glu Gly Phe Ser His Ser Arg Trp Leu Arg Lys Val Lys His<br>175                      180                      185                      190 | 636 |
| GGA CAC TTC GGG TGG CCA GGA TGG GAA ATG GGT CCA CCA GGA AAC TGG<br>Gly His Phe Gly Trp Pro Gly Trp Glu Met Gly Pro Pro Gly Asn Trp<br>                      195                      200                      205 | 684 |
| AGC CCA CGT CCT CCT CGT GCA GGG GAG GCC CGC CCT GGC CCC ACG GCA<br>Ser Pro Arg Pro Pro Arg Ala Gly Glu Ala Arg Pro Gly Pro Thr Ala<br>                  210                      215                      220 | 732 |
| GAA TCA GCT TCT GGT CCA TCG GAG GAT CCG AGT GTG AAT TTC CTG AAG<br>Glu Ser Ala Ser Gly Pro Ser Glu Asp Pro Ser Val Asn Phe Leu Lys<br>              225                      230                      235 | 780 |
| AAC GTT GGG GAG AGT GTG GCA GCT GCC CTT AGC CCT CTG GGC ATT GAA<br>Asn Val Gly Glu Ser Val Ala Ala Leu Ser Pro Leu Gly Ile Glu<br>            240                      245                      250 | 828 |
| GTT GAT ATC GAT GTG GAG CAC GGA GGG AAA AGA AGC CGC CTG ACC CCC<br>Val Asp Ile Asp Val Glu His Gly Gly Lys Arg Ser Arg Leu Thr Pro<br>255                      260                      265                      270 | 876 |
| GTC TCT CCA GAG AGT TCC AGC ACA GAG GAG AAG AGC AGC TCA CAG CCA<br>Val Ser Pro Glu Ser Ser Ser Thr Glu Glu Lys Ser Ser Ser Gln Pro<br>                  275                      280                      285 | 924 |
| AGC AGC TGC TGC TCT GAC CCC AGC AAG CCG GGT GGG AAT GTT GAG GGC<br>Ser Ser Cys Cys Ser Asp Pro Ser Lys Pro Gly Gly Asn Val Glu Gly<br>            290                      295                      300 | 972 |
| GCC ACG CAG TCT CTG GCG GAG CAG ATG AGG AAG ATC GCC TTG GAG TCC<br>Ala Thr Gln Ser Leu Ala Glu Gln Met Arg Lys Ile Ala Leu Glu Ser<br>                  305                      310                      315 | 1020 |
| GAG GGG CGC CCT GAG GAA CAG ATG GAG TCG GAT AAC TGT TCA GGA GGA<br>Glu Gly Arg Pro Glu Glu Gln Met Glu Ser Asp Asn Cys Ser Gly Gly<br>320                      325                      330 | 1068 |
| GAT GAT GAC TGG ACC CAT CTG TCT TCA AAA GAA GTG GAC CCG TCT ACA<br>Asp Asp Asp Trp Thr His Leu Ser Ser Lys Glu Val Asp Pro Ser Thr<br>335                      340                      345                      350 | 1116 |
| GGT GAA CTC CAG TCC CTA CAG ATG CCA GAA TCC GAA GGG CCA AGC TCT<br>Gly Glu Leu Gln Ser Leu Gln Met Pro Glu Ser Glu Gly Pro Ser Ser<br>                  355                      360                      365 | 1164 |
| CTG GAC CCC TCC CAG GAG GGA CCC ACA GGG CTG AAG GAA GCT GCC TTG<br>Leu Asp Pro Ser Gln Glu Gly Pro Thr Gly Leu Lys Glu Ala Ala Leu<br>                  370                      375                      380 | 1212 |
| TAC CCA CAT CTA CCG CCA GAG GCT GAC CCG CGG CTG ATT GAG TCC CTC<br>Tyr Pro His Leu Pro Pro Glu Ala Asp Pro Arg Leu Ile Glu Ser Leu<br>                  385                      390                      395 | 1260 |
| TCC CAG ATG CTG TCC ATG GGC TTC TCT GAT GAA GGC GGC TGG CTC ACC<br>Ser Gln Met Leu Ser Met Gly Phe Ser Asp Glu Gly Gly Trp Leu Thr<br>            400                      405                      410 | 1308 |
| AGG CTC CTG CAG ACC AAG AAC TAT GAC ATC GGA GCG GCT CTG GAC ACC<br>Arg Leu Leu Gln Thr Lys Asn Tyr Asp Ile Gly Ala Ala Leu Asp Thr<br>415                      420                      425                      430 | 1356 |
| ATC CAG TAT TCA AAG CAT CCC CCG CCG TTG TGA C CACTTTTGCC | 1400 |

```
Ile Gln Tyr Ser Lys His Pro Pro Pro Leu *
                435                 440

CACCTCTTCT GCNTGCCCCT CTTCTGTCTC ATAGTTGTGT TAAGCTTGCG TAGAATTGCA    1460

GGTCTCTGTA CGGGCCAGTT TCTCTGCCTT CTTCCAGGAT CAGGGGTTAG GGTGCAAGAA    1520

GCCATTTAGG GCAGCAAAAC AAGTGACATG AAGGGAGGGT CCCTGTGTGT GTGTGTGCTG    1580

ATGTTTCCTG GGTGCCCTGG CTCCTTGCAG CAGGGCTGGG CCTGCGAGAC CCAAGGCTCA    1640

CTGCAGCGCG CTCCTGACCC CTCCCTGCAG GGGCTACGTT AGCAGCCCAG CACATAGCTT    1700

GCCTAATGGC TTTCACTTTC TCTTTTGTTT TAAATGACTC ATAGGTCCCT GACATTTAGT    1760

TGATTATTTT CTGCTACAGA CCTGGTACAC TCTGATTTTA GATAAAGTAA GCCTAGGTGT    1820

TGTCAGCAGG CAGGCTGGGG AGGCCAGTGT TGTGGGCTTC CTGCTGGGAC TGAGAAGGCT    1880

CACGAAGGGC ATCCGCAATG TTGGTTTCAC TGAGAGCTGC CTCCTGGTCT CTTCACCACT    1940

GTAGTTCTCT CATTTCCAAA CCATCAGCTG CTTTTAAAAT AAGATCTCTT TGTAGCCATC    2000

CTGTTAAATT TGTAAACAAT CTAATTAAAT GGCATCAGCA CTTTAACCAA TAAAAAAAAA    2060

AAAAAAAAAA AAAACTCGAG GGA                                             2083
```

(2) INFORMATION FOR SEQ ID NO:2:

(i) SEQUENCE CHARACTERISTICS:
        (A) LENGTH: 440 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Ser Leu Thr Val Lys Ala Tyr Leu Leu Gly Lys Glu Asp Ala
  1               5                  10                  15

Ala Arg Glu Ile Arg Arg Phe Ser Phe Cys Cys Ser Pro Glu Pro Glu
             20                  25                  30

Ala Glu Ala Glu Ala Ala Gly Pro Gly Pro Cys Glu Arg Leu Leu
         35                  40                  45

Ser Arg Val Ala Ala Leu Phe Pro Ala Leu Arg Pro Gly Gly Phe Gln
         50                  55                  60

Ala His Tyr Arg Asp Glu Asp Gly Asp Leu Val Ala Phe Ser Ser Asp
 65                  70                  75                  80

Glu Glu Leu Thr Met Ala Met Ser Tyr Val Lys Asp Asp Ile Phe Arg
                 85                  90                  95

Ile Tyr Ile Lys Glu Lys Lys Glu Cys Arg Arg Asp His Arg Pro Pro
                100                 105                 110

Cys Ala Gln Glu Ala Pro Arg Asn Met Val His Pro Asn Val Ile Cys
            115                 120                 125

Asp Gly Cys Asn Gly Pro Val Val Gly Thr Arg Tyr Lys Cys Ser Val
        130                 135                 140

Cys Pro Asp Tyr Asp Leu Cys Ser Val Cys Glu Gly Lys Gly Leu His
145                 150                 155                 160

Arg Gly His Thr Lys Leu Ala Phe Pro Ser Pro Phe Gly His Leu Ser
                165                 170                 175

Glu Gly Phe Ser His Ser Arg Trp Leu Arg Lys Val Lys His Gly His
            180                 185                 190

Phe Gly Trp Pro Gly Trp Glu Met Gly Pro Gly Asn Trp Ser Pro
        195                 200                 205

Arg Pro Pro Arg Ala Gly Glu Ala Arg Pro Gly Pro Thr Ala Glu Ser
    210                 215                 220
```

```
Ala Ser Gly Pro Ser Glu Asp Pro Ser Val Asn Phe Leu Lys Asn Val
225                 230                 235                 240

Gly Glu Ser Val Ala Ala Leu Ser Pro Leu Gly Ile Glu Val Asp
            245                 250                 255

Ile Asp Val Glu His Gly Gly Lys Arg Ser Arg Leu Thr Pro Val Ser
                260                 265                 270

Pro Glu Ser Ser Thr Glu Lys Ser Ser Ser Gln Pro Ser Ser
            275                 280                 285

Cys Cys Ser Asp Pro Ser Lys Pro Gly Gly Asn Val Glu Gly Ala Thr
290                 295                 300

Gln Ser Leu Ala Glu Gln Met Arg Lys Ile Ala Leu Glu Ser Glu Gly
305                 310                 315                 320

Arg Pro Glu Glu Gln Met Glu Ser Asp Asn Cys Ser Gly Gly Asp Asp
                325                 330                 335

Asp Trp Thr His Leu Ser Ser Lys Glu Val Asp Pro Ser Thr Gly Glu
                340                 345                 350

Leu Gln Ser Leu Gln Met Pro Glu Ser Glu Gly Pro Ser Ser Leu Asp
            355                 360                 365

Pro Ser Gln Glu Gly Pro Thr Gly Leu Lys Glu Ala Ala Leu Tyr Pro
370                 375                 380

His Leu Pro Pro Glu Ala Asp Pro Arg Leu Ile Glu Ser Leu Ser Gln
385                 390                 395                 400

Met Leu Ser Met Gly Phe Ser Asp Glu Gly Gly Trp Leu Thr Arg Leu
                405                 410                 415

Leu Gln Thr Lys Asn Tyr Asp Ile Gly Ala Ala Leu Asp Thr Ile Gln
            420                 425                 430

Tyr Ser Lys His Pro Pro Leu
            435                 440

(2) INFORMATION FOR SEQ ID NO:3:

(i) SEQUENCE CHARACTERISTICS:
        (A) LENGTH: 1977 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1260

(xi) SEQUENCE DESCRIPTION: SEQ ID NO:3:

CGC CGC TTC AGC TTC TGC TTT AGC CCG GAG CCC GAG GCC GAA GCC GAG         48
Arg Arg Phe Ser Phe Cys Phe Ser Pro Glu Pro Glu Ala Glu Ala Glu
1               5                   10                  15

GCC GCG CCT GGC CCC CGG CCC TGT GAG CGG CTG CTG AAC CGG GTG GCT         96
Ala Ala Pro Gly Pro Arg Pro Cys Glu Arg Leu Leu Asn Arg Val Ala
                20                  25                  30

GCG CTC TTT CCT GTG CTC CGG CCC GGC GGC TTT CAG GCG CAC TAC CGC        144
Ala Leu Phe Pro Val Leu Arg Pro Gly Gly Phe Gln Ala His Tyr Arg
            35                  40                  45

GAT GAG GAT GGG GAC TTG GTT GCC TTT TCC AGT GAC GAG GAG CTG ACG        192
Asp Glu Asp Gly Asp Leu Val Ala Phe Ser Ser Asp Glu Glu Leu Thr
        50                  55                  60

ATG GCG ATG TCA TAT GTG AAG GAC GAC ATC TTC CGC ATT TAC ATT AAA        240
Met Ala Met Ser Tyr Val Lys Asp Asp Ile Phe Arg Ile Tyr Ile Lys
65                  70                  75                  80
```

| | | |
|---|---|---|
| GAG AAG AAG GAG TGT CGG AGG GAT CAG CGC CCC TCA TGT GCC CAG GAG | 288 | |
| Glu Lys Lys Glu Cys Arg Arg Asp Gln Arg Pro Ser Cys Ala Gln Glu | | |
| 85 90 95 | | |
| GTG CCC AGA AAC ATG GTG CAC CCC AAC GTG ATC TGT GAC GGC TGT AAC | 336 | |
| Val Pro Arg Asn Met Val His Pro Asn Val Ile Cys Asp Gly Cys Asn | | |
| 100 105 110 | | |
| GGG CCC GTG GTG GGG ACG CGC TAC AAG TGC AGC GTC TGC CCT GAC TAC | 384 | |
| Gly Pro Val Val Gly Thr Arg Tyr Lys Cys Ser Val Cys Pro Asp Tyr | | |
| 115 120 125 | | |
| GAC CTA TTC TCC GCC TGC GAG GGC AAG GGC CTG CAC CGG GAA CAC GGC | 432 | |
| Asp Leu Phe Ser Ala Cys Glu Gly Lys Gly Leu His Arg Glu His Gly | | |
| 130 135 140 | | |
| AAG CTG GCT TTC CCC AGC CCC ATT GGG CAC TTC TCT GAG GGC TTC TCT | 480 | |
| Lys Leu Ala Phe Pro Ser Pro Ile Gly His Phe Ser Glu Gly Phe Ser | | |
| 145 150 155 160 | | |
| CAC AGC CGC TGG CTC CGG AAG CTG AAA CAT GGG CAA TTT GGG TGG CCT | 528 | |
| His Ser Arg Trp Leu Arg Lys Leu Lys His Gly Gln Phe Gly Trp Pro | | |
| 165 170 175 | | |
| GCC TGG GAC ATG GGC ACA CCG GGG AAC TGG AGC CCA CGT CCT CCT CAG | 576 | |
| Ala Trp Asp Met Gly Thr Pro Gly Asn Trp Ser Pro Arg Pro Pro Gln | | |
| 180 185 190 | | |
| GCA GGG GAT GCC CAC CCT GCC CCT GCC ACG GAA TCA GCC TCT GGT CCA | 624 | |
| Ala Gly Asp Ala His Pro Ala Pro Ala Thr Glu Ser Ala Ser Gly Pro | | |
| 195 200 205 | | |
| TCG GAA CAT CCC AGT GTG AAT TTC CTC AAG AAC GTA GGG GAG AGT GTG | 672 | |
| Ser Glu His Pro Ser Val Asn Phe Leu Lys Asn Val Gly Glu Ser Val | | |
| 210 215 220 | | |
| GCG GCT GCC CTC AAG CCT CTA GGG ATT GAA GTC GAT ATT GTA GTG GAA | 720 | |
| Ala Ala Ala Leu Lys Pro Leu Gly Ile Glu Val Asp Ile Val Val Glu | | |
| 225 230 235 240 | | |
| ACG CGA GGC AAG AGA AGC CGC CTG ACC CCC ACC TCT GCA GGC AGT TCC | 768 | |
| Thr Arg Gly Lys Arg Ser Arg Leu Thr Pro Thr Ser Ala Gly Ser Ser | | |
| 245 250 255 | | |
| AGC ACA GAG GAG AAG TGT AGC TCT CAG CCA AGC AGC TGC TGC TCT GAC | 816 | |
| Ser Thr Glu Glu Lys Cys Ser Ser Gln Pro Ser Ser Cys Cys Ser Asp | | |
| 260 265 270 | | |
| CCC AGC AAG CCA GAC AGG GAC GTG GAG GGC ACA GCA CAG TCT CTG ACG | 864 | |
| Pro Ser Lys Pro Asp Arg Asp Val Glu Gly Thr Ala Gln Ser Leu Thr | | |
| 275 280 285 | | |
| GAG CAG ATG AAT AAG ATC GCC CTG GAG TCA GGG GGT CAG CAT GAG GAA | 912 | |
| Glu Gln Met Asn Lys Ile Ala Leu Glu Ser Gly Gly Gln His Glu Glu | | |
| 290 295 300 | | |
| CAG ATG GAG TCT GAT AAC TGT TCA GGA GGA GAT GAT GAC TGG ACT CAT | 960 | |
| Gln Met Glu Ser Asp Asn Cys Ser Gly Gly Asp Asp Asp Trp Thr His | | |
| 305 310 315 320 | | |
| CTG TCT TCA AAA GAG GTG GAC CCG TCT ACA GGT GAA CTG CAG TCT CTA | 1008 | |
| Leu Ser Ser Lys Glu Val Asp Pro Ser Thr Gly Glu Leu Gln Ser Leu | | |
| 325 330 335 | | |
| CAG ATG CCT GAG TCT GAA GGG CCA AGC TCT CTG GAT GGT TCC CAG GAA | 1056 | |
| Gln Met Pro Glu Ser Glu Gly Pro Ser Ser Leu Asp Gly Ser Gln Glu | | |
| 340 345 350 | | |
| GGA CCC ACA GGA CTG AAG GAA GCT GAA CTG TAC CCA CAT CTG CCA CCA | 1104 | |
| Gly Pro Thr Gly Leu Lys Glu Ala Glu Leu Tyr Pro His Leu Pro Pro | | |
| 355 360 365 | | |
| GAA GCT GAC CCC CGG CTG ATT GAG TCC CTC TCC CAG ATG CTG TCC ATG | 1152 | |
| Glu Ala Asp Pro Arg Leu Ile Glu Ser Leu Ser Gln Met Leu Ser Met | | |
| 370 375 380 | | |
| GTC TCT GAT GAA GGT GGC TGG CTC ACC AGG CTT CTG CAG ACC AAG AAT | 1200 | |
| Val Ser Asp Glu Gly Gly Trp Leu Thr Arg Leu Leu Gln Thr Lys Asn | | |
| 385 390 395 400 | | |

-continued

```
TAC GAC ATC GGG GCT GCC CTG AAC ACC ATC CAG TAT TCA AAA CAC CCA        1248
Tyr Asp Ile Gly Ala Ala Leu Asn Thr Ile Gln Tyr Ser Lys His Pro
            405                 410                 415

CCA CCT TTG TGACGATGTT TGCTCACCCA TTCTGTGTCC CCTTTGAGTT                1297
Pro Pro Leu
        420

AGTGTAGAAC CCCACTGCCT CTAAGTCCCA ATTTCTCGTC ATTCTTCTTT CAGAATCTGG     1357

GGGGTGGGGA TGCAGAAAGC CCTTTAGGGC AGTAGAACAA GTGACACGGG GGGAGTTCCA     1417

AGGGTGTGAG TGCGGATTCT GAGAAACACT GATCAGCTTC CCATGGATGC TGGCTCCTTC     1477

CAGCCAGGGG ACCCCGCCCT GGGGCAGAGC GAGAGACTCC TCGCTGGGGA GGACGTGGAG     1537

ACCATACTGC ATCTTATCCG TACTCTCCCT GCAGGATTAC ACCAGCAGTC CAGAAGAGAT     1597

CTTGCCAAAT GGCTTTCTGC TTTTTCTTTG TATAGGACAC TGATATGTAA CTGATTTTAT     1657

GCTAGAAGTT TGATATCCTC TGAATTTAGC TAAAGGATCA CCAGCATTCA CCCCGGGGTG     1717

GAAGAGGCTG TCCTGTAGCA ATTACAGCTC AGGACTGTGG CTAACATCTG AGGAATAAAG     1777

AAGGGCTGAC AGAGGAACTG ATGCTGTTCA GAGTACTGCC TATTTCATAA CCACTGTAGT     1837

TACCGTTTCC AAACCTGTCA GCTGCTTTTA AAGTTAAGAA AATCGCTTTG TAACCATTCT     1897

ATTTGTAAAC AATTTTAATT AATTAAAGGT ATAAGCACTT TAATCAAAAA AAAAAAAAA     1957

AAATTCCACC ACACTGGCGG                                                  1977
```

(2) INFORMATION FOR SEQ ID NO:4:

(i) SEQUENCE CHARACTERISTICS:
       (A) LENGTH: 419 amino acids
       (B) TYPE: amino acid
       (D) TOPOLOGY: linear (ii) MOLECULE TYPE: protein (xi) SEQUENCE DESCRIPTION: SEQ ID NO:4:

```
Arg Arg Phe Ser Phe Cys Phe Ser Pro Glu Pro Ala Glu Ala Glu
  1               5                  10                  15

Ala Ala Pro Gly Pro Arg Pro Cys Glu Arg Leu Leu Asn Arg Val Ala
             20                  25                  30

Ala Leu Phe Pro Val Leu Arg Pro Gly Gly Phe Gln Ala His Tyr Arg
         35                  40                  45

Asp Glu Asp Gly Asp Leu Val Ala Phe Ser Ser Asp Glu Glu Leu Thr
     50                  55                  60

Met Ala Met Ser Tyr Val Lys Asp Asp Ile Phe Arg Ile Tyr Ile Lys
 65                  70                  75                  80

Glu Lys Lys Glu Cys Arg Arg Asp Gln Arg Pro Ser Cys Ala Gln Glu
                 85                  90                  95

Val Pro Arg Asn Met Val His Pro Asn Val Ile Cys Asp Gly Cys Asn
            100                 105                 110

Gly Pro Val Val Gly Thr Arg Tyr Lys Cys Ser Val Cys Pro Asp Tyr
        115                 120                 125

Asp Leu Phe Ser Ala Cys Glu Gly Lys Gly Leu His Arg Glu His Gly
    130                 135                 140

Lys Leu Ala Phe Pro Ser Pro Ile Gly His Phe Ser Glu Gly Phe Ser
145                 150                 155                 160

His Ser Arg Trp Leu Arg Lys Leu Lys His Gly Gln Phe Gly Trp Pro
                165                 170                 175

Ala Trp Asp Met Gly Thr Pro Gly Asn Trp Ser Pro Arg Pro Pro Gln
            180                 185                 190
```

```
Ala Gly Asp Ala His Pro Ala Pro Ala Thr Glu Ser Ala Ser Gly Pro
            195                 200                 205

Ser Glu His Pro Ser Val Asn Phe Leu Lys Asn Val Gly Glu Ser Val
            210                 215                 220

Ala Ala Ala Leu Lys Pro Leu Gly Ile Glu Val Asp Ile Val Val Glu
225                 230                 235                 240

Thr Arg Gly Lys Arg Ser Arg Leu Thr Pro Thr Ser Ala Gly Ser Ser
                245                 250                 255

Ser Thr Glu Glu Lys Cys Ser Ser Gln Pro Ser Ser Cys Cys Ser Asp
                260                 265                 270

Pro Ser Lys Pro Asp Arg Asp Val Glu Gly Thr Ala Gln Ser Leu Thr
            275                 280                 285

Glu Gln Met Asn Lys Ile Ala Leu Glu Ser Gly Gly Gln His Glu Glu
            290                 295                 300

Gln Met Glu Ser Asp Asn Cys Ser Gly Gly Asp Asp Asp Trp Thr His
305                 310                 315                 320

Leu Ser Ser Lys Glu Val Asp Pro Ser Thr Gly Glu Leu Gln Ser Leu
                325                 330                 335

Gln Met Pro Glu Ser Glu Gly Pro Ser Ser Leu Asp Gly Ser Gln Glu
            340                 345                 350

Gly Pro Thr Gly Leu Lys Glu Ala Glu Leu Tyr Pro His Leu Pro Pro
            355                 360                 365

Glu Ala Asp Pro Arg Leu Ile Glu Ser Leu Ser Gln Met Leu Ser Met
370                 375                 380

Val Ser Asp Glu Gly Gly Trp Leu Thr Arg Leu Leu Gln Thr Lys Asn
385                 390                 395                 400

Tyr Asp Ile Gly Ala Ala Leu Asn Thr Ile Gln Tyr Ser Lys His Pro
                405                 410                 415

Pro Pro Leu (2) INFORMATION FOR SEQ ID NO:5:

(i) SEQUENCE CHARACTERISTICS:
          (A) LENGTH: 101 amino acids
          (B) TYPE: amino acid
          (D) TOPOLOGY: linear (ii) MOLECULE TYPE: peptide (v) FRAGMENT TYPE: internal (xi) SEQUENCE DESCRIPTION: SEQ ID NO:5:

Trp Phe Phe Lys Asn Leu Ser Arg Lys Asp Ala Glu Arg Gln Leu Leu
1               5                   10                  15

Ala Pro Gly Asn Thr His Gly Ser Phe Leu Ile Arg Glu Ser Glu Ser
            20                  25                  30

Thr Ala Gly Ser Phe Ser Leu Ser Val Arg Asp Phe Asp Gln Asn Gln
            35                  40                  45

Gly Glu Val Val Lys His Tyr Lys Ile Arg Asn Leu Asp Asn Gly Gly
        50                  55                  60

Phe Tyr Ile Ser Pro Arg Ile Thr Phe Pro Gly Leu His Glu Leu Val
65                  70                  75                  80

Arg His Tyr Thr Asn Ala Ser Asp Gly Leu Cys Thr Arg Leu Ser Arg
                85                  90                  95

Pro Cys Gln Thr Gln
            100
```

(2) INFORMATION FOR SEQ ID NO:6:

(i) SEQUENCE CHARACTERISTICS:
        (A) LENGTH: 3901 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 439..3847

(xi) SEQUENCE DESCRIPTION: SEQ ID NO:6:

```
GGGGCAGCCG TTCTGAGTGG GCCCTCTGCG GGCTCCGCGG CTGGGGTTCC TGGCGGGACC      60

GGGGGTCTCT CGGCAGTGAG CTCGGGCCCG CGGCTCCGCC TGCTGCTGCT GGAGAGTGTT     120

TCTGGTTTGC TGCAACCTCG AACGGGGTCT GCCGTTGCTC CGGTGCATCC CCCAAACCGC     180

TCGGCCCCAC ATTTGCCCGG GCTCATGTGC CTATTGCGGC TGCATGGGTC GGTGGGCGGG     240

GCCCAGAACC TTTCAGCTCT TGGGGCATTG GTGAGTCTCA GTAATGCACG TCTCAGTTCC     300

ATCAAAACTC GGTTTGAGGG CCTGTGTCTG CTGTCCCTGC TGGTAGGGGA GAGCCCCACA     360

GAGCTATTCC AGCAGCACTG TGTGTCTTGG CTTCGGAGCA TTCAGCAGGT GTTACAGACC     420

CAGGACCCGC CTGCCACA ATG GAG CTG GCC GTG GCT GTC CTG AGG GAC CTC      471
                    Met Glu Leu Ala Val Ala Val Leu Arg Asp Leu
                     1               5                  10

CTC CGA TAT GCA GCC CAG CTG CCT GCA CTG TTC CGG GAC ATC TCC ATG      519
Leu Arg Tyr Ala Ala Gln Leu Pro Ala Leu Phe Arg Asp Ile Ser Met
            15                  20                  25

AAC CAC CTC CCT GGC CTT CTC ACC TCC CTG CTG GGC CTC AGG CCA GAG      567
Asn His Leu Pro Gly Leu Leu Thr Ser Leu Leu Gly Leu Arg Pro Glu
        30                  35                  40

TGT GAG CAG TCA GCA TTG GAA GGA ATG AAG GCT TGT ATG ACC TAT TTC      615
Cys Glu Gln Ser Ala Leu Glu Gly Met Lys Ala Cys Met Thr Tyr Phe
    45                  50                  55

CCT CGG GCT TGT GGT TCT CTC AAA GGC AAG CTG GCC TCA TTT TTT CTG      663
Pro Arg Ala Cys Gly Ser Leu Lys Gly Lys Leu Ala Ser Phe Phe Leu
60                  65                  70                  75

TCT AGG GTG GAT GCC TTG AGC CCT CAG CTC CAA CAG TTG GCC TGT GAG      711
Ser Arg Val Asp Ala Leu Ser Pro Gln Leu Gln Gln Leu Ala Cys Glu
                80                  85                  90

TGT TAT TCC CGG CTG CCC TCT TTA GGG GCT GGC TTT TCC CAA GGC CTG      759
Cys Tyr Ser Arg Leu Pro Ser Leu Gly Ala Gly Phe Ser Gln Gly Leu
            95                 100                 105

AAG CAC ACC GAG AGC TGG GAG CAG GAG CTA CAC AGT CTG CTG GCC TCA      807
Lys His Thr Glu Ser Trp Glu Gln Glu Leu His Ser Leu Leu Ala Ser
       110                 115                 120

CTG CAC ACC CTG CTG GGG GCC CTG TAC GAG GGA GCA GAG ACT GCT CCT      855
Leu His Thr Leu Leu Gly Ala Leu Tyr Glu Gly Ala Glu Thr Ala Pro
   125                 130                 135

GTG CAG AAT GAA GGC CCT GGG GTG GAG ATG CTG CTG TCC TCA GAA GAT      903
Val Gln Asn Glu Gly Pro Gly Val Glu Met Leu Leu Ser Ser Glu Asp
140                 145                 150                 155

GGT GAT GCC CAT GTC CTT CTC CAG CTT CGG CAG AGG TTT TCG GGA CTG      951
Gly Asp Ala His Val Leu Leu Gln Leu Arg Gln Arg Phe Ser Gly Leu
                160                 165                 170

GCC CGC TGC CTA GGG CTC ATG CTC AGC TCT GAG TTT GGA GCT CCC GTG      999
Ala Arg Cys Leu Gly Leu Met Leu Ser Ser Glu Phe Gly Ala Pro Val
            175                 180                 185

TCC GTC CCT GTG CAG GAA ATC CTG GAT TTC ATC TGC CGG ACC CTC AGC     1047
Ser Val Pro Val Gln Glu Ile Leu Asp Phe Ile Cys Arg Thr Leu Ser
```

```
                190                      195                      200
GTC AGT AGC AAG AAT ATT GTA AGT GGG ATT TGT CAT CTC TTC AGA GCC        1095
Val Ser Ser Lys Asn Ile Val Ser Gly Ile Cys His Leu Phe Arg Ala
205                 210                 215

CTT GCT CAG GAT ACC AGG CAA CCA GGA AAG TAC TGG GGA CCT GAG TCT        1143
Leu Ala Gln Asp Thr Arg Gln Pro Gly Lys Tyr Trp Gly Pro Glu Ser
220                 225                 230                 235

CCC CAA ACA GTG TCA TCC TGG AGT CCG TCC CAG AGA GCT TCT ACT TTT        1191
Pro Gln Thr Val Ser Ser Trp Ser Pro Ser Gln Arg Ala Ser Thr Phe
                240                 245                 250

GTC CAA ATA ACA TCA CTT CCT ATG TGT CGT GAC ACA GGA GCA CAG TGT        1239
Val Gln Ile Thr Ser Leu Pro Met Cys Arg Asp Thr Gly Ala Gln Cys
            255                 260                 265

CAG AGT GTA GCA AAT GCT TCC TTG GGG GAG GGT GAA TTT GGG GAC TCA        1287
Gln Ser Val Ala Asn Ala Ser Leu Gly Glu Gly Glu Phe Gly Asp Ser
        270                 275                 280

GCT GAG TCA TTG CTG AGA GGC CCA GCC ATC CTT CTT ACC TTC CAT CCA        1335
Ala Glu Ser Leu Leu Arg Gly Pro Ala Ile Leu Leu Thr Phe His Pro
285                 290                 295

GGG TCT ATT TTA GAG GAT AGG GGT TTG ATT TTG TTG GGA GAG ATG AGA        1383
Gly Ser Ile Leu Glu Asp Arg Gly Leu Ile Leu Leu Gly Glu Met Arg
300                 305                 310                 315

TCA GGG GTT GGG TTT CTT ACC TAT GTG TAC ATA TGT AAA TGG TCA TTC        1431
Ser Gly Val Gly Phe Leu Thr Tyr Val Tyr Ile Cys Lys Trp Ser Phe
                320                 325                 330

CCT GTT TCT GTC TCT CTC TGG CTC TCA CTT TCT TCC TCC ACT CTT TAT        1479
Pro Val Ser Val Ser Leu Trp Leu Ser Leu Ser Ser Ser Thr Leu Tyr
                335                 340                 345

CTC TGC CCC TTT TTT CTC CAG AGC TTG CAT GGA GAT GGT CCC TGC GGC        1527
Leu Cys Pro Phe Phe Leu Gln Ser Leu His Gly Asp Gly Pro Cys Gly
            350                 355                 360

TGC TGC TGC TGC CCT CTA TCC ACC TTG AAG GCC TTG GAC CTG CTG TCT        1575
Cys Cys Cys Cys Pro Leu Ser Thr Leu Lys Ala Leu Asp Leu Leu Ser
        365                 370                 375

GCA CTC ATC CTC GCG TGT GGA AGC CGG CTC TTG CGC TTT GGG ATC CTG        1623
Ala Leu Ile Leu Ala Cys Gly Ser Arg Leu Leu Arg Phe Gly Ile Leu
380                 385                 390                 395

ATC GGC CGC CTG CTT CCC CAG GTC CTC AAT TCC TGG AGC ATC GGT AGA        1671
Ile Gly Arg Leu Leu Pro Gln Val Leu Asn Ser Trp Ser Ile Gly Arg
                400                 405                 410

GAT TCC CTC TCT CCA GGC CAG GAG AGG CCT TAC AGC ACG GTT CGG ACC        1719
Asp Ser Leu Ser Pro Gly Gln Glu Arg Pro Tyr Ser Thr Val Arg Thr
                415                 420                 425

AAG GTG TAT GCG ATA TTA GAG CTG TGG GTG CAG GTT TGT GGG GCC TCG        1767
Lys Val Tyr Ala Ile Leu Glu Leu Trp Val Gln Val Cys Gly Ala Ser
            430                 435                 440

GCG GGA ATG CTT CAG GGA GGA GCC TCT GGA GAG GCC CTG CTC ACC CAC        1815
Ala Gly Met Leu Gln Gly Gly Ala Ser Gly Glu Ala Leu Leu Thr His
        445                 450                 455

CTG CTC AGC GAC ATC TCC CCG CCA GCT GAT GCC CTT AAG CTG CGT AGC        1863
Leu Leu Ser Asp Ile Ser Pro Pro Ala Asp Ala Leu Lys Leu Arg Ser
460                 465                 470                 475

CCG CGG GGG AGC CCT GAT GGG AGT TTG CAG ACT GGG AAG CCT AGC GCC        1911
Pro Arg Gly Ser Pro Asp Gly Ser Leu Gln Thr Gly Lys Pro Ser Ala
                480                 485                 490

CCC AAG AAG CTA AAG CTG GAT GTG GGG GAA GCT ATG GCC CCG CCA AGC        1959
Pro Lys Lys Leu Lys Leu Asp Val Gly Glu Ala Met Ala Pro Pro Ser
                495                 500                 505

CAC CGG AAA GGG GAT AGC AAT GCC AAC AGC GAC GTG TGT CCG GCT GCA        2007
His Arg Lys Gly Asp Ser Asn Ala Asn Ser Asp Val Cys Pro Ala Ala
```

-continued

```
              510                     515                     520
CTC AGA GGC CTC AGC CGG ACC ATC CTC ATG TGT GGG CCT CTC ATC AAG      2055
Leu Arg Gly Leu Ser Arg Thr Ile Leu Met Cys Gly Pro Leu Ile Lys
525                     530                     535

GAG GAG ACT CAC AGG AGA CTG CAT GAC CTG GTC CTC CCC CTG GTC ATG      2103
Glu Glu Thr His Arg Arg Leu His Asp Leu Val Leu Pro Leu Val Met
540                     545                     550                     555

GGT GTA CAG CAG GGT GAG GTC CTA GGC AGC TCC CCG TAC ACG AGC TCC      2151
Gly Val Gln Gln Gly Glu Val Leu Gly Ser Ser Pro Tyr Thr Ser Ser
                        560                     565                     570

CCT GCC GCC GTG AAC TCT ACT GCC TGC TGC TGG CGC TGC TGC TGG CCC      2199
Pro Ala Ala Val Asn Ser Thr Ala Cys Cys Trp Arg Cys Cys Trp Pro
                575                     580                     585

CGT CTC CTC GCT GCC CAC CTC CTC TTG CCT GTG CCC TGC AAG CCT TCT      2247
Arg Leu Leu Ala Ala His Leu Leu Leu Pro Val Pro Cys Lys Pro Ser
                590                     595                     600

CCC TCG GCC AGC GAG AAG ATA GCC TTG AGG TCT CCT CTT TCT TGC TCA      2295
Pro Ser Ala Ser Glu Lys Ile Ala Leu Arg Ser Pro Leu Ser Cys Ser
605                     610                     615

GAA GCA CTG GTG ACC TGT GCT GCT CTG ACC CAC CCC CGG GTT CCT CCC      2343
Glu Ala Leu Val Thr Cys Ala Ala Leu Thr His Pro Arg Val Pro Pro
620                     625                     630                     635

CTG CAG CCC ATG GGC CCC ACC TGC CCC ACA CCT GCT CCA GTC CCC CTC      2391
Leu Gln Pro Met Gly Pro Thr Cys Pro Thr Pro Ala Pro Val Pro Leu
                        640                     645                     650

CTG AGG CCC CAT CGC CCT TCA GGG CCC CAC CGT TCC ATC CTC CGG GCC      2439
Leu Arg Pro His Arg Pro Ser Gly Pro His Arg Ser Ile Leu Arg Ala
                655                     660                     665

CCA TGC CCT CAG TGG GCT CCA TGC CCT CAG CAG GCC CCA TGC CCT TCA      2487
Pro Cys Pro Gln Trp Ala Pro Cys Pro Gln Gln Ala Pro Cys Pro Ser
                670                     675                     680

GCA GGC CCC ATG CCC TCA GCA GGC CCT GTG CCC TCG GAG CCC TGG ACC      2535
Ala Gly Pro Met Pro Ser Ala Gly Pro Val Pro Ser Glu Pro Trp Thr
                685                     690                     695

TCC ACC ACA GCC AAC CTC CTA GGC CTT CTG TCC AGG CCT AGT GTC TGT      2583
Ser Thr Thr Ala Asn Leu Leu Gly Leu Leu Ser Arg Pro Ser Val Cys
700                     705                     710                     715

CCT CCC CGG CTT CTT CCT GGC CCT GAG AAC CAC CGG GCA GGC TCA AAT      2631
Pro Pro Arg Leu Leu Pro Gly Pro Glu Asn His Arg Ala Gly Ser Asn
                720                     725                     730

GAG GAC CCC ATC CTT GCC CCT AGT GGG ACT CCC CCA CCT ACT ATA CCC      2679
Glu Asp Pro Ile Leu Ala Pro Ser Gly Thr Pro Pro Pro Thr Ile Pro
                735                     740                     745

CCA GAT GAA ACT TTT GGG GGG AGA GTG CCC AGA CCA GCC TTT GTC CAC      2727
Pro Asp Glu Thr Phe Gly Gly Arg Val Pro Arg Pro Ala Phe Val His
                750                     755                     760

TAT GAC AAG GAG GAG GCA TCT GAT GTG GAG ATC TCC TTG GAA AGT GAC      2775
Tyr Asp Lys Glu Glu Ala Ser Asp Val Glu Ile Ser Leu Glu Ser Asp
765                     770                     775

TCT GAT GAC AGC GTG GTG ATC GTG CCC GAG GGG CTT CCC CCC CTG CCA      2823
Ser Asp Asp Ser Val Val Ile Val Pro Glu Gly Leu Pro Pro Leu Pro
780                     785                     790                     795

CCC CCA CCA CCC TCA GGT GCC ACA CCA CCC CCT ATA GCC CCC ACT GGG      2871
Pro Pro Pro Pro Ser Gly Ala Thr Pro Pro Pro Ile Ala Pro Thr Gly
                        800                     805                     810

CCA CCA ACA GCC TCC CCT CCT GTG CCA GCG AAG GAG GAG CCT GAA GAA      2919
Pro Pro Thr Ala Ser Pro Pro Val Pro Ala Lys Glu Glu Pro Glu Glu
                815                     820                     825

CTT CCT GCG GCC CCA GGG CCT CTC CCG CCG CCC CCA CCT CCG CCG CCG      2967
Leu Pro Ala Ala Pro Gly Pro Leu Pro Pro Pro Pro Pro Pro Pro Pro
```

-continued

```
                830                835                840
CCT GTT CCT GGT CCT GTG ACN CTC CCT CCA CCC CAG TTG GTC CCT GAA    3015
Pro Val Pro Gly Pro Val Xaa Leu Pro Pro Pro Gln Leu Val Pro Glu
845                 850                 855

GGG ACT CCT GGT GGG GGA GGA CCC CCA GCC CTG GAA GAG GAT TTG ACA    3063
Gly Thr Pro Gly Gly Gly Gly Pro Pro Ala Leu Glu Glu Asp Leu Thr
860                 865                 870                 875

GTT ATT AAT ATC AAC AGC AGT GAT GAA GAG GAG GAG GAA GAA GGA GAA    3111
Val Ile Asn Ile Asn Ser Ser Asp Glu Glu Glu Glu Glu Glu Gly Glu
                880                 885                 890

GAG GAA GAA GAA GAA GAA GAA GAA GAA GAG GAA GAA GAA GAA GAG GAA    3159
Glu Glu Glu Glu Glu Glu Glu Glu Glu Glu Glu Glu Glu Glu Glu Glu
            895                 900                 905

GAA GAG GAA GAG GAG GAA GAC TTT GAG GAA GAG GAA GAG GAT GAA GAG    3207
Glu Glu Glu Glu Glu Glu Asp Phe Glu Glu Glu Glu Glu Asp Glu Glu
        910                 915                 920

GAA TAT TTT GAA GAG GAA GAA GAG GAG GAA GAA GAG TTT GAG GAA GAA    3255
Glu Tyr Phe Glu Glu Glu Glu Glu Glu Glu Glu Glu Phe Glu Glu Glu
925                 930                 935

TTT GAG GAA GAA GAA GGT GAG TTA GAG GAA GAA GAA GAA GAG GAG GAT    3303
Phe Glu Glu Glu Glu Gly Glu Leu Glu Glu Glu Glu Glu Glu Glu Asp
940                 945                 950                 955

GAG GAG GAG GAA GAA GAA CTG GAA GAG GTG GAA GAC CTG GAG TTT GGC    3351
Glu Glu Glu Glu Glu Glu Leu Glu Glu Val Glu Asp Leu Glu Phe Gly
                960                 965                 970

ACA GCA GGA GGG GAG GTA GAA GAA GGT GCA CCA CCA CCC CCA ACC CTG    3399
Thr Ala Gly Gly Glu Val Glu Glu Gly Ala Pro Pro Pro Pro Thr Leu
            975                 980                 985

CCT CCA GCT CTG CCT CCC CCT GAG TCT CCC CCA AAG GTG CAG CCA GAA    3447
Pro Pro Ala Leu Pro Pro Pro Glu Ser Pro Pro Lys Val Gln Pro Glu
        990                 995                 1000

CCC GAA CCC GAA CCC GGG CTG CTT TTG GAA GTG GAG GAG CCA GGG ACG    3495
Pro Glu Pro Glu Pro Gly Leu Leu Leu Glu Val Glu Glu Pro Gly Thr
    1005                1010                1015

GAG GAG GAG CGT GGG GCT GAC ACA GCT CCC ACC CTG GCC CCT GAA GCG    3543
Glu Glu Glu Arg Gly Ala Asp Thr Ala Pro Thr Leu Ala Pro Glu Ala
1020                1025                1030                1035

CTC CCC TCC CAG GGA GAG GTG GAG AGG GAA GGG GAA AGC CCT GCG GCA    3591
Leu Pro Ser Gln Gly Glu Val Glu Arg Glu Gly Glu Ser Pro Ala Ala
                1040                1045                1050

GGG CCC CCT CCC CAG GAG CTT GTT GAA GAA GAG CCC TCT NCT CCC CCA    3639
Gly Pro Pro Pro Gln Glu Leu Val Glu Glu Glu Pro Ser Xaa Pro Pro
            1055                1060                1065

ACC CTG TTG GAA GAG GAG ACT GAG GAT GGG AGT GAC AAG GTG CAG CCC    3687
Thr Leu Leu Glu Glu Glu Thr Glu Asp Gly Ser Asp Lys Val Gln Pro
        1070                1075                1080

CCA CCA GAG ACA CCT GCA GAA GAA GAG ATG GAG ACA GAG ACA GAG GCC    3735
Pro Pro Glu Thr Pro Ala Glu Glu Glu Met Glu Thr Glu Thr Glu Ala
    1085                1090                1095

GAA GCT CTC CAG GAA AAG GAG CAG GAT GAC ACA GCT GCC ATG CTG GCC    3783
Glu Ala Leu Gln Glu Lys Glu Gln Asp Asp Thr Ala Ala Met Leu Ala
1100                1105                1110                1115

GAC TTC ATC GAT TGT CCC CCT GAT GAT GAG AAG CCA CCA CCT CCC ACA    3831
Asp Phe Ile Asp Cys Pro Pro Asp Asp Glu Lys Pro Pro Pro Pro Thr
                1120                1125                1130

GAG CCT GAC TCC TAG C CATCTTCTGC ACCCCACCTC TTTGTTTCCA ATAAAGTTAT  3887
Glu Pro Asp Ser *
                1135

GTCCTTAAAA AAAA                                                    3901
```

(2) INFORMATION FOR SEQ ID NO:7:

(i) SEQUENCE CHARACTERISTICS:
        (A) LENGTH: 1135 amino acids
        (B) TYPE: amino acid
        (D) TOPOLOGY: linear (ii) MOLECULE TYPE: protein (xi) SEQUENCE DESCRIPTION: SEQ ID NO:7:

```
Met Glu Leu Ala Val Ala Val Leu Arg Asp Leu Leu Arg Tyr Ala Ala
 1               5                  10                  15

Gln Leu Pro Ala Leu Phe Arg Asp Ile Ser Met Asn His Leu Pro Gly
            20                  25                  30

Leu Leu Thr Ser Leu Leu Gly Leu Arg Pro Glu Cys Glu Gln Ser Ala
        35                  40                  45

Leu Glu Gly Met Lys Ala Cys Met Thr Tyr Phe Pro Arg Ala Cys Gly
    50                  55                  60

Ser Leu Lys Gly Lys Leu Ala Ser Phe Phe Leu Ser Arg Val Asp Ala
65                  70                  75                  80

Leu Ser Pro Gln Leu Gln Gln Leu Ala Cys Glu Cys Tyr Ser Arg Leu
                85                  90                  95

Pro Ser Leu Gly Ala Gly Phe Ser Gln Gly Leu Lys His Thr Glu Ser
            100                 105                 110

Trp Glu Gln Glu Leu His Ser Leu Leu Ala Ser Leu His Thr Leu Leu
        115                 120                 125

Gly Ala Leu Tyr Glu Gly Ala Glu Thr Ala Pro Val Gln Asn Glu Gly
    130                 135                 140

Pro Gly Val Glu Met Leu Leu Ser Ser Glu Asp Gly Asp Ala His Val
145                 150                 155                 160

Leu Leu Gln Leu Arg Gln Arg Phe Ser Gly Leu Ala Arg Cys Leu Gly
                165                 170                 175

Leu Met Leu Ser Ser Glu Phe Gly Ala Pro Val Ser Val Pro Val Gln
            180                 185                 190

Glu Ile Leu Asp Phe Ile Cys Arg Thr Leu Ser Val Ser Ser Lys Asn
        195                 200                 205

Ile Val Ser Gly Ile Cys His Leu Phe Arg Ala Leu Ala Gln Asp Thr
    210                 215                 220

Arg Gln Pro Gly Lys Tyr Trp Gly Pro Glu Ser Pro Gln Thr Val Ser
225                 230                 235                 240

Ser Trp Ser Pro Ser Gln Arg Ala Ser Thr Phe Val Gln Ile Thr Ser
                245                 250                 255

Leu Pro Met Cys Arg Asp Thr Gly Ala Gln Cys Gln Ser Val Ala Asn
            260                 265                 270

Ala Ser Leu Gly Glu Gly Glu Phe Gly Asp Ser Ala Glu Ser Leu Leu
        275                 280                 285

Arg Gly Pro Ala Ile Leu Leu Thr Phe His Pro Gly Ser Ile Leu Glu
    290                 295                 300

Asp Arg Gly Leu Ile Leu Leu Gly Glu Met Arg Ser Gly Val Gly Phe
305                 310                 315                 320

Leu Thr Tyr Val Tyr Ile Cys Lys Trp Ser Phe Pro Val Ser Val Ser
                325                 330                 335

Leu Trp Leu Ser Leu Ser Ser Thr Leu Tyr Leu Cys Pro Phe Phe
            340                 345                 350

Leu Gln Ser Leu His Gly Asp Gly Pro Cys Gly Cys Cys Cys Pro
        355                 360                 365
```

```
Leu Ser Thr Leu Lys Ala Leu Asp Leu Leu Ser Ala Leu Ile Leu Ala
    370                 375                 380

Cys Gly Ser Arg Leu Leu Arg Phe Gly Ile Leu Ile Gly Arg Leu Leu
385                 390                 395                 400

Pro Gln Val Leu Asn Ser Trp Ser Ile Gly Arg Asp Ser Leu Ser Pro
                405                 410                 415

Gly Gln Glu Arg Pro Tyr Ser Thr Val Arg Thr Lys Val Tyr Ala Ile
            420                 425                 430

Leu Glu Leu Trp Val Gln Val Cys Gly Ala Ser Ala Gly Met Leu Gln
        435                 440                 445

Gly Gly Ala Ser Gly Glu Ala Leu Leu Thr His Leu Leu Ser Asp Ile
    450                 455                 460

Ser Pro Pro Ala Asp Ala Leu Lys Leu Arg Ser Pro Arg Gly Ser Pro
465                 470                 475                 480

Asp Gly Ser Leu Gln Thr Gly Lys Pro Ser Ala Pro Lys Lys Leu Lys
                485                 490                 495

Leu Asp Val Gly Glu Ala Met Ala Pro Pro Ser His Arg Lys Gly Asp
            500                 505                 510

Ser Asn Ala Asn Ser Asp Val Cys Pro Ala Ala Leu Arg Gly Leu Ser
        515                 520                 525

Arg Thr Ile Leu Met Cys Gly Pro Leu Ile Lys Glu Glu Thr His Arg
    530                 535                 540

Arg Leu His Asp Leu Val Leu Pro Leu Val Met Gly Val Gln Gln Gly
545                 550                 555                 560

Glu Val Leu Gly Ser Ser Pro Tyr Thr Ser Ser Pro Ala Ala Val Asn
                565                 570                 575

Ser Thr Ala Cys Cys Trp Arg Cys Cys Trp Pro Arg Leu Leu Ala Ala
            580                 585                 590

His Leu Leu Leu Pro Val Pro Cys Lys Pro Ser Pro Ser Ala Ser Glu
        595                 600                 605

Lys Ile Ala Leu Arg Ser Pro Leu Ser Cys Ser Glu Ala Leu Val Thr
    610                 615                 620

Cys Ala Ala Leu Thr His Pro Arg Val Pro Pro Leu Gln Pro Met Gly
625                 630                 635                 640

Pro Thr Cys Pro Thr Pro Ala Pro Val Pro Leu Leu Arg Pro His Arg
                645                 650                 655

Pro Ser Gly Pro His Arg Ser Ile Leu Arg Ala Pro Cys Pro Gln Trp
            660                 665                 670

Ala Pro Cys Pro Gln Gln Ala Pro Cys Pro Ser Ala Gly Pro Met Pro
        675                 680                 685

Ser Ala Gly Pro Val Pro Ser Glu Pro Trp Thr Ser Thr Thr Ala Asn
    690                 695                 700

Leu Leu Gly Leu Leu Ser Arg Pro Ser Val Cys Pro Pro Arg Leu Leu
705                 710                 715                 720

Pro Gly Pro Glu Asn His Arg Ala Gly Ser Asn Glu Asp Pro Ile Leu
                725                 730                 735

Ala Pro Ser Gly Thr Pro Pro Thr Ile Pro Pro Asp Glu Thr Phe
            740                 745                 750

Gly Gly Arg Val Pro Arg Pro Ala Phe Val His Tyr Asp Lys Glu Glu
        755                 760                 765

Ala Ser Asp Val Glu Ile Ser Leu Glu Ser Asp Ser Asp Asp Ser Val
    770                 775                 780

Val Ile Val Pro Glu Gly Leu Pro Pro Leu Pro Pro Pro Pro Pro Ser
```

```
                                  785                 790                 795                 800
Gly Ala Thr Pro Pro Ile Ala Pro Thr Gly Pro Thr Ala Ser
                805                 810                 815

Pro Pro Val Pro Ala Lys Glu Glu Pro Glu Glu Leu Pro Ala Ala Pro
                820                 825                 830

Gly Pro Leu Pro Pro Pro Pro Pro Pro Pro Val Pro Gly Pro
            835                 840                 845

Val Xaa Leu Pro Pro Pro Gln Leu Val Pro Glu Gly Thr Pro Gly Gly
            850                 855                 860

Gly Gly Pro Pro Ala Leu Glu Glu Asp Leu Thr Val Ile Asn Ile Asn
865                 870                 875                 880

Ser Ser Asp Glu Glu Glu Glu Glu Gly Glu Glu Glu Glu Glu
                885                 890                 895

Glu Glu Glu Glu Glu Glu Glu Glu Glu Glu Glu Glu Glu Glu
            900                 905                 910

Glu Asp Phe Glu Glu Glu Glu Asp Glu Glu Glu Tyr Phe Glu Glu
            915                 920                 925

Glu Glu Glu Glu Glu Glu Glu Phe Glu Glu Glu Phe Glu Glu Glu Glu
            930                 935                 940

Gly Glu Leu Glu Glu Glu Glu Glu Glu Asp Glu Glu Glu Glu
945                 950                 955                 960

Glu Leu Glu Glu Val Glu Asp Leu Glu Phe Gly Thr Ala Gly Gly Glu
                965                 970                 975

Val Glu Glu Gly Ala Pro Pro Pro Thr Leu Pro Pro Ala Leu Pro
            980                 985                 990

Pro Pro Glu Ser Pro Pro Lys Val Gln Pro Glu Pro Glu Pro
        995                 1000                1005

Gly Leu Leu Leu Glu Val Glu Glu Pro Gly Thr Glu Glu Arg Gly
        1010                1015                1020

Ala Asp Thr Ala Pro Thr Leu Ala Pro Glu Ala Leu Pro Ser Gln Gly
1025                1030                1035                1040

Glu Val Glu Arg Glu Gly Glu Ser Pro Ala Ala Gly Pro Pro Gln
                1045                1050                1055

Glu Leu Val Glu Glu Glu Pro Ser Xaa Pro Pro Thr Leu Leu Glu Glu
                1060                1065                1070

Glu Thr Glu Asp Gly Ser Asp Lys Val Gln Pro Pro Glu Thr Pro
        1075                1080                1085

Ala Glu Glu Met Glu Thr Glu Thr Glu Ala Glu Ala Leu Gln Glu
            1090                1095                1100

Lys Glu Gln Asp Asp Thr Ala Ala Met Leu Ala Asp Phe Ile Asp Cys
1105                1110                1115                1120

Pro Pro Asp Asp Glu Lys Pro Pro Pro Thr Glu Pro Asp Ser
                1125                1130                1135

(2) INFORMATION FOR SEQ ID NO:8:

(i) SEQUENCE CHARACTERISTICS:
        (A) LENGTH: 3211 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 439..3157
```

(xi) SEQUENCE DESCRIPTION: SEQ ID NO:8:

```
GGGGCAGCCG TTCTGAGTGG GCCCTCTGCG GGCTCCGCGG CTGGGGTTCC TGGCGGGACC      60

GGGGGTCTCT CGGCAGTGAG CTCGGGCCCG CGGCTCCGCC TGCTGCTGCT GGAGAGTGTT     120

TCTGGTTTGC TGCAACCTCG AACGGGGTCT GCCGTTGCTC CGGTGCATCC CCCAAACCGC     180

TCGGCCCCAC ATTTGCCCGG GCTCATGTGC CTATTGCGGC TGCATGGGTC GGTGGGCGGG     240

GCCCAGAACC TTTCAGCTCT TGGGGCATTG GTGAGTCTCA GTAATGCACG TCTCAGTTCC     300

ATCAAAACTC GGTTTGAGGG CCTGTGTCTG CTGTCCCTGC TGGTAGGGGA GAGCCCCACA     360

GAGCTATTCC AGCAGCACTG TGTGTCTTGG CTTCGGAGCA TTCAGCAGGT GTTACAGACC     420

CAGGACCCGC CTGCCACA ATG GAG CTG GCC GTG GCT GTC CTG AGG GAC CTC       471
                   Met Glu Leu Ala Val Ala Val Leu Arg Asp Leu
                    1               5                  10

CTC CGA TAT GCA GCC CAG CTG CCT GCA CTG TTC CGG GAC ATC TCC ATG       519
Leu Arg Tyr Ala Ala Gln Leu Pro Ala Leu Phe Arg Asp Ile Ser Met
             15                  20                  25

AAC CAC CTC CCT GGC CTT CTC ACC TCC CTG CTG GGC CTC AGG CCA GAG       567
Asn His Leu Pro Gly Leu Leu Thr Ser Leu Leu Gly Leu Arg Pro Glu
             30                  35                  40

TGT GAG CAG TCA GCA TTG GAA GGA ATG AAG GCT TGT ATG ACC TAT TTC       615
Cys Glu Gln Ser Ala Leu Glu Gly Met Lys Ala Cys Met Thr Tyr Phe
 45                  50                  55

CCT CGG GCT TGT GGT TCT CTC AAA GGC AAG CTG GCC TCA TTT TTT CTG       663
Pro Arg Ala Cys Gly Ser Leu Lys Gly Lys Leu Ala Ser Phe Phe Leu
 60                  65                  70                  75

TCT AGG GTG GAT GCC TTG AGC CCT CAG CTC CAA CAG TTG GCC TGT GAG       711
Ser Arg Val Asp Ala Leu Ser Pro Gln Leu Gln Gln Leu Ala Cys Glu
             80                  85                  90

TGT TAT TCC CGG CTG CCC TCT TTA GGG GCT GGC TTT TCC CAA GGC CTG       759
Cys Tyr Ser Arg Leu Pro Ser Leu Gly Ala Gly Phe Ser Gln Gly Leu
             95                 100                 105

AAG CAC ACC GAG AGC TGG GAG CAG GAG CTA CAC AGT CTG CTG GCC TCA       807
Lys His Thr Glu Ser Trp Glu Gln Glu Leu His Ser Leu Leu Ala Ser
             110                 115                 120

CTG CAC ACC CTG CTG GGG GCC CTG TAC GAG GGA GCA GAG ACT GCT CCT       855
Leu His Thr Leu Leu Gly Ala Leu Tyr Glu Gly Ala Glu Thr Ala Pro
 125                 130                 135

GTG CAG AAT GAA GGC CCT GGG GTG GAG ATG CTG CTG TCC TCA GAA GAT       903
Val Gln Asn Glu Gly Pro Gly Val Glu Met Leu Leu Ser Ser Glu Asp
140                 145                 150                 155

GGT GAT GCC CAT GTC CTT CTC CAG CTT CGG CAG AGG TTT TCG GGA CTG       951
Gly Asp Ala His Val Leu Leu Gln Leu Arg Gln Arg Phe Ser Gly Leu
             160                 165                 170

GCC CGC TGC CTA GGG CTC ATG CTC AGC TCT GAG TTT GGA GCT CCC GTG       999
Ala Arg Cys Leu Gly Leu Met Leu Ser Ser Glu Phe Gly Ala Pro Val
             175                 180                 185

TCC GTC CCT GTG CAG GAA ATC CTG GAT TTC ATC TGC CGG ACC CTC AGC      1047
Ser Val Pro Val Gln Glu Ile Leu Asp Phe Ile Cys Arg Thr Leu Ser
             190                 195                 200

GTC AGT AGC AAG AAT ATT AGC TTG CAT GGA GAT GGT CCC TGC GGC TGC      1095
Val Ser Ser Lys Asn Ile Ser Leu His Gly Asp Gly Pro Cys Gly Cys
 205                 210                 215

TGC TGC TGC CCT CTA TCC ACC TTG AAG GCC TTG GAC CTG CTG TCT GCA      1143
Cys Cys Cys Pro Leu Ser Thr Leu Lys Ala Leu Asp Leu Leu Ser Ala
220                 225                 230                 235

CTC ATC CTC GCG TGT GGA AGC CGG CTC TTG CGC TTT GGG ATC CTG ATC      1191
Leu Ile Leu Ala Cys Gly Ser Arg Leu Leu Arg Phe Gly Ile Leu Ile
             240                 245                 250
```

```
GGC CGC CTG CTT CCC CAG GTC CTC AAT TCC TGG AGC ATC GGT AGA GAT    1239
Gly Arg Leu Leu Pro Gln Val Leu Asn Ser Trp Ser Ile Gly Arg Asp
            255                 260                 265

TCC CTC TCT CCA GGC CAG GAG AGG CCT TAC AGC ACG GTT CGG ACC AAG    1287
Ser Leu Ser Pro Gly Gln Glu Arg Pro Tyr Ser Thr Val Arg Thr Lys
        270                 275                 280

GTG TAT GCG ATA TTA GAG CTG TGG GTG CAG GTT TGT GGG GCC TCG GCG    1335
Val Tyr Ala Ile Leu Glu Leu Trp Val Gln Val Cys Gly Ala Ser Ala
    285                 290                 295

GGA ATG CTT CAG GGA GGA GCC TCT GGA GAG GCC CTG CTC ACC CAC CTG    1383
Gly Met Leu Gln Gly Gly Ala Ser Gly Glu Ala Leu Leu Thr His Leu
300                 305                 310                 315

CTC AGC GAC ATC TCC CCG CCA GCT GAT GCC CTT AAG CTG CGT AGC CCG    1431
Leu Ser Asp Ile Ser Pro Pro Ala Asp Ala Leu Lys Leu Arg Ser Pro
            320                 325                 330

CGG GGG AGC CCT GAT GGG AGT TTG CAG ACT GGG AAG CCT AGC GCC CCC    1479
Arg Gly Ser Pro Asp Gly Ser Leu Gln Thr Gly Lys Pro Ser Ala Pro
        335                 340                 345

AAG AAG CTA AAG CTG GAT GTG GGG GAA GCT ATG GCC CCG CCA AGC CAC    1527
Lys Lys Leu Lys Leu Asp Val Gly Glu Ala Met Ala Pro Pro Ser His
    350                 355                 360

CTC CTC TTG CCT GTG CCC TGC AAG CCT TCT CCC TCG GCC AGC GAG AAG    1575
Leu Leu Leu Pro Val Pro Cys Lys Pro Ser Pro Ser Ala Ser Glu Lys
365                 370                 375

ATA GCC TTG AGG TCT CCT CTT TCT TGC TCA GAA GCA CTG GTG ACC TGT    1623
Ile Ala Leu Arg Ser Pro Leu Ser Cys Ser Glu Ala Leu Val Thr Cys
380                 385                 390                 395

GCT GCT CTG ACC CAC CCC CGG GTT CCT CCC CTG CAG CCC ATG GGC CCC    1671
Ala Ala Leu Thr His Pro Arg Val Pro Pro Leu Gln Pro Met Gly Pro
            400                 405                 410

ACC TGC CCC ACA CCT GCT CCA GTC CCC CTC CTG AGG CCC CAT CGC CCT    1719
Thr Cys Pro Thr Pro Ala Pro Val Pro Leu Leu Arg Pro His Arg Pro
        415                 420                 425

TCA GGG CCC CAC CGT TCC ATC CTC CGG GCC CCA TGC CCT CAG TGG GCT    1767
Ser Gly Pro His Arg Ser Ile Leu Arg Ala Pro Cys Pro Gln Trp Ala
    430                 435                 440

CCA TGC CCT CAG CAG GCC CCA TGC CCT TCA GCA GGC CCC ATG CCC TCA    1815
Pro Cys Pro Gln Gln Ala Pro Cys Pro Ser Ala Gly Pro Met Pro Ser
445                 450                 455

GCA GGC CCT GTG CCC TCG GAG CCC TGG ACC TCC ACC ACA GCC AAC CTC    1863
Ala Gly Pro Val Pro Ser Glu Pro Trp Thr Ser Thr Thr Ala Asn Leu
460                 465                 470                 475

CTA GGC CTT CTG TCC AGG CCT AGT GTC TGT CCT CCC CGG CTT CTT CCT    1911
Leu Gly Leu Leu Ser Arg Pro Ser Val Cys Pro Pro Arg Leu Leu Pro
            480                 485                 490

GGC CCT GAG AAC CAC CGG GCA GGC TCA AAT GAG GAC CCC ATC CTT GCC    1959
Gly Pro Glu Asn His Arg Ala Gly Ser Asn Glu Asp Pro Ile Leu Ala
        495                 500                 505

CCT AGT GGG ACT CCC CCA CCT ACT ATA CCC CCA GAT GAA ACT TTT GGG    2007
Pro Ser Gly Thr Pro Pro Pro Thr Ile Pro Pro Asp Glu Thr Phe Gly
    510                 515                 520

GGG AGA GTG CCC AGA CCA GCC TTT GTC CAC TAT GAC AAG GAG GAG GCA    2055
Gly Arg Val Pro Arg Pro Ala Phe Val His Tyr Asp Lys Glu Glu Ala
525                 530                 535

TCT GAT GTG GAG ATC TCC TTG GAA AGT GAC TCT GAT GAC AGC GTG GTG    2103
Ser Asp Val Glu Ile Ser Leu Glu Ser Asp Ser Asp Asp Ser Val Val
540                 545                 550                 555

ATC GTG CCC GAG GGG CTT CCC CCC CTG CCA CCC CCA CCA CCC TCA GGT    2151
Ile Val Pro Glu Gly Leu Pro Pro Leu Pro Pro Pro Pro Ser Gly
            560                 565                 570
```

| | | |
|---|---|---|
| GCC ACA CCA CCC CCT ATA GCC CCC ACT GGG CCA CCA ACA GCC TCC CCT<br>Ala Thr Pro Pro Pro Ile Ala Pro Thr Gly Pro Pro Thr Ala Ser Pro<br>                575                      580                     585 | 2199 |
| CCT GTG CCA GCG AAG GAG GAG CCT GAA GAA CTT CCT GCG GCC CCA GGG<br>Pro Val Pro Ala Lys Glu Glu Pro Glu Glu Leu Pro Ala Ala Pro Gly<br>                590                     595                    600 | 2247 |
| CCT CTC CCG CCG CCC CCA CCT CCG CCG CCG CCT GTT CCT GGT CCT GTG<br>Pro Leu Pro Pro Pro Pro Pro Pro Pro Pro Pro Val Pro Gly Pro Val<br>        605                           610                     615 | 2295 |
| ACN CTC CCT CCA CCC CAG TTG GTC CCT GAA GGG ACT CCT GGT GGG GGA<br>Xaa Leu Pro Pro Pro Gln Leu Val Pro Glu Gly Thr Pro Gly Gly Gly<br>620                         625                     630                 635 | 2343 |
| GGA CCC CCA GCC CTG GAA GAG GAT TTG ACA GTT ATT AAT ATC AAC AGC<br>Gly Pro Pro Ala Leu Glu Glu Asp Leu Thr Val Ile Asn Ile Asn Ser<br>                640                     645                     650 | 2391 |
| AGT GAT GAA GAG GAG GAG GAA GAA GGA GAA GAG GAA GAA GAA GAA GAA<br>Ser Asp Glu Glu Glu Glu Glu Glu Gly Glu Glu Glu Glu Glu Glu Glu<br>        655                           660                     665 | 2439 |
| GAA GAA GAA GAG GAA GAA GAA GAA GAG GAA GAA GAG GAA GAG GAG GAA<br>Glu Glu Glu Glu Glu Glu Glu Glu Glu Glu Glu Glu Glu Glu Glu Glu<br>                670                     675                     680 | 2487 |
| GAC TTT GAG GAA GAG GAA GAG GAT GAA GAG GAA TAT TTT GAA GAG GAA<br>Asp Phe Glu Glu Glu Glu Glu Asp Glu Glu Glu Tyr Phe Glu Glu Glu<br>        685                           690                     695 | 2535 |
| GAA GAG GAG GAA GAA GAG TTT GAG GAA GAA TTT GAG GAA GAA GAA GGT<br>Glu Glu Glu Glu Glu Glu Phe Glu Glu Glu Phe Glu Glu Glu Glu Gly<br>700                       705                     710                 715 | 2583 |
| GAG TTA GAG GAA GAA GAA GAA GAG GAG GAT GAG GAG GAG GAA GAA GAA<br>Glu Leu Glu Glu Glu Glu Glu Glu Glu Asp Glu Glu Glu Glu Glu Glu<br>                720                     725                     730 | 2631 |
| CTG GAA GAG GTG GAA GAC CTG GAG TTT GGC ACA GCA GGA GGG GAG GTA<br>Leu Glu Glu Val Glu Asp Leu Glu Phe Gly Thr Ala Gly Gly Glu Val<br>                735                     740                     745 | 2679 |
| GAA GAA GGT GCA CCA CCA CCC CCA ACC CTG CCT CCA GCT CTG CCT CCC<br>Glu Glu Gly Ala Pro Pro Pro Pro Thr Leu Pro Pro Ala Leu Pro Pro<br>        750                           755                     760 | 2727 |
| CCT GAG TCT CCC CCA AAG GTG CAG CCA GAA CCC GAA CCC GAA CCC GGG<br>Pro Glu Ser Pro Pro Lys Val Gln Pro Glu Pro Glu Pro Glu Pro Gly<br>765                       770                     775 | 2775 |
| CTG CTT TTG GAA GTG GAG GAG CCA GGG ACG GAG GAG GAG CGT GGG GCT<br>Leu Leu Leu Glu Val Glu Glu Pro Gly Thr Glu Glu Glu Arg Gly Ala<br>780                       785                     790                 795 | 2823 |
| GAC ACA GCT CCC ACC CTG GCC CCT GAA GCG CTC CCC TCC CAG GGA GAG<br>Asp Thr Ala Pro Thr Leu Ala Pro Glu Ala Leu Pro Ser Gln Gly Glu<br>                800                     805                     810 | 2871 |
| GTG GAG AGG GAA GGG GAA AGC CCT GCG GCA GGG CCC CCT CCC CAG GAG<br>Val Glu Arg Glu Gly Glu Ser Pro Ala Ala Gly Pro Pro Pro Gln Glu<br>        815                         820                     825 | 2919 |
| CTT GTT GAA GAA GAG CCC TCT NCT CCC CCA ACC CTG TTG GAA GAG GAG<br>Leu Val Glu Glu Glu Pro Ser Xaa Pro Pro Thr Leu Leu Glu Glu Glu<br>                830                     835                     840 | 2967 |
| ACT GAG GAT GGG AGT GAC AAG GTG CAG CCC CCA CCA GAG ACA CCT GCA<br>Thr Glu Asp Gly Ser Asp Lys Val Gln Pro Pro Pro Glu Thr Pro Ala<br>845                       850                     855 | 3015 |
| GAA GAA GAG ATG GAG ACA GAG ACA GAG GCC GAA GCT CTC CAG GAA AAG<br>Glu Glu Glu Met Glu Thr Glu Thr Glu Ala Glu Ala Leu Gln Glu Lys<br>860                       865                     870                 875 | 3063 |
| GAG CAG GAT GAC ACA GCT GCC ATG CTG GCC GAC TTC ATC GAT TGT CCC<br>Glu Gln Asp Asp Thr Ala Ala Met Leu Ala Asp Phe Ile Asp Cys Pro<br>                880                     885                     890 | 3111 |

```
CCT GAT GAT GAG AAG CCA CCA CCT CCC ACA GAG CCT GAC TCC TAG C          3157
Pro Asp Asp Glu Lys Pro Pro Pro Pro Thr Glu Pro Asp Ser  *
            895                 900                 905

CATCTTCTGC ACCCCACCTC TTTGTTTCCA ATAAAGTTAT GTCCTTAAAA AAAA            3211
```

(2) INFORMATION FOR SEQ ID NO:9:

(i) SEQUENCE CHARACTERISTICS:
        (A) LENGTH: 905 amino acids
        (B) TYPE: amino acid
        (D) TOPOLOGY: linear (ii) MOLECULE TYPE: protein (xi) SEQUENCE DESCRIPTION: SEQ ID NO:9:

```
Met Glu Leu Ala Val Ala Val Leu Arg Asp Leu Leu Arg Tyr Ala Ala
 1               5                  10                  15

Gln Leu Pro Ala Leu Phe Arg Asp Ile Ser Met Asn His Leu Pro Gly
            20                  25                  30

Leu Leu Thr Ser Leu Leu Gly Leu Arg Pro Glu Cys Glu Gln Ser Ala
        35                  40                  45

Leu Glu Gly Met Lys Ala Cys Met Thr Tyr Phe Pro Arg Ala Cys Gly
    50                  55                  60

Ser Leu Lys Gly Lys Leu Ala Ser Phe Phe Leu Ser Arg Val Asp Ala
65                  70                  75                  80

Leu Ser Pro Gln Leu Gln Gln Leu Ala Cys Glu Cys Tyr Ser Arg Leu
                85                  90                  95

Pro Ser Leu Gly Ala Gly Phe Ser Gln Gly Leu Lys His Thr Glu Ser
            100                 105                 110

Trp Glu Gln Glu Leu His Ser Leu Leu Ala Ser Leu His Thr Leu Leu
        115                 120                 125

Gly Ala Leu Tyr Glu Gly Ala Glu Thr Ala Pro Val Gln Asn Glu Gly
    130                 135                 140

Pro Gly Val Glu Met Leu Leu Ser Ser Glu Asp Gly Asp Ala His Val
145                 150                 155                 160

Leu Leu Gln Leu Arg Gln Arg Phe Ser Gly Leu Ala Arg Cys Leu Gly
                165                 170                 175

Leu Met Leu Ser Ser Glu Phe Gly Ala Pro Val Ser Val Pro Val Gln
            180                 185                 190

Glu Ile Leu Asp Phe Ile Cys Arg Thr Leu Ser Val Ser Ser Lys Asn
        195                 200                 205

Ile Ser Leu His Gly Asp Gly Pro Cys Gly Cys Cys Cys Pro Leu
    210                 215                 220

Ser Thr Leu Lys Ala Leu Asp Leu Leu Ser Ala Leu Ile Leu Ala Cys
225                 230                 235                 240

Gly Ser Arg Leu Leu Arg Phe Gly Ile Leu Ile Gly Arg Leu Leu Pro
                245                 250                 255

Gln Val Leu Asn Ser Trp Ser Ile Gly Arg Asp Ser Leu Ser Pro Gly
            260                 265                 270

Gln Glu Arg Pro Tyr Ser Thr Val Arg Thr Lys Val Tyr Ala Ile Leu
        275                 280                 285

Glu Leu Trp Val Gln Val Cys Gly Ala Ser Ala Gly Met Leu Gln Gly
    290                 295                 300

Gly Ala Ser Gly Glu Ala Leu Leu Thr His Leu Leu Ser Asp Ile Ser
305                 310                 315                 320

Pro Pro Ala Asp Ala Leu Lys Leu Arg Ser Pro Arg Gly Ser Pro Asp
                325                 330                 335
```

```
Gly Ser Leu Gln Thr Gly Lys Pro Ser Ala Pro Lys Lys Leu Lys Leu
                340                 345                 350

Asp Val Gly Glu Ala Met Ala Pro Pro Ser His Leu Leu Leu Pro Val
                355                 360                 365

Pro Cys Lys Pro Ser Pro Ser Ala Ser Glu Lys Ile Ala Leu Arg Ser
                370                 375                 380

Pro Leu Ser Cys Ser Glu Ala Leu Val Thr Cys Ala Ala Leu Thr His
385                 390                 395                 400

Pro Arg Val Pro Pro Leu Gln Pro Met Gly Pro Thr Cys Pro Thr Pro
                405                 410                 415

Ala Pro Val Pro Leu Leu Arg Pro His Arg Pro Ser Gly Pro His Arg
                420                 425                 430

Ser Ile Leu Arg Ala Pro Cys Pro Gln Trp Ala Pro Cys Pro Gln Gln
                435                 440                 445

Ala Pro Cys Pro Ser Ala Gly Pro Met Pro Ser Ala Gly Pro Val Pro
                450                 455                 460

Ser Glu Pro Trp Thr Ser Thr Ala Asn Leu Leu Gly Leu Leu Ser
465                 470                 475                 480

Arg Pro Ser Val Cys Pro Pro Arg Leu Leu Pro Gly Pro Glu Asn His
                485                 490                 495

Arg Ala Gly Ser Asn Glu Asp Pro Ile Leu Ala Pro Ser Gly Thr Pro
                500                 505                 510

Pro Pro Thr Ile Pro Pro Asp Glu Thr Phe Gly Gly Arg Val Pro Arg
                515                 520                 525

Pro Ala Phe Val His Tyr Asp Lys Glu Glu Ala Ser Asp Val Glu Ile
                530                 535                 540

Ser Leu Glu Ser Asp Ser Asp Ser Val Val Ile Val Pro Glu Gly
545                 550                 555                 560

Leu Pro Pro Leu Pro Pro Pro Pro Ser Gly Ala Thr Pro Pro Pro
                565                 570                 575

Ile Ala Pro Thr Gly Pro Pro Thr Ala Ser Pro Pro Val Pro Ala Lys
                580                 585                 590

Glu Glu Pro Glu Glu Leu Pro Ala Ala Pro Gly Pro Leu Pro Pro Pro
                595                 600                 605

Pro Pro Pro Pro Pro Val Pro Gly Pro Val Xaa Leu Pro Pro Pro
                610                 615                 620

Gln Leu Val Pro Glu Gly Thr Pro Gly Gly Gly Pro Pro Ala Leu
625                 630                 635                 640

Glu Glu Asp Leu Thr Val Ile Asn Ile Asn Ser Ser Asp Glu Glu Glu
                645                 650                 655

Glu Glu Glu Gly Glu Glu Glu Glu Glu Glu Glu Glu Glu Glu Glu
                660                 665                 670

Glu Glu Glu Glu Glu Glu Glu Glu Glu Glu Asp Phe Glu Glu Glu
                675                 680                 685

Glu Glu Asp Glu Glu Glu Tyr Phe Glu Glu Glu Glu Glu Glu Glu
                690                 695                 700

Glu Phe Glu Glu Glu Phe Glu Glu Glu Gly Glu Leu Glu Glu Glu
705                 710                 715                 720

Glu Glu Glu Glu Asp Glu Glu Glu Glu Leu Glu Glu Val Glu
                725                 730                 735

Asp Leu Glu Phe Gly Thr Ala Gly Gly Glu Val Glu Glu Gly Ala Pro
                740                 745                 750

Pro Pro Pro Thr Leu Pro Pro Ala Leu Pro Pro Pro Glu Ser Pro Pro
```

```
                         755                 760                 765
Lys Val Gln Pro Glu Pro Glu Pro Gly Leu Leu Glu Val
    770                 775                 780
Glu Glu Pro Gly Thr Glu Glu Arg Gly Ala Asp Thr Ala Pro Thr
785                 790                 795                 800
Leu Ala Pro Glu Ala Leu Pro Ser Gln Gly Glu Val Glu Arg Glu Gly
                805                 810                 815
Glu Ser Pro Ala Ala Gly Pro Pro Gln Glu Leu Val Glu Glu
                820                 825                 830
Pro Ser Xaa Pro Pro Thr Leu Leu Glu Glu Thr Glu Asp Gly Ser
        835                 840                 845
Asp Lys Val Gln Pro Pro Glu Thr Pro Ala Glu Glu Met Glu
850                 855                 860
Thr Glu Thr Glu Ala Glu Ala Leu Gln Glu Lys Glu Gln Asp Asp Thr
865                 870                 875                 880
Ala Ala Met Leu Ala Asp Phe Ile Asp Cys Pro Pro Asp Asp Glu Lys
                885                 890                 895
Pro Pro Pro Pro Thr Glu Pro Asp Ser
            900                 905

(2) INFORMATION FOR SEQ ID NO:10:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:10:

Trp Leu Arg Lys
1

(2) INFORMATION FOR SEQ ID NO:11:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:11:

Ile Tyr Ile Lys Glu
1               5

(2) INFORMATION FOR SEQ ID NO:12:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:12:

Leu Thr Pro Val Ser Pro Glu Ser Ser Ser Thr Glu Glu Lys
1               5                   10
```

(2) INFORMATION FOR SEQ ID NO:13:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:13:

```
Asn Val Gly Glu Ser Val Ala Ala Ala Leu Ser Pro Leu Gly Ile Gln
 1               5                  10                  15

Val Asp Ile Asp Val Glu His Gly Gly Lys
            20                  25
```

(2) INFORMATION FOR SEQ ID NO:14:

(i) SEQUENCE CHARACTERISTICS:
        (A) LENGTH: 41 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:14:

```
Val Ala Ala Leu Phe Pro Ala Leu Arg Pro Gly Gly Phe Gln Ala His
 1               5                  10                  15

Tyr Arg Asp Glu Asp Gly Asp Leu Val Ala Phe Ser Ser Asp Glu Glu
            20                  25                  30

Leu Thr Met Ala Met Ser Tyr Val Lys
        35                  40
```

(2) INFORMATION FOR SEQ ID NO:15:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:15:

```
Gly Ser Pro Asp Gly Ser Leu Gln Thr Gly Lys Pro Ser Ala Pro Lys
 1               5                  10                  15

Ser
```

(2) INFORMATION FOR SEQ ID NO:16:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:16:

```
Leu Arg Ser Pro Arg Gly Ser Pro Asp Gly Ser Leu Gln Thr Gly Lys
 1               5                  10                  15
```

(2) INFORMATION FOR SEQ ID NO:17:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:17:

```
Leu Asp Val Gly Glu Ala Met Ala Pro Gln
 1               5                  10
```

(2) INFORMATION FOR SEQ ID NO:18:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:18:

```
Glu Gln Asp Asp Thr Ala Ala Val Leu Ala Asp Phe Ile Asp
 1               5                  10
```

(2) INFORMATION FOR SEQ ID NO:19:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:19:

```
Val Gln Pro Glu Pro Glu Pro Glu Pro Gly Leu Leu Glu Val Glu
 1               5                  10                  15

Glu Pro Gly Thr Glu Glu Glu Arg Gly Ala Asp Asp
                20                  25
```

(2) INFORMATION FOR SEQ ID NO:20:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:20:

```
Val Gln Pro Pro Pro Glu Thr Pro Ala Glu Glu Glu Met Glu Thr Glu
 1               5                  10                  15

Thr Glu Ala Glu Ala Leu Gln Glu Lys Glu Gly Gln Asp Asp Ala Ala
                20                  25                  30

Ala Met Leu
        35
```

(2) INFORMATION FOR SEQ ID NO:21:

(i) SEQUENCE CHARACTERISTICS:

```
          (A) LENGTH: 20 amino acids
          (B) TYPE: amino acid
          (D) TOPOLOGY: linear (ii) MOLECULE TYPE: peptide (v) FRAGMENT TYPE: internal (xi) SEQUENCE DESCRIPTION: SEQ ID NO:21:

Val Gln Pro Glu Pro Glu Pro Glu Pro Gly Leu Leu Leu Glu Val Glu
1               5                   10                  15

Glu Pro Gly Thr
            20

(2) INFORMATION FOR SEQ ID NO:22:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:22:

AGCGGCGGAA TTCCACC                                                  17

- -
```

We claim:

1. An isolated nuclecic acid molecule comprising a nucleotide sequence selected from the group consisting of:
   a) a nucleotide sequence shown in FIG. 1, SEQ ID NO:1; and
   b) a nucleotide sequence shown in FIG. 3, SEQ ID NO:3.

2. The isolated nucleic acid molecule of claim 1 comprising a coding region.

3. The isolated nucleic acid molecule of claim 1 comprising the nucleotide sequence shown in FIG. 1, SEQ ID NO:1.

4. An isolated nucleic acid molecule consisting of the nucleotide sequence shown if FIG. 1, SEQ ID NO:1.

5. An isolated nucleic acid molecule consisting of the nucleotide sequence encoding a polypeptide having an amino acid sequence shown if FIG. 2, SEQ ID NO:2.

6. An isolated nucleic acid molecule consisting of the nucleotide sequence encoding a polypeptide having an amino acid sequence shown if FIG. 4, SEQ ID NO:4.

7. An isolated nucleic acid molecule consisting of the nucleotide sequence encoding a polypeptide having an amino acid sequence shown if FIG. 4, SEQ ID NO:4.

8. An isolated nucleic acid molecule comprising a nucleotide sequence of the DNA insert of the plasmid deposited with the American Type Culture Collection (ATCC) an Accession Number 97387.

9. An isolated nucleic acid molecule comprising a nucleotide sequence of the DNA insert of the plasmid deposited with the American Type Culture Collection (ATCC) an Accession Number 97387.

10. An isolated nucleic acid molecule comprising a nucleotide sequence of the DNA insert of the plasmid deposited with the American Type Culture Collection (ATCC) an Accession Number 97386.

11. An isolated nucleic acid molecule comprising a nucleotide sequence of the DNA insert of the plasmid deposited with the American Type Culture Collection (ATCC) an Accession Number 97386.

12. An isolated nucleic acid molecule comprising about 50 nucleotides, wherein nucleic acid molecule hybridizes under high stringency conditions to an isolated nucleic acid molecule comprising a nucleotide sequence selected from the group consisting of:
   a) the complement of a nucleotide sequence shown in FIG. 1, SEQ ID NO:1; and
   b) the complement of a nucleotide sequence shown if FIG. 3, SEQ ID NO:3.

13. The isolated nucleic acid molecule of claim 12 comprising a nucleotide sequence encoding a polypeptide which binds to the S112 domain of p56$^{lck}$ shown in FIG. 5, SEQ ID NO:5.

14. The isolated nucleic acid molecule of claim 12 comprising about 100 nucleotides.

15. The isolated nucleic acid molecule of claim 12 consisting of 300 nucleotides.

16. An isolated nucleic acid molecule comprising a nucleotide sequence encoding a polypeptide having an amino acid sequence consisting of:
   shown in FIG. 2, SEQ ID NO:2.

17. An isolated nucleic acid molecule consisting of a nucleotide sequence selected from the group consisting of:
   a) nucleotides 1033 to 1386 of the nucleotide sequence shown in FIG. 1, SEQ ID NO:1; and
   b) nucleotides 907 to 1257 of the nucleotide sequence shown in FIG. 3, SEQ ID NO:3.

18. An isolated nucleic acid molecule consisting of nucleotide 67 to 216 of the nucleotide sequence shown in FIG. 1, SEQ ID NO:1.

19. An isolated nucleic acid molecule consisting of a nucleotide sequence selected from the group consisting of:
   a) nucleotides 448 to 555 of the nucleotide sequence shown in FIG. 1, SEQ ID NO:1; and
   b) nucleotides 322 to 429 of the nucleotide sequence shown in FIG. 1, SEQ ID NO:3.

20. An isolated nucleic acid molecule consisting of a nucleotide sequence selected from the group consisting of:
   a) nucleotides 262 to 312 of the nucleotide sequence shown in FIG. 1, SEQ ID NO:1; and
   b) nucleotides 136 to 186 of the nucleotide sequence shown in FIG. 3, SEQ ID NO:3.

21. A vector comprising an isolated nucleic acid molecule as in any one of claims 1, 2, 3, 4, 5, 6, 7, 8, 9, 10, 11, 12, 16, or 17.

22. A vector comprising a nucleotide sequence encoding a polypeptide consisting of an amino acid sequence selected from the group consisting of:
   a) an amino acid sequence shown in FIG. 2, SEQ ID NO:2; and
   b) an amino acid sequence shown in FIG. 4, SEQ ID NO:4.

23. A host cell comprising the vector of claim 21.

24. A host cell comprising the vector of claim 22.

25. A method of producing a p62 polypeptide comprising culturing a host cell of claim 23 in a suitable medium such that the p62 polypeptide is produced.

26. A method of producing a p62 polypeptide comprising culturing a host cell of claim 24 in a suitable medium such that the p62 polypeptide is produced.

27. A composition comprising the vector of claim 21.

28. A composition comprising the vector of claim 22.

* * * * *